US010724045B2

(12) United States Patent
Qu et al.

(10) Patent No.: US 10,724,045 B2
(45) Date of Patent: Jul. 28, 2020

(54) TRANSCRIPTION FACTORS THAT REGULATE NICOTINE BIOSYNTHESIS IN TOBACCO

(71) Applicant: North Carolina State University, Raleigh, NC (US)

(72) Inventors: Rongda Qu, Holly Springs, NC (US); Bingwu Wang, Harbin Heilongjiang (CN)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 16/059,696

(22) Filed: Aug. 9, 2018

(65) Prior Publication Data

US 2018/0362994 A1  Dec. 20, 2018

Related U.S. Application Data

(62) Division of application No. 15/412,443, filed on Jan. 23, 2017, now Pat. No. 10,072,270, which is a division of application No. 14/192,730, filed on Feb. 27, 2014, now Pat. No. 9,580,722.

(60) Provisional application No. 61/771,526, filed on Mar. 1, 2013.

(51) Int. Cl.
*C12N 15/82* (2006.01)
*A01H 6/82* (2018.01)
*A24B 15/10* (2006.01)

(52) U.S. Cl.
CPC .............................. *C12N 15/8243* (2013.01)

(58) Field of Classification Search
None
See application file for complete search history.

(56) References Cited

U.S. PATENT DOCUMENTS

| | | | |
|---|---|---|---|
| 6,624,083 | B2 | 9/2003 | Takahashi |
| 8,624,083 | B2 | 1/2014 | Page et al. |
| 2010/0192244 | A1 | 7/2010 | Page et al. |
| 2011/0039340 | A1 | 2/2011 | Timko et al. |
| 2011/0047660 | A1 | 2/2011 | Timko et al. |
| 2012/0284816 | A1* | 11/2012 | Page .................. C07K 14/415 800/260 |

FOREIGN PATENT DOCUMENTS

WO  2007/072224  6/2007

OTHER PUBLICATIONS

Todd et al, 2010, The Plant Journal, 62:589-600.*
Shoji et al, 2011, Plant Cell Physiol., 52:1117-1130.*
Zhang et al, 2012, Molecular Plant, 5:73-84.*
De Boer et al. "APETALA2/Ethylene Response Factor and basic helix-loop-helix tobacco transcription factors cooperatively mediate jasmonate-elicited nicotine biosynthesis" The Plant Journal, 66: 1053-1065, 2011.
De Geyter et al. "Transcriptional machineries in jasmonate-elicited plant secondary metabolism" Trends in Plant Science, 17(6): 349-359, 2012.
Dewey et al. "Molecular genetics of alkaloid biosynthesis in Nicotiana tabacum", Phytochemistry, 94:10-27, 2013.
Shoji et al. "Clustered Transcription Factor Genes Regulate Nicotine Biosynthesis in Tobacco", The Plant Cell, 22: 3390-3409, 2010.
Shoji et al. "Tobacco MYC2 Regulates Jasmonate-Inducible Nicotine Biosynthesis Genes Directly and By Way of the NIC2-Locus ERF Genes" Plant Cell Physiol, 52(6): 1117-1130, 2011.
Todd et al. "A functional genomics screen identifies diverse transcription factors that regulate alkaloid biosynthesis in Nicotiana benthamiana", The Plant Journal, 62: 589-600, 2010.
Wang, Bingwu. "Factors in Nicotine Biosynthesis in Tobacco", Dissertation. North Carolina State University, Raleigh North Carolina. 131 pages. Mar. 4, 2012.
Zhang et al. "Tobacco Transcription Factors NtMYC2a and NtMYC2b Form Nuclear Complexes with the NtJAZ1 Repressor and Regulate Multiple Jasmonate-Inducible Steps in Nicotine Biosynthesis", Molecular Plant, 5(1): 73-84, 2012.
Chen et al. "Complete sequence of the binary vector pBI121 and its application in cloning T-DNA insertion from transgenic plants", Molecular Breeding, 11: 287-293, Jan. 5, 2003.
Shoji et al. "Tobacco MYC2 Regulates Jasmonate-Inducible Nicotine Biosynthesis Genes Directly and By Way of the NIC2-Locus ERF Genes", Plant Cell Physiol., 52(6): 1117-1130, May 16, 2011.
International Search Report and Written Opinion Corresponding to International Application No. PCT/US2014/019136; dated Jun. 3, 2014; 13 Pages.
Saitoh F., Noma M., and Kawashima N., The alkaloid contents of sixty Nicotiana species. Phytochemistry 24, 1985, pp. 477-480.
Sato F., Hashimoto T., Hachiya A. Tamura K-I, Choi KB, Morishige T., Fujimoto H., and Yamada T., Metabolic engineering of plant alkaloid biosyntheses, PNAS 98, 2001, pp. 1117-1130.
North Carolina State University repository citation to Wang, B. "Factors in Nicotine Biosynthesis in Tobacco", Dissertation, http://repository.lib.ncsu.edu/ir/handle/1840.16/8385, accessed May 18, 2016.
International Preliminary Report on Patentability corresponding to International Application No. PCT/US2014/019136, dated Sep. 1, 2015.
Fourgoux-Nicol A et al. Isolation of rapeseed genes expressed early and specifically during development of the male gametophyte. Plant Molecular Biology. 1999; 40: 857-172.

* cited by examiner

*Primary Examiner* — Jason Deveau Rosen
(74) *Attorney, Agent, or Firm* — Myers Bigel, P.A.

(57) ABSTRACT

The present invention provides nucleic acids encoding transcription factors and methods of using these nucleic acids to modulate nicotine production in plants and to produce plants having modulated nicotine production.

8 Claims, 20 Drawing Sheets

Specification includes a Sequence Listing.

SEQUENCE LISTING

<160> NUMBER OF SEQ ID NOS: 43

<210> SEQ ID NO 1
<211> LENGTH: 2241
<212> TYPE: DNA
<213> ORGANISM: Nicotiana tabacum

<400> SEQUENCE: 1

```
cacacactct ctccattttc actcactcct tatcaccaaa caattcttgg gtgtttgaat      60
atatacccga ataatttcc tctctgtatc aagaatcaaa cagatctgaa ttgatttgtc     120
tgtttttttt tcttgatttt gttatatgga atgacggatt atagaatacc aacgatgact    180
aatatatgga gcaatactac atccgatgat aatatgatgg aagcttttt atcttctgat     240
ccgtcgtcgt tttggcccgg aacaactact acaccaactc cccggagttc agtttctcca    300
gcgccggcgc cggtgacggg gattgccgga gacccattaa agtctatgcc atatttcaac    360
caagagtcac tgcaacagcg actccagact ttaatcgatg gggctcgcaa agggtggacg    420
tatgccatat tttggcaatc gtctgttgtg gatttcgcga gccctcggt tttggggtgg      480
ggagatgggt attataaagg tgaagaagat aaaaataagc gtaaaacggc gtcgttttcg    540
cctgacttta tcacggaaca agcacaccgg aaaaaggttc tccgggagct gaattcttta    600
attccggca cacaaaccgg tggtgaaaat gatgctgtag atgaagaagt aactgatact      660
gaatggtttt ttctgatttc catgacacaa tcgtttgtta acggaagcgg gcttccgggc    720
ctggcgatgt atagttcaag cccgatttgg gttactggaa cagagagatt agctgttct     780
cactgtgaac gggcccgaca ggcccaaggt ttcgggcttc agactattgt ttgtattcct    840
tcagctaatg tgttgttga gctcgggtca actgagttga tattccagac tgctgattta     900
atgaacaagg ttaaagtttt gtttaattttt aatattgata tgggtgcgac tacgggctca    960
ggatcgggct catgtgctat tcaggccgag cccgatcctt cagcccttg gctgactgat     1020
ccggcttctt cagttgtgga agtcaaggat tcgtcgaata cagttccttc aaggaatacc    1080
agtaagcaac ttgtgtttgg aaatgagaat tctgaaaatg gtaatcaaaa ttctcagcaa    1140
acacaaggat ttttcactag ggagttgaat ttttccgaat atggatttga tggaagtaat    1200
actcggtatg gaaatgggaa tgcgaattct tcgcgttctt gcaagcctga gtctggtgaa    1260
atcttgaatt ttggtgatag tactaagagg agtgcttgca gtgcaaatgg gagcttgttt    1320
tcgggccaat cacagttcgg gcccgggcct gcggaggaga acaagaacaa gaacaagaaa    1380
aggtcacctg catcaagagg aagcaacgat gaaggaatcc tttcatttgt tcgggtgtg    1440
attttgccaa gttcaaacac ggggaagtcc ggtggaggtg gcgattcgga tcaatcagat    1500
ctcgaggctt cggtggtgaa ggaggcgat agtagtagag ttgtagaccc cgagaagaag    1560
ccgaggaaac gagggaggaa accggctaac gggagagagg agccattgaa tcatgtggag    1620
gcagagagac aaaggaggga gaaattgaat caaagattct atgcacttag agctgttgta    1680
```

```
ccaaatgtgt caaaaatgga taaagcatca cttcttggtg atgcaattgc atttatcaat      1740
gagttgaaat caaggttca gaattctgac tcagataaag aggacttgag gaaccaaatc      1800
gaatctttaa ggaatgaatt agccaacaag ggatcaaact ataccggtcc tcccccgtca      1860
aatcaagaac tcaagattgt agatatggac atcgacgtta aggtgatcgg atgggatgct      1920
atgattcgta tacaatctaa taaaaagaac catccagccg cgaggttaat gaccgctctc      1980
atggaattgg acttagatgt gcaccatgct agtgtttcag ttgtcaacga gttgatgatc      2040
caacaagcga ctgtgaaaat gggaagccgg ctttacacgc aagaacaact tcggatatca      2100
ttgacatcca gaattgctga atcgcgatga agagaaatac agtaaatgga aattatcata      2160
gtgagctctg aataatgtta tctttcattg agctatttta agagaatttc tcctaaaaaa      2220
aaaaaaaaaa aaaaaaaaaa a                                                 2241

<210> SEQ ID NO 2
<211> LENGTH: 659
<212> TYPE: PRT
<213> ORGANISM: Nicotiana tabacum

<400> SEQUENCE: 2
```

Met Thr Asp Tyr Arg Ile Pro Thr Met Thr Asn Ile Trp Ser Asn Thr
1               5                   10                  15

Thr Ser Asp Asp Asn Met Met Glu Ala Phe Leu Ser Ser Asp Pro Ser
            20                  25                  30

Ser Phe Trp Pro Gly Thr Thr Thr Pro Thr Pro Arg Ser Ser Val
        35                  40                  45

Ser Pro Ala Pro Ala Pro Val Thr Gly Ile Ala Gly Asp Pro Leu Lys
    50                  55                  60

Ser Met Pro Tyr Phe Asn Gln Glu Ser Leu Gln Gln Arg Leu Gln Thr
65                  70                  75                  80

Leu Ile Asp Gly Ala Arg Lys Gly Trp Thr Tyr Ala Ile Phe Trp Gln
                85                  90                  95

Ser Ser Val Val Asp Phe Ala Ser Pro Ser Val Leu Gly Trp Gly Asp
            100                 105                 110

Gly Tyr Tyr Lys Gly Glu Glu Asp Lys Asn Lys Arg Lys Thr Ala Ser
        115                 120                 125

Phe Ser Pro Asp Phe Ile Thr Glu Gln Ala His Arg Lys Lys Val Leu
    130                 135                 140

Arg Glu Leu Asn Ser Leu Ile Ser Gly Thr Gln Thr Gly Gly Glu Asn
145                 150                 155                 160

Asp Ala Val Asp Glu Glu Val Thr Asp Thr Glu Trp Phe Phe Leu Ile
                165                 170                 175

Ser Met Thr Gln Ser Phe Val Asn Gly Ser Gly Leu Pro Gly Leu Ala
            180                 185                 190

Met Tyr Ser Ser Ser Pro Ile Trp Val Thr Gly Thr Glu Arg Leu Ala
        195                 200                 205

Val Ser His Cys Glu Arg Ala Arg Gln Ala Gln Gly Phe Gly Leu Gln
    210                 215                 220

Thr Ile Val Cys Ile Pro Ser Ala Asn Gly Val Val Glu Leu Gly Ser
225                 230                 235                 240

Thr Glu Leu Ile Phe Gln Thr Ala Asp Leu Met Asn Lys Val Lys Val
                245                 250                 255

Leu Phe Asn Phe Asn Ile Asp Met Gly Ala Thr Thr Gly Ser Gly Ser
            260                 265                 270

```
Gly Ser Cys Ala Ile Gln Ala Glu Pro Asp Pro Ser Ala Leu Trp Leu
            275                 280                 285
Thr Asp Pro Ala Ser Ser Val Val Glu Val Lys Asp Ser Ser Asn Thr
290                 295                 300
Val Pro Ser Arg Asn Thr Ser Lys Gln Leu Val Phe Gly Asn Glu Asn
305                 310                 315                 320
Ser Glu Asn Gly Asn Gln Asn Ser Gln Gln Thr Gln Gly Phe Phe Thr
                325                 330                 335
Arg Glu Leu Asn Phe Ser Glu Tyr Gly Phe Asp Gly Ser Asn Thr Arg
            340                 345                 350
Tyr Gly Asn Gly Asn Ala Asn Ser Ser Arg Ser Cys Lys Pro Glu Ser
            355                 360                 365
Gly Glu Ile Leu Asn Phe Gly Asp Ser Thr Lys Arg Ser Ala Cys Ser
370                 375                 380
Ala Asn Gly Ser Leu Phe Ser Gly Gln Ser Gln Phe Gly Pro Gly Pro
385                 390                 395                 400
Ala Glu Glu Asn Lys Asn Lys Asn Lys Lys Arg Ser Pro Ala Ser Arg
                405                 410                 415
Gly Ser Asn Asp Glu Gly Ile Leu Ser Phe Val Ser Gly Val Ile Leu
            420                 425                 430
Pro Ser Ser Asn Thr Gly Lys Ser Gly Gly Gly Gly Asp Ser Asp Gln
            435                 440                 445
Ser Asp Leu Glu Ala Ser Val Val Lys Glu Ala Asp Ser Ser Arg Val
450                 455                 460
Val Asp Pro Glu Lys Lys Pro Arg Lys Arg Gly Arg Lys Pro Ala Asn
465                 470                 475                 480
Gly Arg Glu Glu Pro Leu Asn His Val Glu Ala Glu Arg Gln Arg Arg
                485                 490                 495
Glu Lys Leu Asn Gln Arg Phe Tyr Ala Leu Arg Ala Val Val Pro Asn
            500                 505                 510
Val Ser Lys Met Asp Lys Ala Ser Leu Leu Gly Asp Ala Ile Ala Phe
            515                 520                 525
Ile Asn Glu Leu Lys Ser Lys Val Gln Asn Ser Asp Ser Asp Lys Glu
530                 535                 540
Asp Leu Arg Asn Gln Ile Glu Ser Leu Arg Asn Glu Leu Ala Asn Lys
545                 550                 555                 560
Gly Ser Asn Tyr Thr Gly Pro Pro Ser Asn Gln Glu Leu Lys Ile
                565                 570                 575
Val Asp Met Asp Ile Asp Val Lys Val Ile Gly Trp Asp Ala Met Ile
            580                 585                 590
Arg Ile Gln Ser Asn Lys Lys Asn His Pro Ala Ala Arg Leu Met Thr
            595                 600                 605
Ala Leu Met Glu Leu Asp Leu Asp Val His His Ala Ser Val Ser Val
610                 615                 620
Val Asn Glu Leu Met Ile Gln Gln Ala Thr Val Lys Met Gly Ser Arg
625                 630                 635                 640
Leu Tyr Thr Gln Glu Gln Leu Arg Ile Ser Leu Thr Ser Arg Ile Ala
                645                 650                 655
Glu Ser Arg

<210> SEQ ID NO 3
<211> LENGTH: 2416
<212> TYPE: DNA
```

<213> ORGANISM: Nicotiana tabacum

<400> SEQUENCE: 3

```
gtaacaaacc ctctccattt tcactcactc caaaaaactt tcctctctat tttttctctc      60
tgtatcaaga atcaaacaga tctgaattga tttgggagtt ttttttcttc ttgttttgt      120
tatatggaat gacggactat agaataccaa cgatgactaa tatatggagc aatacaacat    180
ccgacgataa catgatggaa gcttttttat cttctgatcc gtcgtcgttt tgggccggaa    240
caaatacacc aactccacgg agttcagttt ctccggcgcc ggcgccggtg acggggattg    300
ccggagaccc attaaagtcg atgccgtatt caaccaaga gtcgctgcaa cagcgactcc     360
agacgttaat cgacggggct cgcgaagcgt ggacttacgc catattctgg caatcgtctg    420
ttgtggattt cgtgagcccc tcggtgttgg ggtggggaga tggatattat aaaggagaag    480
aagacaagaa taagcgtaaa acggcggcgt tttcgcctga ttttattacg gagcaagaac    540
accggaaaaa agttctccgg gagctgaatt ctttaatttc cggcacacaa actggtggtg    600
aaaatgatgc tgtagatgaa gaagtaacgg atactgaatg gttttttctg atttcaatga    660
ctcaatcgtt tgttaacgga agcgggcttc cgggcctggc tatgtacagc tcaagcccga    720
tttgggttac tggaagagaa agattagctg cttctcactg tgaacgggcc cgacaggccc    780
aaggtttcgg gcttcagact atggtttgta ttccttcagc taatggtgtt gttgagctcg    840
ggtcaactga gttgatattc cagagcgctg atttaatgaa caaggttaaa atcttgtttg    900
attttaatat tgatatgggc gcgactacgg gctcaggttc gggctcatgt gctattcagg    960
ctgagcccga tccttcaacc ctttggctta cggatccacc ttcctcagtt gtggaagtca   1020
aggattcgtc gaatacagtt ccttcaagta atagtagtaa gcaacttgtg tttggaaatg   1080
agaattctga aaatgttaat caaaattctc agcaaacaca aggattttc actagggagt    1140
tgaatttttc gaatatgga tttgatggaa gtaatactag gagtggaaat gggaatgtga    1200
attcttcgcg ttcttgcaag cctgagtctg gcgaaatctt gaattttggt gatagtacta   1260
agagaaatgc ttcaagtgca aatgggagct tgttttcggg ccaatcgcag ttcggtcccg    1320
ggcctgcgga ggagaacaag aacaagaaca agaaaaggtc acctgcatca agaggaagca   1380
atgaagaagg aatgctttca tttgtttcgg gtgtgatctt gccaagttca aacacgggga   1440
agtccggtgg aggtggcgat tcggatcatt cagatctcga ggcttcggtg gtgaaggagg    1500
cggatagtag tagagttgta gaccccgaga gaggccgag gaaacgagga aggaaaccgg    1560
ctaacgggag agaggagcca ttgaatcatg tggaggcaga gaggcaaagg agggagaaat    1620
tgaatcaaag attctatgca cttagagctg ttgtaccaaa tgtgtcaaaa atggataaag    1680
catcacttct tggtgatgca attgcattta tcaatgagtt gaaatcaaag gttcagaatt    1740
ctgactcaga taaagatgag ttgaggaacc aaattgaatc tttaaggaat gaattagcca    1800
acaagggatc aaactatacc ggtcctccac cgccaaatca agatctcaag attgtagata   1860
tggatatcga cgttaaagtc atcggatggg atgctatgat tcgtatacaa tctaataaaa   1920
agaaccatcc agccgcgagg ttaatggccg ctctcatgga attggactta gatgtgcacc    1980
atgctagtgt ttcagttgtc aacgagttga tgatccaaca agcgacagtg aaaatgggga    2040
gccggcttta cacgcaagag cagcttcgga tatcattgac atccagaatt gctgaatcgc    2100
gatgaagaga aatacagtaa atggaaatta ttagtgagct ctgaataatg ttatctttca    2160
ttgagctatt ttaagagaat ttctcctata gttgatctt gagattaagg ctacttaaaa     2220
gtggaaagtt gattgagctt tcctcttagt tttttgggta ttttccaact tttatatcta    2280
```

-continued

```
gtttgttttc cacattttct gtacatataa tgtgaaacca atactagatc tcaagatctg    2340
gtttttagtt ctgtaattag aaataaatat gcagcttcat cttttctgt taaaaaaaaa     2400 aaaaaaaaaa aaaaaa                                                    2416
```

<210> SEQ ID NO 4
<211> LENGTH: 658
<212> TYPE: PRT
<213> ORGANISM: Nicotiana tabacum

<400> SEQUENCE: 4

```
Met Thr Asp Tyr Arg Ile Pro Thr Met Thr Asn Ile Trp Ser Asn Thr
1               5                   10                  15

Thr Ser Asp Asp Asn Met Met Glu Ala Phe Leu Ser Ser Asp Pro Ser
            20                  25                  30

Ser Phe Trp Ala Gly Thr Asn Thr Pro Thr Pro Arg Ser Ser Val Ser
        35                  40                  45

Pro Ala Pro Ala Pro Val Thr Gly Ile Ala Gly Asp Pro Leu Lys Ser
    50                  55                  60

Met Pro Tyr Phe Asn Gln Glu Ser Leu Gln Gln Arg Leu Gln Thr Leu
65                  70                  75                  80

Ile Asp Gly Ala Arg Glu Ala Trp Thr Tyr Ala Ile Phe Trp Gln Ser
                85                  90                  95

Ser Val Val Asp Phe Val Ser Pro Val Leu Gly Trp Gly Asp Gly
            100                 105                 110

Tyr Tyr Lys Gly Glu Glu Asp Lys Asn Lys Arg Lys Thr Ala Ala Phe
        115                 120                 125

Ser Pro Asp Phe Ile Thr Glu Gln Glu His Arg Lys Lys Val Leu Arg
    130                 135                 140

Glu Leu Asn Ser Leu Ile Ser Gly Thr Gln Thr Gly Gly Glu Asn Asp
145                 150                 155                 160

Ala Val Asp Glu Glu Val Thr Asp Thr Glu Trp Phe Phe Leu Ile Ser
                165                 170                 175

Met Thr Gln Ser Phe Val Asn Gly Ser Gly Leu Pro Gly Leu Ala Met
            180                 185                 190

Tyr Ser Ser Ser Pro Ile Trp Val Thr Gly Arg Glu Arg Leu Ala Ala
        195                 200                 205

Ser His Cys Glu Arg Ala Arg Gln Ala Gln Gly Phe Gly Leu Gln Thr
    210                 215                 220

Met Val Cys Ile Pro Ser Ala Asn Gly Val Val Glu Leu Gly Ser Thr
225                 230                 235                 240

Glu Leu Ile Phe Gln Ser Ala Asp Leu Met Asn Lys Val Lys Ile Leu
                245                 250                 255

Phe Asp Phe Asn Ile Asp Met Gly Ala Thr Thr Gly Ser Gly Ser Gly
            260                 265                 270

Ser Cys Ala Ile Gln Ala Glu Pro Asp Pro Ser Thr Leu Trp Leu Thr
        275                 280                 285

Asp Pro Pro Ser Ser Val Val Glu Val Lys Asp Ser Ser Asn Thr Val
    290                 295                 300

Pro Ser Ser Asn Ser Ser Lys Gln Leu Val Phe Gly Asn Glu Asn Ser
305                 310                 315                 320

Glu Asn Val Asn Gln Asn Ser Gln Gln Thr Gln Gly Phe Phe Thr Arg
                325                 330                 335

Glu Leu Asn Phe Ser Glu Tyr Gly Phe Asp Gly Ser Asn Thr Arg Ser
```

-continued

```
            340                 345                 350
Gly Asn Gly Asn Val Ser Ser Arg Ser Cys Lys Pro Glu Ser Gly
            355                 360                 365
Glu Ile Leu Asn Phe Gly Asp Ser Thr Lys Arg Asn Ala Ser Ser Ala
370                 375                 380
Asn Gly Ser Leu Phe Ser Gly Gln Ser Gln Phe Gly Pro Gly Pro Ala
385                 390                 395                 400
Glu Glu Asn Lys Asn Lys Asn Lys Lys Arg Ser Pro Ala Ser Arg Gly
                405                 410                 415
Ser Asn Glu Glu Gly Met Leu Ser Phe Val Ser Gly Val Ile Leu Pro
            420                 425                 430
Ser Ser Asn Thr Gly Lys Ser Gly Gly Gly Asp Ser Asp His Ser
            435                 440                 445
Asp Leu Glu Ala Ser Val Val Lys Glu Ala Asp Ser Ser Arg Val Val
            450                 455                 460
Asp Pro Glu Lys Arg Pro Arg Lys Arg Gly Arg Lys Pro Ala Asn Gly
465                 470                 475                 480
Arg Glu Glu Pro Leu Asn His Val Glu Ala Glu Arg Gln Arg Glu
                485                 490                 495
Lys Leu Asn Gln Arg Phe Tyr Ala Leu Arg Ala Val Val Pro Asn Val
                500                 505                 510
Ser Lys Met Asp Lys Ala Ser Leu Leu Gly Asp Ala Ile Ala Phe Ile
            515                 520                 525
Asn Glu Leu Lys Ser Lys Val Gln Asn Ser Asp Ser Asp Lys Asp Glu
            530                 535                 540
Leu Arg Asn Gln Ile Glu Ser Leu Arg Asn Glu Leu Ala Asn Lys Gly
545                 550                 555                 560
Ser Asn Tyr Thr Gly Pro Pro Pro Asn Gln Asp Leu Lys Ile Val
                565                 570                 575
Asp Met Asp Ile Asp Val Lys Val Ile Gly Trp Asp Ala Met Ile Arg
                580                 585                 590
Ile Gln Ser Asn Lys Lys Asn His Pro Ala Ala Arg Leu Met Ala Ala
            595                 600                 605
Leu Met Glu Leu Asp Leu Asp Val His His Ala Ser Val Ser Val Val
            610                 615                 620
Asn Glu Leu Met Ile Gln Gln Ala Thr Val Lys Met Gly Ser Arg Leu
625                 630                 635                 640
Tyr Thr Gln Glu Gln Leu Arg Ile Ser Leu Thr Ser Arg Ile Ala Glu
                645                 650                 655
Ser Arg
```

<210> SEQ ID NO 5
<211> LENGTH: 1038
<212> TYPE: DNA
<213> ORGANISM: Nicotiana tabacum

<400> SEQUENCE: 5

```
caccgtctct ttccatttct ttctcttaaa agaaaaaaca tctcaataac aaaaagaaaa      60
atgtgtggag gtgccataat ccccgactat gaacccgtcg gaaaccgctg ccggaaaatc     120
actgctagtg acctctgggc tgagcttgac cctatctccg acttctggtc ttcctcttcc     180
tcttcctcct ccattgccgg caaatctgat tccgttcagt cgctaaccca ctcctacaat     240
aagcctcaga atcagattc cggcaaactt aatcaactcg aaaaaggtac aataagtgtg     300
```

```
aaggttgaga aggagagcag tggcccaagg gcgaggaaga acaaatacag aggaataagg        360
cagagaccgt ggggaaaatg ggctgctgag atacgtgatc ctcagaaagg cgtccgcgtg        420
tggttaggta cattcaacac ggctgaggaa gctgccaggg catatgacga ggctgcaaag        480
cgaatccgcg gtgacaaggc taagctcaac tttccagagc caccttcgcc accagccaag        540
cgacactgca ctagcaccat ccctgatcag cccacacgtt ctgacttaat gtctcagaaa        600
ccggcctcaa taatgttgaa ctatggatat gaaaaccaaa caccctacta ccccatggaa        660
atgcccgctg ctgaggatcc tcaacatcat gattatgagc tcaaggagca gatttccaac        720
ttggagtcat tcctggattt agagccagac tcagggatcg tcgattctga cccccctcaat       780 attttctga tggatgactt tgctgcaact cagcagcagc agctgtttta ctgaacactg         840
taaaaattat catatactac tagttaattt catcctaagt tgtttggtgt gcgttttctg        900
atgagtgact agttagcttt tggtagtacg tagtacaatg cagaaagtac atacaataat        960
aagttgcgtg cctttgcatg caatttgtaa tattaatgtc atgttgtttt gtgctgttta       1020
aaaaaaaaaa aaaaaaaa                                                     1038

<210> SEQ ID NO 6
<211> LENGTH: 257
<212> TYPE: PRT
<213> ORGANISM: Nicotiana tabacum

<400> SEQUENCE: 6

Met Cys Gly Gly Ala Ile Ile Pro Asp Tyr Glu Pro Val Gly Asn Arg
1               5                   10                  15

Cys Arg Lys Ile Thr Ala Ser Asp Leu Trp Ala Glu Leu Asp Pro Ile
                20                  25                  30

Ser Asp Phe Trp Ser Ser Ser Ser Ser Ser Ser Ile Ala Gly Lys
                35                  40                  45

Ser Asp Ser Val Gln Ser Leu Thr His Ser Tyr Asn Lys Pro Gln Lys
        50                  55                  60

Ser Asp Ser Gly Lys Leu Asn Gln Leu Glu Lys Gly Thr Ile Ser Val
65                  70                  75                  80

Lys Val Glu Lys Glu Ser Ser Gly Pro Arg Ala Arg Lys Asn Lys Tyr
                85                  90                  95

Arg Gly Ile Arg Gln Arg Pro Trp Gly Lys Trp Ala Ala Glu Ile Arg
                100                 105                 110

Asp Pro Gln Lys Gly Val Arg Val Trp Leu Gly Thr Phe Asn Thr Ala
            115                 120                 125

Glu Glu Ala Ala Arg Ala Tyr Asp Glu Ala Ala Lys Arg Ile Arg Gly
        130                 135                 140

Asp Lys Ala Lys Leu Asn Phe Pro Glu Pro Ser Pro Pro Ala Lys
145                 150                 155                 160

Arg His Cys Thr Ser Thr Ile Pro Asp Gln Pro Thr Arg Ser Asp Leu
                165                 170                 175

Met Ser Gln Lys Pro Ala Ser Ile Met Leu Asn Tyr Gly Tyr Glu Asn
                180                 185                 190

Gln Thr Pro Tyr Tyr Pro Met Glu Met Pro Ala Ala Glu Asp Pro Gln
            195                 200                 205

His His Asp Tyr Glu Leu Lys Glu Gln Ile Ser Asn Leu Glu Ser Phe
        210                 215                 220

Leu Asp Leu Glu Pro Asp Ser Gly Ile Val Asp Ser Asp Pro Leu Asn
225                 230                 235                 240
```

Ile Phe Leu Met Asp Asp Phe Ala Ala Thr Gln Gln Gln Gln Leu Phe
            245                 250                 255

Tyr

<210> SEQ ID NO 7
<211> LENGTH: 2458
<212> TYPE: DNA
<213> ORGANISM: Nicotiana tabacum

<400> SEQUENCE: 7

| | | | | | |
|---|---|---|---|---|---|
| agcaaaaggg | tttgaagatg | atgtgtggac | ttattgatct | aaatactgtg | gataacgatg | 60 |
| acgtcggaga | agaaacgacg | gcgccggtgt | caccagcgtc | atcgtcgacg | gcgtctggat | 120 |
| gttcggattt | gacgtcgtca | tctctgccgg | cgatggcatc | ggtttgtctg | gagctgtggc | 180 |
| atgcgtgtgc | tggaccgttg | atttctctgc | cgaagaaagg | aagtgctgtt | gtgtacctac | 240 |
| ctcaaggtca | cttggaacat | ctctctgagt | acccgcccat | agcctataac | ctccctcctc | 300 |
| acgttttttg | tcgcgtcgta | gacgtgaagc | tacaagcgga | tgcggcgagt | gatgaggtct | 360 |
| atgcacaagt | ctcactggtt | ccagacaatc | agattgagca | gaaatggagg | gatggagaca | 420 |
| ttgatgcaga | tactgaagag | gaggaaatag | aaggtgctgg | aaaatcaaca | acaccacaca | 480 |
| tgttctgcaa | gactctcact | gcttcggata | ccagcactca | tggcggtttt | tctgtccctc | 540 |
| gccgggctgc | agaagattgc | tttcctccat | tggattacag | acaacagcgg | ccctcacagg | 600 |
| agctggtagc | caaagatcta | catggtatcg | agtggaaatt | tcggcatatc | tatcgtggtc | 660 |
| agccacgaag | gcatctgctc | actacaggat | ggagtgcgtt | tgtaaacagg | aagaagcttg | 720 |
| tttctggtga | cgctgtgctt | ttcttaagga | ctgctgatga | agaacttagg | ctaggggtga | 780 |
| gacgagctgc | ccaagctaaa | acatgttcaa | attatctagc | tgcctatagc | caactgttga | 840 |
| atgtcagtgg | tattgtggat | gtggttaagg | ccatatctag | cacaaatgcc | ttcagtatct | 900 |
| gttataaccc | gagggctagc | tcatcaggct | tcattttacc | ttaccacaaa | ttctcaaaga | 960 |
| ctcttgcaca | tccctttca | gctggaatga | gatttaagat | gcgtgtcgaa | acagaagatg | 1020 |
| cagctgaaca | aaggttcact | ggacttgttg | taggagtcag | cgatgtagat | ccagttcgct | 1080 |
| ggcctggttc | taaatggagg | tgcctattgg | tcaggtggga | tgatcttgat | gtttctcggc | 1140 |
| ataatagggt | ttcaccgtgg | gaaattgagc | catctggttc | agctcctgta | tccagcagct | 1200 |
| tggtgatgcc | ttctgcgaag | aggaccaggg | ttggcttttcc | aattacaaag | gccgattttc | 1260 |
| caattcctag | agatgggatt | gcagtatcag | actttgggga | atcttctagg | ttccagaagg | 1320 |
| tcttgcaagg | tcaagaaatt | tggggattag | ttctcctttt | tgtcggtttt | gatgctcaca | 1380 |
| gtcctcgtac | agcggggata | agatgctttc | ctggttttcc | tagttctggg | gcatctagat | 1440 |
| tgggaaacag | catcagaacc | ctgcttggtg | acacagacaa | gtcccctgaa | agcattggct | 1500 |
| ttagtgattc | ttctcgatac | aataaggtct | tgcaaggtca | gaaacttttt | tcaacccctc | 1560 |
| cttatgggag | aggtcatgca | ggtagcctaa | tgcaggaaaa | aagtagaact | ggtattatcg | 1620 |
| tcggtattca | ggttccaagc | cacgtaaaca | ggtggtctgc | tccaaatcag | ggtaatcgca | 1680 |
| gtcattgcaa | tccaagtact | cttgtcccgg | catcatcacc | tccttctgtg | ctcagctttc | 1740 |
| agcctcccag | gtctccagca | tcaaaattcc | aggctatgtt | caatcataaa | catgggaagc | 1800 |
| ttgagactgc | tacccaggct | ttggatatgt | ctgagagctg | tagtaggcat | ctcgcatctg | 1860 |
| gctcacatgc | cgaggacatc | agtaggaagg | agacacaaa | aggaatcagt | tcttttagtt | 1920 |
| tcttaaagga | gcaaaagcaa | acaggaattt | catatctttc | tcttgggacc | cagtcgtctc | 1980 |

```
aaaacttagt tttccatgtgt aaaaccagtt gcaggatctt tggattcccc ttgaccgaga    2040
gtaaaataaa tgcagctaga gcggagaatc ctgccgaggc tgtatattca catggtctag    2100
aaacaacatt tctgccttcc agtgatggaa agttgcagcc agggccacca ttgatgacta    2160
atgttgtggg aacaaacttt actaaagtaa atgacctcta tgctgcaaga gatgtgattc    2220
ttgatattgc tttgtagcaa gtatttgttg tgaagtcatg agcatatgta aactgaagga    2280
tgtgtgagca gtattattga ttcttagatt ttagttggct gattagtttt ggccaatgaa    2340
cgcaagcatg tagttgccag tacaatgctt atcctgagat gagtattgag agtttttatt    2400
gtaaggaaca cagtgaagat tagtattgta aaaaaaaaaa aaaaaaaaaa aaaaaaa      2458
```

<210> SEQ ID NO 8
<211> LENGTH: 739
<212> TYPE: PRT
<213> ORGANISM: Nicotiana tabacum

<400> SEQUENCE: 8

```
Met Met Cys Gly Leu Ile Asp Leu Asn Thr Val Asp Asn Asp Asp Val
1               5                   10                  15

Gly Glu Glu Thr Thr Ala Pro Val Ser Pro Ala Ser Ser Ser Thr Ala
            20                  25                  30

Ser Gly Cys Ser Asp Leu Thr Ser Ser Ser Leu Pro Ala Met Ala Ser
        35                  40                  45

Val Cys Leu Glu Leu Trp His Ala Cys Ala Gly Pro Leu Ile Ser Leu
    50                  55                  60

Pro Lys Lys Gly Ser Ala Val Val Tyr Leu Pro Gln Gly His Leu Glu
65                  70                  75                  80

His Leu Ser Glu Tyr Pro Pro Ile Ala Tyr Asn Leu Pro Pro His Val
                85                  90                  95

Phe Cys Arg Val Val Asp Val Lys Leu Gln Ala Asp Ala Ala Ser Asp
            100                 105                 110

Glu Val Tyr Ala Gln Val Ser Leu Val Pro Asp Asn Gln Ile Glu Gln
        115                 120                 125

Lys Trp Arg Asp Gly Asp Ile Asp Ala Asp Thr Glu Glu Glu Glu Ile
    130                 135                 140

Glu Gly Ala Gly Lys Ser Thr Thr Pro His Met Phe Cys Lys Thr Leu
145                 150                 155                 160

Thr Ala Ser Asp Thr Ser Thr His Gly Gly Phe Ser Val Pro Arg Arg
                165                 170                 175

Ala Ala Glu Asp Cys Phe Pro Pro Leu Asp Tyr Arg Gln Gln Arg Pro
            180                 185                 190

Ser Gln Glu Leu Val Ala Lys Asp Leu His Gly Ile Glu Trp Lys Phe
        195                 200                 205

Arg His Ile Tyr Arg Gly Gln Pro Arg Arg His Leu Leu Thr Thr Gly
    210                 215                 220

Trp Ser Ala Phe Val Asn Arg Lys Lys Leu Val Ser Gly Asp Ala Val
225                 230                 235                 240

Leu Phe Leu Arg Thr Ala Asp Gly Glu Leu Arg Leu Gly Val Arg Arg
                245                 250                 255

Ala Ala Gln Ala Lys Thr Cys Ser Asn Tyr Leu Ala Ala Tyr Ser Gln
            260                 265                 270

Leu Leu Asn Val Ser Gly Ile Val Asp Val Val Lys Ala Ile Ser Ser
        275                 280                 285

Thr Asn Ala Phe Ser Ile Cys Tyr Asn Pro Arg Ala Ser Ser Ser Gly
```

-continued

```
            290                 295                 300

Phe Ile Leu Pro Tyr His Lys Phe Ser Lys Thr Leu Ala His Pro Phe
305                 310                 315                 320

Ser Ala Gly Met Arg Phe Lys Met Arg Val Glu Thr Glu Asp Ala Ala
                325                 330                 335

Glu Gln Arg Phe Thr Gly Leu Val Val Gly Val Ser Asp Val Asp Pro
                340                 345                 350

Val Arg Trp Pro Gly Ser Lys Trp Arg Cys Leu Leu Val Arg Trp Asp
                355                 360                 365

Asp Leu Asp Val Ser Arg His Asn Arg Val Ser Pro Trp Glu Ile Glu
            370                 375                 380

Pro Ser Gly Ser Ala Pro Val Ser Ser Leu Val Met Pro Ser Ala
385                 390                 395                 400

Lys Arg Thr Arg Val Gly Phe Pro Ile Thr Lys Ala Asp Phe Pro Ile
                405                 410                 415

Pro Arg Asp Gly Ile Ala Val Ser Asp Phe Gly Glu Ser Ser Arg Phe
                420                 425                 430

Gln Lys Val Leu Gln Gly Gln Glu Ile Leu Gly Ile Ser Ser Pro Phe
                435                 440                 445

Val Gly Phe Asp Ala His Ser Pro Arg Thr Ala Gly Ile Arg Cys Phe
            450                 455                 460

Pro Gly Phe Pro Ser Ser Gly Ala Ser Arg Leu Gly Asn Ser Ile Arg
465                 470                 475                 480

Thr Leu Leu Gly Asp Thr Asp Lys Ser Pro Glu Ser Ile Gly Phe Ser
                485                 490                 495

Asp Ser Ser Arg Tyr Asn Lys Val Leu Gln Gly Gln Glu Thr Phe Ser
                500                 505                 510

Thr Pro Pro Tyr Gly Arg Gly His Ala Gly Ser Leu Met Gln Glu Lys
                515                 520                 525

Ser Arg Thr Gly Ile Ile Val Gly Ile Gln Val Pro Ser His Val Asn
            530                 535                 540

Arg Trp Ser Ala Pro Asn Gln Gly Asn Arg Ser His Cys Asn Pro Ser
545                 550                 555                 560

Thr Leu Val Pro Ala Ser Ser Pro Pro Ser Val Leu Ser Phe Gln Pro
                565                 570                 575

Pro Arg Ser Pro Ala Ser Lys Phe Gln Ala Met Phe Asn His Lys His
                580                 585                 590

Gly Lys Leu Glu Thr Ala Thr Gln Ala Leu Asp Met Ser Glu Ser Cys
                595                 600                 605

Ser Arg His Leu Ala Ser Gly Ser His Ala Glu Asp Ile Ser Arg Lys
            610                 615                 620

Gly Asp Thr Lys Gly Ile Ser Ser Phe Ser Phe Leu Lys Glu Gln Lys
625                 630                 635                 640

Gln Thr Gly Ile Ser Tyr Leu Ser Leu Gly Thr Gln Ser Ser Gln Asn
                645                 650                 655

Leu Val Ser Met Cys Lys Thr Ser Cys Arg Ile Phe Gly Phe Pro Leu
                660                 665                 670

Thr Glu Ser Lys Ile Asn Ala Ala Arg Ala Glu Asn Pro Ala Glu Ala
                675                 680                 685

Val Tyr Ser His Gly Leu Glu Thr Thr Phe Leu Pro Ser Ser Asp Gly
            690                 695                 700

Lys Leu Gln Pro Gly Pro Leu Met Thr Asn Val Val Gly Thr Asn
705                 710                 715                 720
```

```
        Phe Thr Lys Val Asn Asp Leu Tyr Ala Ala Arg Asp Val Ile Leu Asp
                        725                 730                 735

Ile Ala Leu

<210> SEQ ID NO 9
<211> LENGTH: 22
<212> TYPE: DNA
<213> ORGANISM: Artificial
<220> FEATURE:
<223> OTHER INFORMATION: PCR primer

<400> SEQUENCE: 9
acatctgtaa ccggaacagc ac                                              22

<210> SEQ ID NO 10
<211> LENGTH: 22
<212> TYPE: DNA
<213> ORGANISM: Artificial
<220> FEATURE:
<223> OTHER INFORMATION: PCR primer

<400> SEQUENCE: 10
ggtcgtctat gtgtaagtca cc                                              22

<210> SEQ ID NO 11
<211> LENGTH: 33
<212> TYPE: DNA
<213> ORGANISM: Artificial
<220> FEATURE:
<223> OTHER INFORMATION: PCR primer

<400> SEQUENCE: 11
ttccacccaa gcagtggtat caacgcagag tgg                                  33

<210> SEQ ID NO 12
<211> LENGTH: 38
<212> TYPE: DNA
<213> ORGANISM: Artificial
<220> FEATURE:
<223> OTHER INFORMATION: PCR primer

<400> SEQUENCE: 12
gtatcgatgc ccaccctcta gaggccgagg cggccgac                             38

<210> SEQ ID NO 13
<211> LENGTH: 26
<212> TYPE: DNA
<213> ORGANISM: Artificial
<220> FEATURE:
<223> OTHER INFORMATION: PCR primer

<400> SEQUENCE: 13
ctatctccga cttctggtct tcctct                                          26

<210> SEQ ID NO 14
<211> LENGTH: 27
<212> TYPE: DNA
<213> ORGANISM: Artificial
<220> FEATURE:
<223> OTHER INFORMATION: PCR primer

<400> SEQUENCE: 14
ccacggtctc tgccttattc ctctgta                                         27
```

```
<210> SEQ ID NO 15
<211> LENGTH: 28
<212> TYPE: DNA
<213> ORGANISM: Artificial
<220> FEATURE:
<223> OTHER INFORMATION: PCR primer

<400> SEQUENCE: 15
acacatttgg tacaacagct ctaagtgc                                    28

<210> SEQ ID NO 16
<211> LENGTH: 28
<212> TYPE: DNA
<213> ORGANISM: Artificial
<220> FEATURE:
<223> OTHER INFORMATION: PCR primer

<400> SEQUENCE: 16
tgcaattgca tcaccaagaa gtgatgct                                    28

<210> SEQ ID NO 17
<211> LENGTH: 19
<212> TYPE: DNA
<213> ORGANISM: Artificial
<220> FEATURE:
<223> OTHER INFORMATION: PCR primer

<400> SEQUENCE: 17
cggggagttg gtgtagtag                                              19

<210> SEQ ID NO 18
<211> LENGTH: 27
<212> TYPE: DNA
<213> ORGANISM: Artificial
<220> FEATURE:
<223> OTHER INFORMATION: PCR primer

<400> SEQUENCE: 18 cctttttgtgt ctcccttcct actgatg                                    27

<210> SEQ ID NO 19
<211> LENGTH: 28
<212> TYPE: DNA
<213> ORGANISM: Artificial
<220> FEATURE:
<223> OTHER INFORMATION: PCR primer

<400> SEQUENCE: 19
ctaagttttg agagcactgg gtcccaag                                    28

<210> SEQ ID NO 20
<211> LENGTH: 38
<212> TYPE: DNA
<213> ORGANISM: Artificial
<220> FEATURE:
<223> OTHER INFORMATION: PCR primer

<400> SEQUENCE: 20
tctagaggat cccgggatgt gtggaggtgc cataatcc                         38

<210> SEQ ID NO 21
<211> LENGTH: 32
<212> TYPE: DNA
<213> ORGANISM: Artificial
<220> FEATURE:
<223> OTHER INFORMATION: PCR primer
```

<400> SEQUENCE: 21
gcgcccgggt tcagtaaaac agctgctgct gc                           32

<210> SEQ ID NO 22
<211> LENGTH: 28
<212> TYPE: DNA
<213> ORGANISM: Artificial
<220> FEATURE:
<223> OTHER INFORMATION: PCR primer

<400> SEQUENCE: 22
ggatccatga tgtgtggact tattgatc                                28

<210> SEQ ID NO 23
<211> LENGTH: 28
<212> TYPE: DNA
<213> ORGANISM: Artificial
<220> FEATURE:
<223> OTHER INFORMATION: PCR primer

<400> SEQUENCE: 23
cccgggctac aaagcaatat caagaatc                                28

<210> SEQ ID NO 24
<211> LENGTH: 31
<212> TYPE: DNA
<213> ORGANISM: Artificial
<220> FEATURE:
<223> OTHER INFORMATION: PCR primer

<400> SEQUENCE: 24
gcggtctaga cagatctgaa ttgatttgtc t                            31

<210> SEQ ID NO 25
<211> LENGTH: 32
<212> TYPE: DNA
<213> ORGANISM: Artificial
<220> FEATURE:
<223> OTHER INFORMATION: PCR primer

<400> SEQUENCE: 25
gcggtctaga acattattca gagctcacta tg                           32

<210> SEQ ID NO 26
<211> LENGTH: 30
<212> TYPE: DNA
<213> ORGANISM: Artificial
<220> FEATURE:
<223> OTHER INFORMATION: PCR primer

<400> SEQUENCE: 26
gcgtctagaa tgacggacta tagaatacca                              30

<210> SEQ ID NO 27
<211> LENGTH: 30
<212> TYPE: DNA
<213> ORGANISM: Artificial
<220> FEATURE:
<223> OTHER INFORMATION: PCR primer

<400> SEQUENCE: 27
gcgtctagat catcgcgatt cagcaattct                              30

<210> SEQ ID NO 28
<211> LENGTH: 21

```
<212> TYPE: DNA
<213> ORGANISM: Artificial
<220> FEATURE:
<223> OTHER INFORMATION: Northern probe sequence

<400> SEQUENCE: 28
acactgcact agcaccatcc c                                              21

<210> SEQ ID NO 29
<211> LENGTH: 22
<212> TYPE: DNA
<213> ORGANISM: Artificial
<220> FEATURE:
<223> OTHER INFORMATION: Northern probe sequence

<400> SEQUENCE: 29
ctgcattgta ctacgtacta cc                                             22

<210> SEQ ID NO 30
<211> LENGTH: 21
<212> TYPE: DNA
<213> ORGANISM: Artificial
<220> FEATURE:
<223> OTHER INFORMATION: Northern probe sequence

<400> SEQUENCE: 30
gaagtaacgg atactgaatg g                                              21

<210> SEQ ID NO 31
<211> LENGTH: 21
<212> TYPE: DNA
<213> ORGANISM: Artificial
<220> FEATURE:
<223> OTHER INFORMATION: Northern probe sequence

<400> SEQUENCE: 31
atccttgtgt ttgctgagaa t                                              21

<210> SEQ ID NO 32
<211> LENGTH: 20
<212> TYPE: DNA
<213> ORGANISM: Artificial
<220> FEATURE:
<223> OTHER INFORMATION: Northern probe sequence

<400> SEQUENCE: 32
ctgcctatag ccaactgttg                                                20

<210> SEQ ID NO 33
<211> LENGTH: 20
<212> TYPE: DNA
<213> ORGANISM: Artificial
<220> FEATURE:
<223> OTHER INFORMATION: Northern probe sequence

<400> SEQUENCE: 33
aagctgctgg atacaggagc                                                20

<210> SEQ ID NO 34
<211> LENGTH: 38
<212> TYPE: DNA
<213> ORGANISM: Artificial
<220> FEATURE:
<223> OTHER INFORMATION: PCR primer

<400> SEQUENCE: 34
```
gactgagctc tctagagtgg aggtgccata atccccga                              38

<210> SEQ ID NO 35
<211> LENGTH: 40
<212> TYPE: DNA
<213> ORGANISM: Artificial
<220> FEATURE:
<223> OTHER INFORMATION: PCR primer

<400> SEQUENCE: 35
gactcccggg gatatccggt ctctgcctta ttcctctgta                            40

<210> SEQ ID NO 36
<211> LENGTH: 35
<212> TYPE: DNA
<213> ORGANISM: Artificial
<220> FEATURE:
<223> OTHER INFORMATION: PCR primer

<400> SEQUENCE: 36
ggggagctct ctagagctgc aacagcgact ccaga                                 35

<210> SEQ ID NO 37
<211> LENGTH: 33
<212> TYPE: DNA
<213> ORGANISM: Artificial
<220> FEATURE:
<223> OTHER INFORMATION: PCR primer

<400> SEQUENCE: 37
cccggggtcg acccgttaac aaacgattga gtc                                   33

<210> SEQ ID NO 38
<211> LENGTH: 36
<212> TYPE: DNA
<213> ORGANISM: Artificial
<220> FEATURE:
<223> OTHER INFORMATION: PCR primer

<400> SEQUENCE: 38
ggggagctcg gatccgatgg gattgcagta tcagac                                36

<210> SEQ ID NO 39
<211> LENGTH: 36
<212> TYPE: DNA
<213> ORGANISM: Artificial
<220> FEATURE:
<223> OTHER INFORMATION: PCR primer

<400> SEQUENCE: 39
gggactagtg tcgacgagta cttggattgc aatgac                                36

<210> SEQ ID NO 40
<211> LENGTH: 38
<212> TYPE: DNA
<213> ORGANISM: Artificial
<220> FEATURE:
<223> OTHER INFORMATION: G2-Box probe sequence

<400> SEQUENCE: 40
agtagctgaa cacgttttat ttatggttgt tgaatagt                              38

<210> SEQ ID NO 41
<211> LENGTH: 38
<212> TYPE: DNA
<213> ORGANISM: Artificial

```
<220> FEATURE:
<223> OTHER INFORMATION: G2-Box probe sequence

<400> SEQUENCE: 41
actattcaac aaccataaat aaaacgtgtt cagctact                              38

<210> SEQ ID NO 42
<211> LENGTH: 38
<212> TYPE: DNA
<213> ORGANISM: Artificial
<220> FEATURE:
<223> OTHER INFORMATION: Mutated G2-box cold probe sequence

<400> SEQUENCE: 42
agtagctgaa tcacatttat ttatggttgt tgaatagt                              38

<210> SEQ ID NO 43
<211> LENGTH: 38
<212> TYPE: DNA
<213> ORGANISM: Artificial
<220> FEATURE:
<223> OTHER INFORMATION: Mutated G2-box cold probe sequence

<400> SEQUENCE: 43
actattcaac aaccataaat aaatgtgatt cagctact                              38
```

US 10,724,045 B2

TRANSCRIPTION FACTORS THAT REGULATE NICOTINE BIOSYNTHESIS IN TOBACCO

RELATED APPLICATION INFORMATION

This application is a divisional application of U.S. patent application Ser. No. 15/412,443, filed Jan. 23, 2017, which claims priority to U.S. Pat. No. 9,580,722, issued on Feb. 28, 2017, which claims the benefit of U.S. Provisional Application Ser. No. 61/771,526, filed Mar. 1, 2013, the disclosures of each of which are incorporated by reference herein in their entireties.

STATEMENT REGARDING ELECTRONIC FILING OF A SEQUENCE LISTING

A Sequence Listing in ASCII text format, submitted under 37 C.F.R. § 1.821, entitled 5051-826TS_ST25.txt, 37,572 bytes in size, generated on Feb. 20, 2014 and filed via EFS-Web, is provided in lieu of a paper copy. This Sequence Listing is hereby incorporated by reference into the specification for its disclosures.

FIELD OF THE INVENTION

The present invention relates to transcription factors and their use in modulation of nicotine biosynthesis in plants.

BACKGROUND OF THE INVENTION

Nicotine is found predominantly in the genus *Nicotiana* and in low quantities in some other species of the family Solanaceae (Sheen S J (1988) *J Food Science* 53: 1572-1573). Nicotine is the most abundant alkaloid in commercial tobacco (*N. tabacum* L.) cultivars (Siminszky et al. (2005) *Proc Natl Acad Sci USA* 102: 14919-14924), and naturally plays an important role in tobacco resistance to insect herbivores (Steppuhn et al (2004) *PLoS Biology* 2: 1074-1080). Nicotine is synthesized in tobacco root tip and transported to leaf and stored in leaf cell vacuole by a multidrug and toxic compound extrusion (MATE) transporter (Morita et al. (2009) *Proc Natl Acad Sci* 106: 2447-2452). The pathway for nicotine biosynthesis involves convergence of two biosynthetically distinct branches. The enzymes and the genes encoding these enzymes involved in the pathway have been identified except for the enzyme/gene that catalyzes the final condensation step of nicotinic acid and methyl-pyrrolinium cation to form nicotine, generally referred to as nicotine synthase. It has been proposed that a reduction reaction occurs followed by oxidation of nicotinic acid prior to formation of specific pyridine moiety that condenses with the methylpyrrolinium cation to form nicotine (Friesen and Leete (1990) *Tetrahedron Letters* 31:6295-6298). A622 and NBB1 have been proposed as catalysts of the final steps of nicotine biosynthesis (Hibi et al. (1994) *Plant Cell* 6:723-35: Shoji et al. (2002) *Plant Mol Biol* 50:427-440; Hashimoto and Kato 2007; Kajikawa et al. (2009) *Plant Mol Biol* 69: 287-298; Kajikawa et al. (2011) *Plant Physiol* 155(4):2010-22). Putrescine N-methyltransferase (PMT) and quinolinic acid phosphoribosyltransferase (QPT), the first committing enzymes in each branch of the nicotine biosynthetic pathway, are believed to be the key enzymes in nicotine production (Feth et al. (1986) *Planta* 168: 402-407; Wagner et al. (1986) *Physiol Plantarum* 68: 667-672). A few minor alkaloids, including nornicotine, anabasine, and anatabine, are also synthesized in this pathway, with nornicotine being directly converted from nicotine by nicotine demethylase whose corresponding genes have been cloned (Siminszky et al. (2005) *Proc Natl Acad Sci USA* 102: 14919-14924).

This invention addresses the need for compositions and methods that modulate the nicotine biosynthesis pathway in plants.

SUMMARY OF THE INVENTION

In one aspect, the present invention provides an isolated nucleic acid molecule comprising a nucleotide sequence is: (a) the nucleotide sequence of SEQ ID NO:1, SEQ ID NO:3, SEQ ID NO:5 or SEQ ID NO:7; (b) a nucleotide sequence that is at least 95% identical to the nucleotide sequence of (a) above; (c) a nucleotide sequence that encodes a transcription factor that modulates nicotine biosynthesis having the amino acid sequence of SEQ ID NO:2, SEQ ID NO:4, SEQ ID NO:6 or SEQ ID NO:8; (d) a nucleotide sequence that differs from the nucleotide sequence of (a), (b) or (c) above due to the degeneracy of the genetic code: (e) a nucleotide sequence which anneals under stringent hybridization conditions to the nucleotide sequence of (a), (b), (c) or (d) above, or a complement thereof: or (f) any combination of the nucleotide sequences of (a)-(e) above.

In a second aspect, a nucleic acid construct is provided, the nucleic acid construct comprising in the 5' to 3' direction, a promoter operable in a plant cell and a nucleic acid molecule of the invention positioned downstream from said promoter and operatively associated therewith. In some aspects, the nucleic acid molecule is positioned in the sense direction and in other aspects the nucleic acid molecule is positioned in the antisense direction.

In a third aspect, a nucleic acid construct comprising double stranded RNA molecule comprising an antisense strand and a sense strand is provided, wherein the nucleotide sequence of the antisense strand is complementary to a portion of a nucleic acid molecule of the invention.

In an additional aspect, a method of identifying a plant having a mutation in a gene encoding a transcription factor that modulates nicotine biosynthesis is provided, comprising screening a population of plants by high-throughput DNA sequence analysis using primers comprising one or more portions of SEQ ID NO:1, SEQ ID NO:3, SEQ ID NO:5 and/or SEQ ID NO:7, and or by TILLING (Targeting Induced Local Lesions In Genomes) using a probe comprising SEQ ID NO:1, SEQ ID NO:3, SEQ ID NO:5 and/or SEQ ID NO:7 or a portion of SEQ ID NO:1, SEQ ID NO:3, SEQ ID NO:5 and/or SEQ ID NO:7, thereby identifying a plant having a mutation in a gene encoding a transcription factor that modulates nicotine biosynthesis.

A further aspect of the invention provides a method of producing a plant having a mutation in a gene encoding a transcription factor that modulates nicotine biosynthesis, comprising targeted mutagenesis using a reagent comprising a nucleic acid consisting of a portion of SEQ ID NO:1, SEQ ID NO:3, SEQ ID NO:5 and/or SEQ ID NO:7.

A further aspect of the invention provides a nucleic acid construct comprising in the 5' to 3' direction, a plant promoter and a nucleic acid molecule of the invention or a fragment thereof positioned downstream from said promoter and operatively associated therewith, said nucleic acid molecule in antisense orientation.

In an additional aspect, a method of identifying a plant having a mutation in a gene encoding a transcription factor that modulates (e.g., regulates) nicotine biosynthesis is provided, comprising screening a population of plants by high-throughput DNA sequence analysis using primers comprising one or more portions of SEQ ID NO:1, SEQ ID NO:3, SEQ ID NO:5 and/or SEQ ID NO:7, and/or by TILLING (Targeting Induced Local Lesions In Genomes) using a probe comprising SEQ ID NO:1, SEQ ID NO:3, SEQ ID NO:5 and/or SEQ ID NO:7 or a portion of SEQ ID NO:1, SEQ ID NO:3, SEQ ID NO:5 and/or SEQ ID NO:7, thereby identifying a plant having a mutation in a gene encoding a transcription factor that modulates (e.g., regulates) nicotine biosynthesis.

A further aspect of the invention provides a method of producing a plant having a mutation in a gene encoding a transcription factor that modulates nicotine biosynthesis, comprising targeted mutagenesis using a reagent comprising a nucleic acid consisting of a portion of SEQ ID NO:1, SEQ ID NO:3, SEQ ID NO:5 and/or SEQ ID NO:7, thereby producing a plant having a mutation in a gene encoding a transcription factor that modulates nicotine biosynthesis.

The present invention further provides vectors and expression cassettes comprising at least one nucleic acid construct of the invention.

In still other aspects, the present invention provides a method of producing a plant having modulated nicotine content, comprising introducing into a plant cell a nucleic acid construct of the invention to produce a transgenic plant cell comprising said nucleic acid construct; and regenerating said transgenic plant cell to produce a transgenic plant comprising said nucleic acid construct. In some aspects, the plant is a tobacco plant.

In an additional aspect, a method of modulating nicotine content in a plant is provided, the method comprising introducing into a plant cell a nucleic acid construct of the present invention to produce a transgenic plant cell comprising said nucleic acid construct; and regenerating said transgenic plant cell to produce a transgenic plant comprising said nucleic acid construct, thereby modulating nicotine production in said transgenic plant. In aspects, the plant is a tobacco plant.

The present invention further provides bacterial cells, plants and plant parts thereof comprising at least one nucleic acid construct of the invention as well as well as crops and products produced from said plants and parts thereof.

These and other aspects of the invention are set forth in more detail in the description of the invention below.

DETAILED DESCRIPTION OF THE INVENTION

Figure 1:
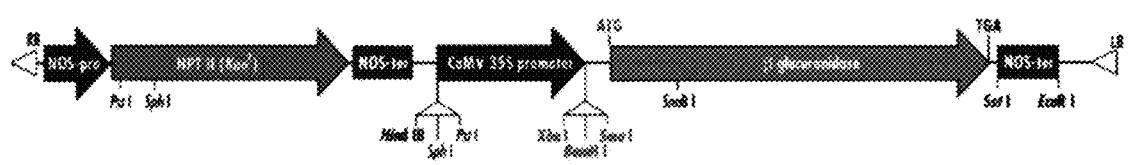
FIG. 1 shows a vector map of T-DNA region of pBI121.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A. B or C, or a combination thereof, can be omitted and disclaimed singularly or in any combination.

As used in the description of the invention and the appended claims, the singular forms "a." "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, refers to variations of ±20%, ±10%, ±5%, ±1%, ±0.5%, or even ±0.1%6 of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

Nicotine biosynthesis occurs predominantly in the roots of tobacco plants (Dawson R F (1941) *Science* 94 (2443): 396-397: Dawson R F (1942) *American Journal of Botany* 29(10):813-815). The cortex and epidermis of the differentiated region of the root tip is considered the site of nicotine production. The plant then transports the alkaloids through the vascular bundle to the leaves where the alkaloids are then stored in the vacuoles (Shoji et al. (2000) *Plant & Cell Physiol* 41: 831-839. Shoji et al. (2002) *Plant Mol Biol* 50: 427-440: Katoh et al. (2005) *Plant Biotechnology* 22: 389-392.). Several transporters may be involved in the translocation process. A transporter gene, named MATE, has recently been cloned and characterized (Morita et al. (2009) *Proc Natl Acad Sci (USA)* 106: 2447-2452).

Biotic and abiotic stresses, such as herbivore damage, topping (decapitation of the apical meristem at an early stage of flowering) and suckering (removing the axillary buds of plants activated by topping) can significantly increase nicotine accumulation in tobacco leaf (Baldwin I T (1988) *Oecologia* 77: 378-381: Wang et al. (2008) *Nico J Integr Plant Biol* 50: 958-964). Nicotine biosynthesis and accumulation is mediated by endogenous phytohormone changes, which affect expression of the genes involved in nicotine biosynthesis. So far, jasmonic acid (JA), ethylene, auxin and abscisic acid (ABA) have been shown to affect nicotine biosynthesis (Shoji et al. (2000) *Plant Cell Physiol* 41: 1072-1076; Shi et al. (2006) *J Exp Bot* 57: 2899-2907; Lackman et al. (2011) *Proc Natl Acad Sci USA* 108: 5891-5896).

Nicotine production stimulated by JA treatment is well documented. Major nicotine biosynthetic pathway genes, including putrescine N-methyltransferase gene (NtPMT), quinolinic acid phosphoribosyltransferase gene (NtQPT), ornithine decarboxylase gene (NtODC), Arginine decarboxylase gene (NtADC), N-methylputrescine oxidase gene (NtMPO), an isoflavone reductase-like gene (NtA622) and a berberine bridge enzyme-like gene (NtBBL) have been shown to be up-regulated to various extents by MeJA application (Cane et al. (2005) *Functional Plant Biology* 32: 305; Katoh et al. (2007) *Plant Cell Physiol* 48: 550-554; U.S. Patent Application Publication 20070240728). Stimulation of nicotine production by MeJA or wounding in tobacco is mediated by the JA signaling pathway similar to that in *Arabidopsis*. Both NtCOI1 (Coronatine Insensitive 1) expression and NtJAZ (Jasmonate Zim) protein degradation are required for nicotine biosynthesis (Shoji et al. (2008) *Plant Cell Physiol* 49: 1003-1012).

Major steps in nicotine biosynthetic pathway have been elucidated in the past two decades or so. However, studies on the regulation of this pathway at the transcription level have only begun recently. A tobacco transcription factor database has been established based on in silico analysis of genomic sequencing data. More than 2500 transcription factors from 64 families were identified (Rushton et al. (2008) *Plant Physiol* 147: 280-295). However, which transcription factors are involved in nicotine biosynthesis and how those transcription factors function together to regulate nicotine biosynthetic pathway has remained unclear.

Genetic controls influence the type and level of alkaloids observed in *Nicotiana tabacum*. In one system, two unlinked genetic loci, Nic1 and Nic2 (or A and B), have been shown to control the total alkaloid accumulation. Nic1 and Nic2 have different dosage effects on alkaloid accumulation. Nic1 (A) has 2.4-fold greater activity than Nic2 (B) and their effects are additive (Legg and Collins (1971) *Can. J. Genet. Cytol* 13: 287-291). Commercial varieties with high total alkaloid content are considered as homozygous dominant (AABB) at these two loci and low alkaloid level genotypes are considered as homozygous recessive (aabb) at these two loci. Under this genetic model, nine genotypes of tobacco plants with different levels of total alkaloids were developed (Legg et al. (1969) *J. Hered* 60: 213-217; Legg and Collins (1971) *Can. J. Genet. Cytol* 13: 287-291). Very recently, the Nic2 locus has been molecularly characterized. It is actually a cluster of transcription factor genes from the ethylene responsive factor (ERF) family. They regulate nicotine biosynthetic pathway genes (Shoji et al. (2010) *The Plant Cell* 22: 3390-3409).

Another system controls the types of alkaloids produced and has a genetic locus which controls the conversion of nicotine to nomicotine. When both alleles of this locus are recessive, the plant contains predominantly nicotine. If one or both alleles are dominant, the plant primarily produces nomicotine. Nomicotine results from demethylation of nicotine (Mann et al. (1964) *Crop Sci.* 4:349-353). The gene encoding nicotine demethylase, a cytochrome P450 gene, CYP82E4, was cloned and characterized (Siminszky et al. (2005) *Proc Natl Acad Sci (USA)* 102: 14919-14924)). Suppressing the expression of this gene resulted in a drastic reduction in nomicotine content (Lewis et al. (2008) *Plant Biotechnology Journal* 6: 346-354).

In addition to the two genetic systems described above, some minor or quantitative factors are involved in alkaloid synthesis. Therefore, it is possible to produce tobacco lines with varying alkaloid content within the range of the parents' alkaloid levels (Matzinger et al. (1972) *Crop Sci.* 12: 40-43, Matzinger et al. (1989) *Crop Sci.* 29: 74-77).

The low nicotine content trait has been of interest to tobacco breeders. LA Burley 21 is a low total alkaloid line produced by incorporation of a low alkaloid gene(s) from a Cuban cigar variety into Burley 21 through several backcrosses (Legg et al. (1970) *Crop Sci* 10: 212. It has approximately 0.2% total alkaloids (dry weight) compared to the 3.5% (dry weight) of its parent, Burley 21. Similarly, Chaplin and Burk (*Agronomy Journal* 75: 133-136 (1983)) developed some flue-cured tobacco lines with different alkaloid levels by backcrossing. They used NC95, SC58, and Coker 139 as recurrent parent lines and crossed them with LAFC 53 (a low total alkaloid line in NC95 background) followed by several backcrosses. Five different alkaloid levels were obtained from the NC95 family, six from the SC58 family, and four from the Coker139 family.

However, the breeding of commercial tobacco cultivars is more complicated than simply focusing on the alkaloid content in leaf. It has been found that alkaloid accumulation is genetically linked with other important agronomic traits. For example, a reverse correlation exists between total alkaloids and yield. Selection for increased yield may result in reduced level of total alkaloids (Chaplin and Week (1976) *Crop Sci* 16: 416-418). Conventional breeding methods have not been very efficient at breaking this close genetic relationship. It is believed that genetic manipulation at the molecular level may meet this need of tobacco breeders by only modifying alkaloid accumulation without affecting other traits such as yield.

The present invention provides compositions and methods for the genetic manipulation of alkaloid accumulation, more particularly nicotine accumulation, in plants. Thus, in one aspect the present invention provides an isolated nucleic acid molecule comprising a nucleotide sequence is: (a) the nucleotide sequence of SEQ ID NO:1, SEQ ID NO:3, SEQ ID NO:5, SEQ ID NO:7; (b) a nucleotide sequence that is at least 95% identical to the nucleotide sequence of (a) above; (c) a nucleotide sequence that encodes a transcription factor that modulates nicotine biosynthesis having the amino acid sequence of SEQ ID NO:2, SEQ ID NO:4, SEQ ID NO:6 or SEQ ID NO:8; (d) a nucleotide sequence that differs from the nucleotide sequence of (a), (b) or (c) above due to the degeneracy of the genetic code and that encodes a transcription factor that modulates nicotine biosynthesis; (e) a nucleotide sequence which anneals under stringent hybridization conditions to the nucleotide sequence of (a), (b), (c) or (d) above, or a complement thereof; or (1) any combination of the nucleotide sequences of (a)-(e) above. The nucleic acid molecules of the invention (the nucleotide sequences of SEQ ID NO:1 (NtMYC2a cDNA), SEQ ID NO:3 (NtMYC2b cDNA), SEQ ID NO:5 (NtERF98 cDNA), and SEQ ID NO:7 (NtETTa cDNA)) encode transcription factors that modulate nicotine biosynthesis, their respective amino acid sequences being SEQ ID NO:2 (NtMYC2a), SEQ ID NO:4 (NtMYC2b), SEQ ID NO:6 (NtERF98) and SEQ ID NO:8 (NtETTa).

Thus, overexpression or reduced expression of an isolated nucleic acid molecule or a nucleic acid construct described herein can result in the plant having increased or decreased nicotine content (as compared to a wild type plant or a plant that does not comprise said isolated nucleic acid molecule or said nucleic acid construct). Thus, in one aspect, the invention provides a recombinant nucleic acid molecule comprising one or more (e.g., 1, 2, 3, 4, 5, 6, 7, 8, 9, 10, 11, 12, 13, 14, 15, and the like) nucleotide sequences, each of which when expressed in a plant confer increased or decreased nicotine content on said plant, wherein the one or more nucleotide sequences comprise, consist essentially of, or consist of: (a) the nucleotide sequence of SEQ ID NO:1, SEQ ID NO:3, SEQ ID NO:5 and/or SEQ ID NO:7: (b) a nucleotide sequence that is at least 95% identical to the nucleotide sequence of (a) above: (c) a nucleotide sequence that encodes a transcription factor that modulates nicotine biosynthesis having the amino acid sequence of SEQ ID NO:2, SEQ ID NO:4, SEQ ID NO:6 and/or SEQ ID NO:8: (d) a nucleotide sequence that differs from the nucleotide sequence of (a), (b) or (c) above due to the degeneracy of the genetic code and that encodes a transcription factor that modulates nicotine biosynthesis; (e) a nucleotide sequence which anneals under stringent hybridization conditions to the nucleotide sequence of (a), (b), (c) or (d) above, or a complement thereof, or (f) any combination of the nucleotide sequences of (a)-(e) above.

The nucleic acid molecules/transcription factors of the present invention can be comprised in any construct useful for modulating or altering nicotine content in an organism expressing said transcription factors. Thus, for example, transcription factors of the invention can be comprised in antisense constructs, RNAi constructs and the like.

Accordingly, in one embodiment, the present invention provides nucleic acid construct comprising in the 5' to 3' direction, a promoter operable in a plant cell and the nucleic acid molecule of the invention positioned downstream from said promoter and operatively associated therewith. In some embodiments, the nucleic acid molecule is positioned in the sense direction. In other embodiments, the nucleic acid molecule is positioned in the antisense direction. In some embodiments, the promoter can be a heterologous promoter.

In a still further embodiment, the present invention provides an RNAi construct comprising, consisting essentially of, or consisting of a nucleic acid molecule of the invention. Thus, in some embodiments, a nucleic acid construct comprising double stranded RNA molecule comprising an antisense strand and a sense strand is provided, wherein the nucleotide sequence of the antisense strand is complementary to a portion of the nucleic acid molecule of the invention. In some embodiments, the portion of the nucleic acid molecule of the invention comprises, consists essentially or consists of about 18 to about 1000 consecutive nucleotides of said nucleic acid molecule, wherein the double stranded RNA molecule inhibits expression of a transcription factor of the invention (e.g., nucleotide sequence of SEQ ID NO:1, SEQ ID NO:3, SEQ ID NO:5 and/or SEQ ID NO:7) Thus, in some embodiments, the portion of the nucleic acid molecule of the invention to which the antisense strand is complementary comprises, consists essentially or consists of about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nucleotides and the like or any range therein. Thus, in some embodiments, the portion can be about 18 to about 25 consecutive nucleotides of said nucleic acid molecule, or any range therein. In other embodiments, the portion can be about 75 to about 1000 consecutive nucleotides of said nucleic acid molecule, or any range therein. In still other embodiments, the portion can be about 95 to about 900 consecutive nucleotides of said nucleic acid molecule, or any range therein. In an additional embodiment, the portion can be about 100 to about 500 consecutive nucleotides of said nucleic acid molecule, or any range therein. Thus, in some embodiments, the dsRNA can comprise two identical (self-complementary) fragments of varying length (e.g., about 75 to about 900 contiguous nucleotides, or any range therein) of the target gene with a spacer in between (see. e.g., FIG. 2), which then forms a hairpin and can be cleaved into smaller pieces that can then act to inhibit expression of the target gene. In some embodiments, the spacer can be an intron (see. e.g., Wesley et al. *Plant J* 27(6):581-590 (2002).

Thus, in some embodiments, the RNAi construct produces a siRNA or miRNA. In other embodiments, the RNAi construct can be a short hairpin RNA (shRNA). In still other embodiments, the RNAi construct can be a hairpinRNA (hpRNA) construct. Methods for making such constructs are well known in the art (see. e.g., Wesley et al. *Plant J* 27(6):581-590 (2002)).

In a further embodiment, the present invention provides a nucleic acid construct comprising in the 5' to 3' direction, a plant promoter and a nucleic acid molecule of the invention or a fragment thereof positioned downstream from said promoter and operatively associated therewith, said nucleic acid molecule in antisense orientation. A fragment of a nucleic acid molecule of the invention can be about 10 consecutive nucleotides to the full size of the nucleic acid molecule (e.g., about 2500 bp). Thus, a fragment of a nucleic acid molecule of the invention can be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 310, 320, 330, 340, 350, 360, 370, 380, 390, 400, 410, 420, 430, 440, 450, 460, 470, 480, 490, 500), 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500 nucleotides and the like or any range therein.

In some embodiments of the invention, nucleotide sequences having significant sequence identity to the nucleotide sequences of the invention are provided. "Significant sequence identity" or "significant sequence similarity" means at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100% identity or similarity with another nucleotide sequence. Thus, in additional embodiments, "significant sequence identity" or "significant sequence similarity" means a range of about 70% to about 100%, about 75% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, and/or about 99% to about 100% identity or similarity with another nucleotide sequence. Therefore, in some embodiments, a nucleotide sequence of the invention is a nucleotide sequence that has significant sequence identity to the nucleotide sequence of any of SEQ ID NO:1, SEQ ID NO:3, SEQ ID NO:5, and/or SEQ ID NO:7.

In some embodiments, a polypeptide of the invention comprises, consists essentially of, or consists of an amino acid sequence that is at least 70% identical, e.g., at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100% identical to an amino acid sequence of any of SEQ ID NO:2, SEQ ID NO:3, SEQ ID NO:6, and/or SEQ ID NO:8.

In some embodiments, a polypeptide or nucleotide sequence of the invention can be a conservatively modified variant. As used herein, "conservatively modified variant" refer to polypeptide and nucleotide sequences containing individual substitutions, deletions or additions that alter, add or delete a single amino acid or nucleotide or a small percentage of amino acids or nucleotides in the sequence, where the alteration results in the substitution of an amino acid with a chemically similar amino acid. Conservative substitution tables providing functionally similar amino acids are well known in the art.

As used herein, a conservatively modified variant of a polypeptide is biologically active and therefore possesses the desired activity of the reference polypeptide (e.g., transcription factor activity: reducing or increasing the nicotine content in a plant) as described herein. The variant can result from, for example, a genetic polymorphism or human manipulation. A biologically active variant of the reference polypeptide can have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity or similarity (e.g., about 40% to about 99% or more sequence identity or similarity and any range therein) to the amino acid sequence for the reference polypeptide as determined by sequence alignment programs and parameters described elsewhere herein. An active variant can differ from the reference polypeptide sequence by as few as 1-15 amino acid residues, as few as 1-10, such as 6-10, as few as 5, as few as 4, 3, 2, or even 1 amino acid residue.

Naturally occurring variants may exist within a population. Such variants can be identified by using well-known molecular biology techniques, such as the polymerase chain reaction (PCR), and hybridization as described below. Synthetically derived nucleotide sequences, for example, sequences generated by site-directed mutagenesis or PCR-mediated mutagenesis which still encode a polypeptide of the invention, are also included as variants. One or more nucleotide or amino acid substitutions, additions, or deletions can be introduced into a nucleotide or amino acid sequence disclosed herein, such that the substitutions, additions, or deletions are introduced into the encoded protein. The additions (insertions) or deletions (truncations) may be made at the N-terminal or C-terminal end of the native protein, or at one or more sites in the native protein. Similarly, a substitution of one or more nucleotides or amino acids may be made at one or more sites in the native protein.

For example, conservative amino acid substitutions may be made at one or more predicted, preferably nonessential amino acid residues. A "nonessential" amino acid residue is a residue that can be altered from the wild-type sequence of a protein without altering the biological activity, whereas an "essential" amino acid is required for biological activity. A "conservative amino acid substitution" is one in which the amino acid residue is replaced with an amino acid residue with a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, where such residues are essential for protein activity.

For example, amino acid sequence variants of the reference polypeptide can be prepared by mutating the nucleotide sequence encoding the enzyme. The resulting mutants can be expressed recombinantly in plants, and screened for those that retain biological activity by assaying for increased or reduced nicotine content using standard assay techniques as described herein. Methods for mutagenesis and nucleotide sequence alterations are known in the art. See, e.g., Kunkel (1985) *Proc. Natl. Acad. Sci. USA* 82:488-492; Kunkel et al. (1987) *Methods in Enzymol.* 154:367-382; and *Techniques in Molecular Biology* (Walker & Gaastra eds., MacMillan Publishing Co. 1983) and the references cited therein; as well as U.S. Pat. No. 4,873,192. Clearly, the mutations made in the DNA encoding the variant must not disrupt the reading frame and preferably will not create complimentary regions that could produce secondary mRNA structure. See, EP Patent Application Publication No. 75,444. Guidance as to appropriate amino acid substitutions that do not affect biological activity of the protein of interest may be found in the model of Dayhoff et al. (1978) *Atlas of Protein Sequence and Structure* (National Biomedical Research Foundation, Washington, D.C.), herein incorporated by reference.

The deletions, insertions and substitutions in the polypeptides described herein are not expected to produce radical changes in the characteristics of the polypeptide (e.g., the activity of the polypeptide). However, when it is difficult to predict the exact effect of the substitution, deletion or insertion in advance of doing so, one of skill in the art will appreciate that the effect can be evaluated by routine screening assays that can screen for the particular polypeptide activities of interest (e.g., conferring increased or reduced nicotine content to a plant).

In some embodiments, the compositions of the invention can comprise active fragments of the polypeptide. As used herein, "fragment" means a portion of the reference polypeptide that retains the polypeptide activity of conferring increased or decreased nicotine content in a plant. A fragment also means a portion of a nucleic acid molecule encoding the reference polypeptide. An active fragment of the polypeptide can be prepared, for example, by isolating a portion of a polypeptide-encoding nucleic acid molecule that is expressed to produce the encoded fragment of the polypeptide (e.g., by recombinant expression in vitro), and assessing the activity of the fragment. Nucleic acid molecules encoding such fragments can be at least about 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900, 2000, 2100, 2200, 2400 or 2500, contiguous nucleotides, or up to the number of nucleotides present in a full-length polypeptide-encoding nucleic acid molecule. As such, polypeptide fragments can be at least about 50, 60, 70, 80, 90, 100, 125, 150, 175, 200, 225, 250, 275, 300, 325, 350, 375, 400, 425, 450, 475, 500, 525, 550, 525, 550, 600, 625, 650, 675, 700, 725, 750, or 800 contiguous amino acid residues, or up to the total number of amino acid residues present in the full-length polypeptide.

Thus, in some embodiments, a variant or functional fragment of a polypeptide of this invention or a variant or functional fragment having substantial identity to a polypeptide sequence of this invention (e.g., SEQ ID NO:2, SEQ ID NO:3, SEQ ID NO:6, SEQ ID NO:8) when introduced into and expressed in a transgenic plant reduces or increases the nicotine content of the transgenic plant producing said polypeptides.

As used herein, the terms "express," "expresses," "expressed" or "expression." and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or a functional untranslated RNA.

A "heterologous" or "exogenous" nucleotide sequence is a nucleotide sequence not naturally associated with a host cell into which it is introduced, including non-naturally occurring multiple copies of a naturally occurring nucleotide sequence. Alternatively, a heterologous nucleotide sequence can be one that does not naturally occur with another nucleotide sequence to which it is associated. For example, a nucleic acid construct comprising a "heterologous promoter" operably associated with a nucleic acid molecule is a promoter that does not naturally occur with said nucleic acid molecule to which it is associated.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule." "nucleotide sequence" and "polynucleotide" can be used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

The term "antisense nucleotide sequence" or "antisense oligonucleotide" as used herein, refers to a nucleotide sequence that is complementary to a specified DNA or RNA sequence. Antisense oligonucleotides and nucleic acids that express the same can be made in accordance with conventional techniques. See, e.g., U.S. Pat. No. 5,023,243 to Tullis; U.S. Pat. No. 5,149,797 to Pederson et al. The antisense nucleotide sequence can be complementary to the entire nucleotide sequence encoding the polypeptide or a portion thereof of at least 10, 20, 40, 50, 75, 100, 150, 200, 250, 300, 350, 400, 450, 500, 550, 600, 650, 700, 750, 800, 850, 900, 950, 1000 or more contiguous bases and will reduce the level of polypeptide production.

Those skilled in the art will appreciate that it is not necessary that the antisense nucleotide sequence be fully complementary to the target sequence as long as the degree of sequence similarity is sufficient for the antisense nucleotide sequence to hybridize to its target and reduce production of the polypeptide or transcript. As is known in the art, a higher degree of sequence similarity is generally required for short antisense nucleotide sequences, whereas a greater degree of mismatched bases will be tolerated by longer antisense nucleotide sequences.

For example, hybridization of such nucleotide sequences can be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and/or conditions represented by a wash stringency of 50% formamide with 5×Denhardt's solution, 0.5% SDS and 1×SSPE at 42° C., respectively) to the nucleotide sequences specifically disclosed herein. See. e.g., Sambrook et al., Molecular Cloning: A Laboratory Manual 2nd Ed. (Cold Spring Harbor, N.Y., 1989).

In other embodiments, antisense nucleotide sequences of the invention have at least about 70%, 80%, 90%, 95%, 97%, 98% or higher sequence similarity with the complement of the coding sequences specifically disclosed herein and will reduce the level of polypeptide production.

The length of the antisense nucleotide sequence (i.e., the number of nucleotides therein) is not critical as long as it binds selectively to the intended location and reduces transcription and/or translation of the target sequence, and can be determined in accordance with routine procedures. In general, the antisense nucleotide sequence will be from about eight, ten or twelve nucleotides in length to about 20, 30, 50, 75, 100, 150, 200, 250, 300, 350, 400, 450, 500, 550, 600, 650, 700, 750, 800, 850, 900, 950, 1000 nucleotides, or longer, in length.

An antisense nucleotide sequence can be constructed using chemical synthesis and enzymatic ligation reactions by procedures known in the art. For example, an antisense nucleotide sequence can be chemically synthesized using naturally occurring nucleotides or various modified nucleotides designed to increase the biological stability of the molecules or to increase the physical stability of the duplex formed between the antisense and sense nucleotide sequences. e.g., phosphorothioate derivatives and acridine substituted nucleotides can be used. Examples of modified nucleotides which can be used to generate the antisense nucleotide sequence include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethyl-aminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine. N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleotide sequence can be produced using an expression vector into which a nucleic acid has been cloned in an antisense orientation (i.e., RNA transcribed from the inserted nucleic acid will be of an antisense orientation to a target nucleic acid of interest).

The antisense nucleotide sequences of the invention further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the antisense nucleotide sequence is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., *Nucleic Acids Res.* 17:9193 (1989): Agrawal et al., *Proc. Natl. Acad. Sci. USA* 87:1401 (1990); Baker et al., *Nucleic Acids Res.* 18:3537 (1990); Sproat et al., *Nucleic Acids Res.* 17:3373 (1989); Walder and Walder, *Proc. Natl. Acad. Sci. USA* 85:5011 (1988); incorporated by reference herein for their teaching of methods of making antisense molecules, including those containing modified nucleotide bases).

Triple helix base-pairing methods can also be employed to inhibit production of polypeptides of this invention (e.g., SEQ ID NO:2, SEQ ID NO:4, SEQ ID NO:6 and/or SEQ ID NO:8). Triple helix pairing is believed to work by inhibiting the ability of the double helix to open sufficiently for the binding of polymerases, transcription factors, or regulatory molecules. Recent therapeutic advances using triplex DNA have been described in the literature (e.g., Gee et al., (1994) In: Huber et al., Molecular and Immunologic Approaches, Futura Publishing Co., Mt. Kisco, N.Y.).

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of this invention has a significant sequence identity (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to the nucleotide sequences of the invention.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part* 1 (Griffin, A. M., and Griffin, H. G., eds.) Humana Press, New Jersey (1994); *Sequence Analysis in Molecular Biology* (von Heinje, G., ed.) Academic Press (1987), and *Sequence Analysis Primer* (Gribskov, M, and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 95%, at least about 96%, at least about 97%, at least about 98%, or at least about 99% nucleotide or amino acid residue identity, w en compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of the invention, the substantial identity exists over a region of the sequences that is at least about 50, about 60, about 70, about 80, about 90, about 100, about 110, about 120, about 130, about 140, about 150, or more residues in length. In some particular embodiments, the sequences are substantially identical over at least about 150 residues. In a further embodiment, the sequences are substantially identical over the entire length of the coding regions. Furthermore, in representative embodiments, substantially identical nucleotide or protein sequences perform substantially the same function (e.g., modulating nicotine content).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues: always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see. e.g., Karlin & Altschul, Proc. Nat'l. Acad Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see. Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1%6 SDS at 50° C., or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

In particular embodiments, a further indication that two nucleotide sequences or two polypeptide sequences are substantially identical can be that the protein encoded by the first nucleic acid is immunologically cross reactive with, or specifically binds to, the protein encoded by the second nucleic acid. Thus, in some embodiments, a polypeptide can be substantially identical to a second polypeptide, for example, where the two polypeptides differ only by conservative substitutions.

An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a nonnative environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In some embodiments, the nucleotide sequences and/or nucleic acid molecules of the invention can be operatively associated with a variety of promoters for expression in host cells (e.g., plant cells). Thus, in some embodiments, the invention provides transformed host cells and transformed organisms comprising the transformed host cells, wherein the host cells and organisms are transformed with one or more nucleic acid molecules/nucleotide sequences of the invention. As used herein, "operatively associated with," when referring to a first nucleic acid sequence that is operatively linked to a second nucleic acid sequence, means a situation when the first nucleic acid sequence is placed in a functional relationship with the second nucleic acid sequence. For instance, a promoter is operatively associated with a coding sequence if the promoter effects the transcription or expression of the coding sequence.

A promoter can be any promoter useful for expression of nucleic acids in plants and as described herein. In some embodiments, the promoter can be a constitutive promoter. In other embodiments, it can be a tissue preferred promoter or a tissue specific promoter.

A DNA "promoter" is an untranslated DNA sequence upstream of a coding region that contains the binding site for RNA polymerase and initiates transcription of the DNA. A "promoter region" can also include other elements that act as regulators of gene expression. Promoters can include, for example, constitutive, inducible, temporally regulated, developmentally regulated, chemically regulated, tissue-preferred and tissue-specific promoters for use in the preparation of recombinant nucleic acid molecules, i.e., chimeric genes. In particular aspects, a "promoter" useful with the invention is a promoter capable of initiating transcription of a nucleotide sequence in a cell of a plant.

The choice of promoter will vary depending on the temporal and spatial requirements for expression, and also depending on the host cell to be transformed. Thus, for example, expression of the nucleotide sequences of the invention can be in any plant and/or plant part, (e.g., in leaves, in stalks or stems, in ears, in inflorescences, in roots, seeds and/or seedlings, and the like).

Promoters useful with the invention include, but are not limited to, those that drive expression of a nucleotide sequence constitutively, those that drive expression when induced, and those that drive expression in a tissue- or developmentally-specific manner. These various types of promoters are known in the art.

Examples of constitutive promoters include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant 5 Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and arabidopsis (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used. Tissue specific or preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121: the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in WO 01/73087, all incorporated by reference Additional examples of tissue-specific/tissue preferred promoters include, but are not limited to, the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200). Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022: Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger el al. (1991) *Genetics* 129:863-872), α-tubulin cab promoter (Sullivan et al. (1989) Mol. Gen. Genet. 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612). In some particular embodiments, the nucleotide sequences of the invention are operatively associated with a root-preferred promoter.

Particularly useful for seed-specific expression is the pea vicilin promoter (Czako et al. (1992) *Mol. Gen. Genet.* 235:33-40: as well as the seed-specific promoters disclosed in U.S. Pat. No. 5,625,136. Useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see. e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see. e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

In further aspects, the nucleotide sequences of the invention can be operatively associated with a promoter that is wound inducible or inducible by pest or pathogen infection. Numerous promoters have been described which are expressed at wound sites and/or at the sites of pest attack or phytopathogen infection. Ideally, such a promoter should be active only locally at or adjacent to the sites of attack, and in this way expression of the nucleotide sequences of the invention will be focused in the cells that are being invaded. Such promoters include, but are not limited to, those described by Stanford et al., *Mol. Gen. Genet.* 215:200-208 (1989), Xu et al. *Plant Molec. Biol.* 22:573-588 (1993), Logemann et al. *Plant Cell* 1:151-158 (1989), Rohrmeier and Lehle, *Plant Molec. Biol.* 22:783-792 (1993), Firek et al. *Plant Molec. Biol.* 22:129-142 (1993), Warner et al. *Plant J.* 3:191-201 (1993), U.S. Pat. Nos. 5,750,386, 5,955,646, 6,262,344, 6,395,963, 6,703,541, 7,078,589. U.S. Pat. Nos. 7,196,247, 7,223,901, and U.S. Patent Application Publication 2010043102.

As used herein, "expression cassette" means a nucleic acid construct comprising a nucleotide sequence of interest (e.g., the nucleotide sequences of the invention), wherein said nucleotide sequence is operatively associated with at least a control sequence (e.g., a promoter). Thus, some embodiments of the invention provide expression cassettes designed to express the nucleotides sequences of the invention. In this manner, for example, one or more plant promoters operatively associated with one or more nucleotide sequences of the invention (e.g., SEQ ID NO:1, SEQ ID NO:3, SEQ ID NO:5, and/or SEQ ID NO:7) are provided in expression cassettes for expression in an organism or cell thereof (e.g., a plant, plant part and/or plant cell).

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to the nucleotide sequences of the invention, an expression cassette of the invention can also include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, promoters, enhancers, introns, translation leader sequences, termination signals, and polyadenylation signal sequences.

For purposes of the invention, the regulatory sequences or regions can be native/analogous to the plant, plant part and/or plant cell and/or the regulatory sequences can be native/analogous to the other regulatory sequences. Alternatively, the regulatory sequences may be heterologous to the plant (and/or plant part and/or plant cell) and/or to each other (i.e., the regulatory sequences). Thus, for example, a promoter can be heterologous when it is operatively linked to a polynucleotide sequence from a species different from the species from which the polynucleotide sequence was derived. Alternatively, a promoter can also be heterologous to a selected nucleotide sequence if the promoter is from the same/analogous species from which the polynucleotide is derived, but one or both (i.e., promoter and/or polynucleotide) are substantially modified from their original form and/or genomic locus, and/or the promoter is not the native promoter for the operably linked polynucleotide.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski el al. (1990) *Plant Mol. Biol.* 15:65-79). Other leader sequences known in the art include, but are not limited to, picornavirus leaders such as an encephalomyocarditis (EMCV) 5' noncoding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or if the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423): a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

Additional selectable markers include, but are not limited to, a nucleotide sequence encoding β-glucuronidase or uidA (GUS) that encodes an enzyme for which various chromogenic substrates are known: an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105): a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714): a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin, which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of the invention.

An expression cassette of the invention also can include nucleotide sequences that encode other desired traits. Such desired traits can be other nucleotide sequences which confer various agriculturally desirable traits such as disease and/or insect resistance, abiotic stress tolerance or resistance and the like. Such nucleotide sequences can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, nucleotide sequences encoding additional desired traits can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854: WO 99/25840, WO 99/25855 and WO 99/25853.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector comprises a nucleic acid molecule comprising the nucleotide sequence (s) to be transferred, delivered or introduced. Vectors for use in transformation of plants and other organisms are well known in the art. Non-limiting examples of general classes of vectors include, but are not limited to, a viral vector, a plasmid vector, a phage vector, a phagemid vector, a cosmid, a fosmid, a bacteriophage, or an artificial chromosome. The selection of a vector will depend upon the preferred transformation technique and the target species for transformation. Accordingly, in further embodiments, a recombinant nucleic acid molecule of the invention can be comprised within a recombinant vector. The size of a vector can vary considerably depending on whether the vector comprises one or multiple expression cassettes (e.g., for molecular stacking). Thus, a vector size can range from about 3 kb to about 30 kb. Thus, in some embodiments, a vector is about 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 40 kb, 50 kb, 60 kb, and the like or any range therein, in size. In some particular embodiments, a vector can be about 3 kb to about 10 kb in size.

The present invention is directed in part to the discovery that modulating expression by over expressing or inhibiting expression in a plant of at least one isolated nucleic acid molecule or nucleic acid construct of this invention can result in the plant having increased nicotine or reduced nicotine content as compared to a plant that does not comprise said isolate nucleic acid molecule or nucleic acid construct.

Thus, in some embodiments of the invention, a method of producing a transgenic plant cell is provided, said method comprising introducing into a plant cell an isolated nucleic acid molecule/construct of the invention, thereby producing a transgenic plant cell that can regenerate a transgenic plant having modulated (e.g., increased or decreased) alkaloid (e.g., nomicotine, nicotine, anabasine, anatabine, and the like) content as compared to a plant regenerated from a plant cell that does not comprise said nucleic acid molecule/ construct. In some embodiments, the transgenic plant cell comprises more than one (e.g., 2, 3, 4, 5, 6, 7, 8, 9, 10, etc.) nucleic acid molecule/nucleotide sequence of the invention. Thus, in some aspects of the invention, the transgenic plants, or parts thereof, comprise and express one or more isolated nucleic acid molecule/constructs of the invention, thereby producing one or more polypeptides of the invention resulting in modulated (e.g., reduced or increased) alkaloid content in said transgenic plant.

In further embodiments of the invention, a method of producing a transgenic plant cell is provided, said method comprising introducing into a plant cell an isolated nucleic acid molecule/construct of the invention, thereby producing a transgenic plant cell that can regenerate a transgenic plant having modulated (e.g., increased or decreased) nicotine content as compared to a plant regenerated from a plant cell that does not comprise said nucleic acid molecule/construct. In some embodiments, the transgenic plant cell comprises more than one (e.g., 2, 3, 4, 5, 6, 7, 8, 9, 10, etc.) nucleic acid molecule/nucleotide sequence of the invention. Thus, in some aspects of the invention, the transgenic plants, or parts thereof, comprise and express one or more isolated nucleic acid molecule/constructs of the invention, thereby producing one or more polypeptides of the invention resulting in modulated (e.g., reduced or increased) nicotine content in said transgenic plant.

"Introducing," in the context of a nucleotide sequence of interest (e.g., the nucleic acid molecules/constructs of the invention), means presenting the nucleotide sequence of interest to the plant, plant part, and/or plant cell in such a manner that the nucleotide sequence gains access to the interior of a cell. Where more than one nucleotide sequence is to be introduced these nucleotide sequences can be assembled as part of a single polynucleotide or nucleic acid construct, or as separate polynucleotide or nucleic acid constructs, and can be located on the same or different transformation vectors. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, in some embodiments, a plant cell of the invention is stably transformed with a nucleic acid molecule of the invention. In other embodiments, a plant of the invention is transiently transformed with a nucleic acid molecule of the invention.

"Transient transformation" in the context of a polynucleotide means that a polynucleotide is introduced into the cell and does not integrate into the genome or plastome of the cell and consequently said cell cannot be regenerated into a stably transformed plant.

By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

A nucleic acid molecule of the invention (e.g., one or more of the nucleotide sequences of SEQ ID NO:1, SEQ ID NO: 3, SEQ ID NO:5, SEQ ID NO:7, and/or a nucleotide sequence encoding one or more polypeptides having the amino acid sequence of any one of SEQ ID NO:2, SEQ ID NO:4, SEQ ID NO:6, SEQ ID NO:8) can be introduced into a cell by any method known to those of skill in the art.

In some embodiments of the invention, transformation of a cell comprises nuclear transformation. In other embodiments, transformation of a cell comprises plastid transformation (e.g., chloroplast transformation).

Procedures for transforming plants are well known and routine in the art and are described throughout the literature. Non-limiting examples of methods for transformation of plants include transformation via bacterial-mediated nucleic acid delivery (e.g., via *Agrobacteria*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R and Thompson. J. E., Eds. (CRC Press, Inc., Boca Raton, 1993), pages 67-88) and Rakowoczy-Trojanowska (*Cell. Mol. Biol. Lett.* 7:849-858 (2002)).

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and/or plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

Likewise, the genetic properties engineered into the transgenic seeds and plants, plant parts, and/or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, in separate transformation events, or, for example, in plants, as part of a breeding protocol.

Thus, in additional embodiments, the invention provides a method of producing a plant having a plant having modulated alkaloid content is provided, the method comprising introducing into a plant cell a nucleic acid construct of the invention to produce a transgenic plant cell, wherein the transgenic plant cell comprises said nucleic acid construct of the invention in its genome; and regenerating said transgenic plant cell to produce a transgenic plant comprising said nucleic acid construct, thereby producing a plant having modulated alkaloid content. In some embodiments, the alkaloid content of the transgenic plant is increased as compared to a plant that does not comprise said nucleic acid construct. In other embodiments, the alkaloid content of the transgenic plant is decreased as compared to a plant that does not comprise said nucleic acid construct. In representative embodiments, the plant is a tobacco plant.

In further embodiments, the invention provides a method of producing a plant having modulated nicotine content is provided, the method comprising introducing into a plant cell a nucleic acid construct of the invention to produce a transgenic plant cell, wherein the transgenic plant cell comprises said nucleic acid construct of the invention in its genome; and regenerating said transgenic plant cell to produce a transgenic plant comprising said nucleic acid construct, thereby producing a plant having modulated nicotine content. In some embodiments, the nicotine content of the transgenic plant is increased as compared to a plant that does not comprise said nucleic acid construct. In other embodiments, the nicotine content of the transgenic plant is decreased as compared to a plant that does not comprise said nucleic acid construct. In representative embodiments, the plant is a tobacco plant.

In a further embodiment, the present invention provides a method of modulating alkaloid content in a plant, comprising introducing into a plant cell a nucleic acid construct of the invention to produce a transgenic plant cell comprising said nucleic acid construct; and regenerating said transgenic plant cell to produce a transgenic plant comprising said nucleic acid construct, thereby modulating alkaloid content in said transgenic plant as compared to a plant that is not transformed with the said nucleic acid construct. In some embodiments, the alkaloid content of the transgenic plant is increased as compared to a plant that does not comprise said nucleic acid construct. In other embodiments, the alkaloid content of the transgenic plant is decreased as compared to a plant that does not comprise said nucleic acid construct. In representative embodiments, the plant is a tobacco plant.

In a further embodiment, the present invention provides a method of modulating nicotine content in a plant, comprising introducing into a plant cell a nucleic acid construct of the invention to produce a transgenic plant cell comprising said nucleic acid construct; and regenerating said transgenic plant cell to produce a transgenic plant comprising said nucleic acid construct, thereby modulating nicotine production in said transgenic plant as compared to a plant that is not transformed with the (does not comprise) said nucleic acid construct. In some embodiments, the nicotine content of the transgenic plant is increased as compared to a plant that does not comprise said nucleic acid construct. In other embodiments, the nicotine content of the transgenic plant is decreased as compared to a plant that does not comprise said nucleic acid construct. In representative embodiments, the plant is a tobacco plant.

The present invention further provides methods of modulating alkaloid (e.g., nornicotine, nicotine, anabasine, anatabine, and the like) content in a plant and methods of producing plants having modulated alkaloid (e.g., nomicotine, nicotine, anabasine, anatabine, and the like) content comprising in planta modification of one or more of the wild-type or native nucleotide sequences encoding the transcription factors of this invention (e.g., NtMYC2a, NtMYC2b, NtERF98, NtETTa). Any method of modify a nucleotide sequence in planta can be used with this invention to alter the expression of the genes encoding these transcription factors. Such methods can include, but are not limited to, mutagenesis or gene targeting/editing using meganuclease, Zinc Finger nuclease, TALENs, and/or CRISPR/Cas9 nuclease and/or introduction of a nucleic acid or gene repair oligonucleobase comprising at least a portion of SEQ ID NO:1, SEQ ID NO:3, SEQ ID NO:5 or SEQ ID NO:7. In some embodiments, the nucleotide sequence of a transcription factor of the invention can be modified such that an amino acid codon is substituted for a stop codon, resulting in premature termination during translation of the polypeptide and thus resulting in reduced or no activity of the transcription factor, thereby modulating the alkaloid content of the plant.

Procedures for determining nicotine and alkaloid content are well known and routine in the art and are described throughout the literature. Non-limiting examples of methods for measuring nicotine/alkaloid content include such methods as gas chromatography, mass spectrometry (Domino et al. 1992 *Med Sci Res.* 20:859-860; Sheen et al. 2006 *J Food Sci* 53(5):1572-1573), HPLC (Keinanen et al. 2001 *J Agric Food Chem* 49:3553-3558; Halitschke and Baldwin 2003 *Plant J* 36: 794-807), UV absorption (Willits et al. 2005 *Analytical Chemistry* 22:430-433) and the like.

As used herein, the term "modulate," "modulates," "modulated" or "modulation" refers to enhancement (e.g., an increase) or inhibition (e.g., a reduction) in the specified activity (e.g., modulated nicotine production/content).

As used herein, the terms "increase," "increasing," "increased," "enhance," "enhanced," "enhancing," and "enhancement" (and grammatical variations thereof), as used herein, describe an increase in the nicotine content of a plant as a result of the introduction into the plant of an isolated nucleic acid molecule or nucleic acid construct of the invention, thereby producing a transgenic plant having increased nicotine content. This increase in nicotine content can be observed by comparing the nicotine content of the plant transformed with the isolated nucleic acid molecule or nucleic acid construct of the invention to the nicotine content of a plant lacking (i.e., not transformed with) the said nucleic acid molecule or nucleic acid construct of the invention and grown under the same environmental conditions (i.e., a control). The increase can be measured as an increase in percent by weight or as a percent increase of the control value. Thus, in some embodiments, the nicotine content of a plant transformed with an isolated nucleic acid molecule or nucleic acid construct of the invention can be increased by at least about 10%, 15%, 20%, 25%, 30%, 35%, 40%, 45%, 50%, 55%, 60%, 65%, 70%, 75%, 80%, 85%, 90%, 95%, 100%, 125% 150%, 175%, 200%, 250%, 300%, 350%, 400%, 450%, 500% or more as compared with a control. In some embodiments, the nicotine content of a plant transformed with an isolated nucleic acid molecule or nucleic acid construct of the invention can be increased by at least about 30% as compared with a control. In other embodiments, the nicotine content of a plant transformed with an isolated nucleic acid molecule or nucleic acid construct of the invention can be increased by at least about 50% as compared with a control. In still other embodiments, the nicotine content of a plant transformed with an isolated nucleic acid molecule or nucleic acid construct of the invention can be increased by at least about 100% as compared with a control.

In some embodiments, the nicotine content of a plant transformed with an isolated nucleic acid molecule or nucleic acid construct of the invention can be about 10 mg/g (e.g., about 1%) to about 100 mg/g (e.g., 10%) (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 mg/g) dry weight nicotine. In particular embodiments, the nicotine content of a plant transformed with an isolated nucleic acid molecule or nucleic acid construct of the invention can be about 20 mg/g (e.g., about 2%) to about 100 mg/g (e.g., 10%) dry weight nicotine; about 30 mg/g to about 100 mg/g dry weight nicotine, about 40 mg/g to about 100 mg/g dry weight nicotine, about 50 mg/g to about 100 mg/g dry weight nicotine, and the like. In still other embodiments, the nicotine content of a plant transformed with an isolated nucleic acid molecule or nucleic acid construct of the invention can be at least about 30 mg/g dry weight nicotine, at least about 40 mg/g (e.g., about 4%) dry weight nicotine, at least about 50 mg/g (e.g., about 5%) dry weight nicotine, at least about 60 mg/g (e.g., about 6%) dry weight nicotine, and the like.

As used herein, the terms "reduce," "reduced," "reducing," "reduction," "diminish," "suppress," and "decrease" (and grammatical variations thereof), describe, for example, a decrease in the nicotine content of a plant of at least about 1%, 2%, 3%, 4%, 5%, 6%, 7%, 8%, 90%, 10%, 15%, 20%, 25%, 30%, 35%, 40%, 45%, 50%, 55%, 60%, 65%, 70%, 75%, 80%, 85%, 90%, 95%, 100%, or any range therein, as compared with a control as described herein. Thus, in some embodiments, the nicotine content of a plant transformed with an isolated nucleic acid molecule or nucleic acid construct of the invention can be reduced by at least about 1%, at least about 10%, at least about 25%, at least about 50%, at least about 75%, at least about 95% and the like, as compared. In other embodiments, the nicotine content of a plant transformed with an isolated nucleic acid molecule or nucleic acid construct of the invention can be reduced such that the control plant has a level at least about 2 fold to about 10 fold (e.g., at least about 2, 3, 4, 5, 6, 7, 8, 9, 10 fold and the like) as compared to the transformed plant. In representative embodiments, the reduction is by about 5 fold to about 7 fold.

A further aspect of the invention provides transformed non-human host cells and transformed non-human organisms comprising the transformed non-human cells, wherein the transformed cells and transformed organisms comprise nucleic acid molecules comprising one or more nucleotide sequences of the invention. In some embodiments, the transformed non-human host cell includes but is not limited to a transformed bacterial cell, and/or a transformed plant cell. Thus, in some embodiments, the transformed non-human organism comprising the transformed non-human host cell includes, but is not limited to, a transformed bacterium, and/or a transformed plant.

In some particular embodiments, the invention provides a transgenic plant cell comprising a nucleic acid molecule of the invention and/or a transgenic plant regenerated from said transgenic plant cell. Accordingly, in some embodiments of the invention, a transgenic plant having modulated (e.g., increased or reduce) nicotine content is provided, said transgenic plant regenerated from a transgenic plant cell comprising at least one isolated nucleic acid molecule/nucleic acid construct of the invention.

Additional aspects of the invention include a harvested product produced from the transgenic plants and/or parts thereof of the invention, as well as a processed product produced from said harvested product. A harvested product can be a whole plant or any plant part, as described herein, wherein said harvested product comprises a recombinant nucleic acid molecule/construct of the invention. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, cigarette, cigarette tobacco, cigar tobacco, a cigar, pipe tobacco, chewing tobacco, leaf tobacco, shredded tobacco and cut tobacco, and the like produced from a transgenic plant of the invention.

A plant useful with this invention can be any plant that produces nicotine and/or other related alkaloids. Thus, in some embodiments, the plant can be *Nicotiana tabacum*. *Nicotiana rustica* or *Nicotiana benthamiana*. Any variety of tobacco is useful with this invention including, but not limited to, Aromatic Fire-cured, Brightleaf tobacco, Burley: Cavendish; Corojo; Criollo; Oriental Tobacco; Perique; Shade tobacco: Thuoc lao; Type 22: NC95, K326, K346, White Burley, Wild Tobacco, Y1, and the like.

Thus, in some particular embodiments, a transgenic plant of the invention includes, but is not limited to, a transgenic tobacco plant or part thereof is provided, wherein the nicotine content of said plant or part thereof is modulated.

As used herein, the term "plant part" includes but is not limited to embryos, pollen, ovules, seeds, leaves, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. Further, as used herein, "plant cell" refers to a structural and physiological unit of the plant, which comprises a cell wall and also may refer to a protoplast. A plant cell of the invention can be in the form of an isolated single cell or can be a cultured cell or can be a part of a higher-organized unit such as, for example, a plant tissue or a plant organ. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, an embryo cell, an ovule cell, a pollen cell, and the like.

In some particular embodiments, the invention provides a transgenic seed produced from a transgenic plant of the invention, wherein the transgenic seed comprises a nucleic acid molecule/nucleotide sequence of the invention.

"Plant cell culture" means cultures of plant units such as, for example, protoplasts, cell culture cells, cells in plant tissues, pollen, pollen tubes, ovules, embryo sacs, zygotes and embryos at various stages of development. In some embodiments of the invention, a transgenic tissue culture or transgenic plant cell culture is provided, wherein the transgenic tissue or cell culture comprises a nucleic acid molecule/nucleotide sequence of the invention.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

The invention further provides a plant crop comprising a plurality of transgenic plants of the invention planted together in an agricultural field. In some embodiments, the plant crop comprises a plurality of transgenic tobacco plants of the invention planted together in an agricultural field.

"Genetic engineering" encompasses any methodology for introducing a nucleic acid or specific mutation into a host organism. For example, a plant is genetically engineered when it is transformed with a polynucleotide sequence that suppresses expression of a gene, such that expression of a target gene is reduced compared to a control plant. A plant is genetically engineered when a polynucleotide sequence is introduced that results in the expression of a novel gene in the plant, or an increase in the level of a gene product that is naturally found in the plants. In the present context, "genetically engineered" includes transgenic plants and plant cells, as well as plants and plant cells produced by means of targeted mutagenesis effected, for example, through the use of chimeric RNA/DNA oligonucleotides, as described by Beetham et al., *Proc. Natl. Acad. Sci. U.S.A.* 96: 8774-8778 (1999) and Zhu et al., *Proc. Natl. Acad. Sci. USA.* 96: 8768-8773 (1999), or so-called "recombinagenic olionucleobases," as described in International patent publication WO 2003/013226. Likewise, a genetically engineered plant or plant cell may be produced by the introduction of a modified virus, which, in turn, causes a genetic modification in the host, with results similar to those produced in a transgenic plant, as described herein. See, e.g., U.S. Pat. No. 4,407,956. Additionally, a genetically engineered plant or plant cell may be the product of any native approach (i.e., involving no foreign nucleotide sequences), implemented by introducing only nucleic acid sequences derived from the host plant species or from a sexually compatible plant species. See, e.g., U.S. published patent application No. 2004/0107455.

"Tobacco product" refers to a product comprising material produced by a *Nicotiana* plant, including for example, nicotine gum and patches for smoking cessation, cigarette tobacco including expanded (puffed) and reconstituted tobacco, cigar tobacco, pipe tobacco, cigarettes, cigars, and all forms of smokeless tobacco such as chewing tobacco, snuff, snus and lozenges. "Cigarettes" includes electronic cigarettes and "heat not burn" products which are cigarette-like devices that heat tobacco rather than burn tobacco.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Materials and Methods

A. Yeast One-Hybrid Experiments for Cloning Transcription Factors

Bait Vector Construction

A yeast one-hybrid system, Matchmaker™ One-Hybrid Library Construction and Screening Kit (Clontech, Mountain View, Calif.), was employed to screen for transcription factors that bind to the promoter of the tobacco QPT2 gene (U.S. Pat. No. 5,837,876). The promoter, 1034 bp in length, was cleaved from pTobRD2-PMT$_{ox}$ construct provided by the 22$^{nd}$ Century LLC. (Buffalo, N.Y.), and inserted upstream of the GAL4 minimal promoter in vector pHIS2.1 to form the bait construct pTobHis. The insert was first verified by BamHI digestion and the orientation of the promoter was confirmed by PCR using the following primers designed from sequence of the QPT2 promoter and His3 gene:

```
Tob1F:
                                          (SEQ ID NO: 9)
5'-ACATCTGTAACCGGAACAGCAC-3'

His1R:
                                          (SEQ ID NO: 10)
5'-GGTCGTCTATGTGTAAGTCACC-3'
```

Yeast strain Y187 was transformed with the bait construct pTobHis and 100 µL of 1/15 dilution of the original transformants was plated on SD/-Trp and SD/-Trp/-His media, respectively. The plates were titrated with a series of 3-AT (3-amino-1, 2, 4-triazole) (0, 5, 10, 15, 20, 30, 50, 75, 100 mM) to optimize the concentration that suppresses the basal expression of the bait construct. The plates were cultured at 30° C. for five days.

cDNA Library Construction

Total RNA was extracted from roots of two-month-old greenhouse-grown tobacco plants (cv. NC95) 0.5 hr after topping. An oligo(dT) primer, modified by fusion with a 25-mer sequence, called CDS III, and the SMART™ III primer from the kit were used for synthesis of the first strand cDNA so to flank the synthesized cDNA with the two primer sequences. Long distance PCR (LD-PCR) was performed to amplify the synthesized cDNA using the Advantage 2 PCR kit (Clontech) with the CDS III and SMART™ III primers based on the manufacturer's instruction. The PCR product was examined on agarose gel and the double-stranded cDNA was purified with CHROMA SPIN TE-400 columns from the kit and concentrated.

Yeast Transformation and Positive Colony Selection

Yeast competent cells were prepared and transformed with the bait vector pTobHis, the linearized prey vector pGADT7-Rec2, and the ds cDNA (~4 µg) following the manufacturer's instructions. The homologous recombination between the prey vector and the ds cDNA took place at the CDS III and SMART™ III sites of the linearized prey vector inside the yeast cells. The transformed cells were propagated, collected, and spread on DDO medium (SD/-Leu/-Trp) to estimate the screening efficiency of the co-tranformation, and on TDO medium (SD/-Leu/-Trp-His) to identify colonies positive in the one-hybrid selection.

Characterization of Positive Colonies from Yeast One-Hybrid Selection

The insert length of the positive colonies was evaluated by a standard 30-cycle PCR (Bioneer, Alameda, Calif.) with 1 µL overnight yeast culture and the following two primers provided by the kit:

```
5' PCR Primer:
                                          (SEQ ID NO: 11)
5'-TTCCACCCAAGCAGTGGTATCAACGCAGAGTGG-3'

3' PCR Primer:
                                          (SEQ ID NO: 12)
5'-GTATCGATGCCCACCCTCTAGAGGCCGAGGCGGCCGAC-3'
```

The PCR products were examined on agarose gels, and all the prey constructs with cDNA inserts longer than 500 bp were subjected to plasmid isolation with QIAprep Spin Miniprep kit (Qiagen, Valencia, Calif.). The plasmids isolated from yeast colonies were subsequently transformed into E. coli DH5a for propagation. The prey plasmids were isolated again from E. coli and the cDNA inserts were subjected to sequence analysis using the T7 primer and the 3'PCR primer. Any yeast colony which contained more than one prey constructs was re-streaked on SD/-Leu for 2-3 times until the PCR result yields a single amplified fragment.

The sequences of the cDNA inserts were used for BLAST analysis with the NCBI GenBank database. A total of five transcription factors were identified from about 100 positive colonies. However, none of these five transcription factor cDNAs was in full length but they all had poly(A) tails.

Recovery of Full-Length cDNAs of the TFs

RNA was isolated from root tissue of greenhouse grown NC95 tobacco plants 0.5 hr after topping. The GENERACER™ kit (Invitrogen, Carlsbad, Calif.) was used to obtain the missing 5' sequences of the TF cDNAs following the manufacturer's manual. One or two gene specific primers were designed based on the sequences near the 5' termini of the partial cDNAs of the six isolated TF genes for PCR together with the GENERACER™ 5' primer provided by the kit. The sequences of these gene specific primers are:

```
NtERF GSP1:
                                          (SEQ ID NO: 13)
5'-CTATCTCCGACTTCTGGTCTTCCTCT-3'

NtERF GSP2:
                                          (SEQ ID NO: 14)
5'-CCACGGTCTCTGCCTTATTCCTCTGTA-3'

NtMYC2a GSP1:
                                          (SEQ ID NO: 15)
5'-ACACATTTGGTACAACAGCTCTAAGTGC-3'

NtMYC2a GSP2:
                                          (SEQ ID NO: 16)
5'-TGCAATTGCATCACCAAGAAGTGATGCT-3'
```

-continued

NtMYC2b GSP:
(SEQ ID NO: 17)
5'-CGCTGGAGTTGGTGTAGTAG-3'

NtARF GSP1:
(SEQ ID NO: 18)
5'-CCTTTTGTGTCTCCCTTCCTACTGATG-3'

NtARF GSP2:
(SEQ ID NO: 19)
5'-CTAAGTTTTGAGAGCACTGGGTCCCAAG-3'

After the full-length cDNAs were recovered, primers were designed to obtain the full-length coding sequences of these four transcription factors by PCR:

NtERFFL1F:
(SEQ ID NO: 20)
5'-TCTAGAGGATCCCGGGATGTGTGGAGGTGCCATAATCC-3'

NtERFFL1R:
(SEQ ID NO: 21)
5'-GCGCCCGGGTTCAGTAAAACAGCTGCTGCTGC-3'

NtARFFL1F:
(SEQ ID NO: 22)
5'-GGATCCATGATGTGTGGACTTATTGATC-3'

NtARFFL1R:
(SEQ ID NO: 23)
5'-CCCGGGCTACAAAGCAATATCAAGAATC-3'

NtMYC2a 1F:
(SEQ ID NO: 24)
5'-GCGGTCTAGACAGATCTGAATTGATTTGTCT-3'

NtMYC2a 1R:
(SEQ ID NO: 25)
5'-GCGGTCTAGAACATTATTCAGAGCTCACTATG-3'

NtMYC2b 1F:
(SEQ ID NO: 26)
5'-GCGTCTAGAATGACGGACTATAGAATACCA-3'

NtMYC2b 1R:
(SEQ ID NO: 27)
5'-GCGTCTAGATCATCGCGATTCAGCAATTCT-3'

All PCR reactions were performed using the high-fidelity Taq DNA polymerase (Phusion, Finnzymes. Espoo, Finland). The PCR products were cloned into pCRBluntII-TOPO or pCR4-TOPO vector (Invitrogen) for sequence analysis by a commercial provider.

B. Expression Analysis of the Isolated Transcription Factors in Tobacco

Tobacco plants (cv. NC 95), grown in the greenhouse for about two months until just before flowering, were subjected to gene expression analysis in various organs as well as in roots after topping, wounding, or MeJA (Sigma, St. Louis, Mo.) treatments. Topping was performed by cutting off the shoot apex of plants immediately below the bud. Wounding was performed by cutting leaves on the plants with scissors: five cuts per leaf on top three fully-grown leaves. For the MeJA treatment, 50 µM solution (about 5 mL) was sprayed on all the plant leaves.

Root tissues were collected at the time points of 0 h, 0.25 h, 0.5 h, 1 h, 2 h, 4 h, and 6 h after treatments. RNA samples were isolated and Northern blot analysis was performed as described in Chapter 1. The primers designed from the coding sequences used to generate the probes for Northern hybridization were:

NtERFNOR F:
(SEQ ID NO: 28)
5'-ACACTGCACTAGCACCATCCC-3'

NtERFNOR R:
(SEQ ID NO: 29)
5'-CTGCATTGTACTACGTACTACC-3'

NtMYC2a/bNOR F:
(SEQ ID NO: 30)
5'-GAAGTAACGGATACTGAATGG-3'

NtMYC2a/bNOR R:
(SEQ ID NO: 31)
5'-ATCCTTGTGTTTGCTGAGAAT-3'

NtARFNOR F:
(SEQ ID NO: 32)
5'-CTGCCTATAGCCAACTGTTG-3'

NtARFNOR R:
(SEQ ID NO: 33)
5'-AAGCTGCTGGATACAGGAGC-3'

C. Tobacco Transformation for Over-Expression and Down-Regulation of the Isolated Transcription Factors pBI21 was used as the backbone vector to make the over-expression and RNAi gene constructs. The coding sequences of the isolated transcription factors were cleaved from their cloning vectors (pCRBIuntII-TOPO or pCR4-TOPO) and inserted into pBI121 at the place of the GUS gene to be under control of the constitutive CaMV 35S promoter (FIG. 1).

The RNAi technique was used to down-regulate the individual TFs in transgenic tobacco plants. For RNAi vector construction, the partial coding sequence of each TF was obtained by PCR with the following pairs of the primers:

NtERFRNAiF:
(SEQ ID NO: 34)
5'-GACTGAGCTCTCTAGAGTGGAGGTGCCATAATCCCCGA-3'

NtERFRNAiR:
(SEQ ID NO: 35)
5'-GACTCCCGGGGATATCCGGTCTCTGCCTTATTCCTCTGTA-3'

NtMYC2RNAiF:
(SEQ ID NO: 36)
5'-GGGGAGCTCTCTAGAGCTGCAACAGCGACTCCAGA-3'

NtMYC2RNAiR:
(SEQ ID NO: 37)
5'-ATTCCCGGGGTCGACCCGTTAACAAACGATTGAGTC-3'

NtARFRNAiF:
(SEQ ID NO: 38)
5'-GGGGAGCTCGGATCCGATGGGATTGCAGTATCAGAC-3'

NtARFRNAiR:
(SEQ ID NO: 39)
5'-GGGACTAGTGTCGACGAGTACTTGGATTGCAATGAC-3'

Figure 2:
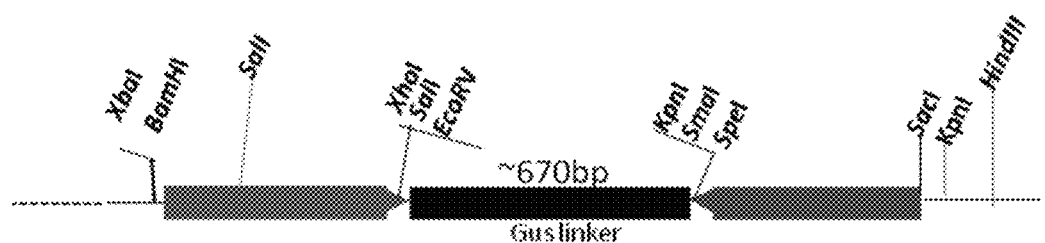
FIG. 2 provides a schematic representation of the region of vector pQLi used for inverted repeat cloning. Gus linker: partial sequence from GUS gene.

The PCR fragment was first cloned into pQLi to replace the red and blue regions (as shown in FIG. 2) to create inverted repeat, and then the whole cassette was inserted into pBI121 to replace the GUS gene. All the resultant over-expression and RNAi vectors were confirmed by appropriate restriction digestions and sequencing analysis. FIG. 2 provides a schematic representation of the region of vector pQLi used for inverted repeat cloning.

Agrobacterium-mediated tobacco transformation was performed using Agrobacterium strain LBA4404 and a leaf disc protocol (Horsch et al. (1985) Science 227: 1229-1231).

Small leaf pieces from the plants to be transformed were mixed with overnight-grown *Agrobacterium tumefaciens* culture ($OD_{600}$=1.0) for 2 min. Excess *Agrobacterium* culture solution was removed using sterile paper towel. Co-cultivation was conducted for 2-3 days on MS medium. MS medium with BA (1 mg/L), IBA (0.1 mg/L) and kanamycin (100 mg/L) was used as the selection medium. Subculturing was performed 2-3 times at 2-wk interval. Non-transformed control plants were also regenerated using the same media and procedure but without antibiotic selection. The rooting medium was MS with 50 mg/L kanamycin and no hormones. Putative transgenic tobacco plants (cv. NC 95) were grown in the greenhouse for about two months and root tissues were collected just before flowering.

Total RNA was extracted using TRIzol Reagent (Invitrogen, Carlsbad, Calif.) according to the manufacturer's protocol. Approximately 700 mg root tissue or 200 mg leaf tissue were used for RNA isolation. For Northern blot analysis, the extracted RNA was dissolved in DEPC-treated water and quantified with the Nanodrop (ND-1000). Ten plg RNA was separated on a 1% agarose gel in MOPS buffer. The gel was stained with EtBr and the image was photographed under UV illumination. Separated RNA on the gel was blotted onto the Hybond-N+nylon membrane. The primers used to generate probes were the same as described above.

D. qRT-PCR Analysis of Pathway Gene Expression Root was collected from $T_0$ transgenic plants before flowering. RNA was isolated from root tissue using TRIzol reagent (Invitrogen) according to the manufacturer's manual and first strand cDNA was synthesized using SuperScript™ III ReverseTranscriptase (Invitrogen) with an oligo(dT) primer, qRT-PCR was performed using FastStart Universal SYBR Green Master (Rox) (Roche. Mannheim, Germany) on AB17900 (Applied Biosystems, Foster City, Calif.). Tobacco actin gene was chosen as a control for normalization. Three technical replicates were performed with RNA samples from each transformation event using the following PCR program: 50° C. for 1 min; 95° C. for 15 sec; 40 cycles of 95° C., 15 sec followed by 63° C., 1 min with the primers for pathway genes listed in Table S3. Two transformation events per gene construct were analyzed.

The means and standard errors are presented.

E. Electrophoretic Mobility Shift Assays (EMSA) Since the yield of the full length MYC2a protein when expressed in *E. coli* was very low, we used the N-truncated MYC2a protein for EMSA. N-truncated MYC2a protein (MYC2aΔN, from No. 264 to No. 659 AA) was expressed in fusion with GST in Rosetta 2(DE3) Singles (Novagen, Madison, Wis.). The cell culture was treated with 0.2 mM IPTG for 4 h at 15° C. to induce protein expression.

The recombinant protein was purified using glutathione-agarose beads (Sigma) and the MYC2aΔN was cleaved and eluted from the beads with thrombin (Sigma). Thrombin was removed from MYC2aΔN solution with pAminobenzamidine-Agarose (Sigma) and the MYC2aΔN was concentrated by Amicon Ultra centrifugal filter units Ultra-15 (MWCO 10 kDa) (Millipore, Billerica, Mass.).

Probe was labeled according to the manual of kit (Biotin 3' End DNA Labeling Kit, Pierce, Rockford, Ill.). Two complementary oligomers were labeled on the 3' ends. Double strand DNA was prepared by mixing of equal amount of labeled complementary oligomers. Mixture was heated at 95° C. for 5 min and cooled down to room temperature for 1 h.

G2-box prob:

(SEQ ID NO: 40)
-189 5'-AGTAGCTGAACACGTTTTATTTATGGTTGTTGAATAGT-3'-227

(SEQ ID NO: 41)
3'-TCATCGACTTGTGCAAAATAAATACCAACAACTTATCA-5'

Mutated G2-box cold probe.

(SEQ ID NO: 42)
5'-AGTAGCTGAATCACATTTATTTATGGTTGTTGAATAGT-3'

(SEQ ID NO: 43)
3'-TCATCGACTTAGTGTAAATAAATACCAACAACTTATCA-5

EMSA was performed according to manual of the kit (LightShift® Chemiluminescent EMSA Kit, Pierce). The binding buffer was 10 mM Tris, 50 mM KCl, 1 mM DTT, 0.05 μg/μl poly(di-dc), 0.05% NP-40, and 2.5% (v/v) glycerol. The probe was 20 fmol for each reaction. The cold probe and mutated probe were 10 pmol (500×) and the protein was 0.75 μg MYC2aΔN. The binding reaction was performed at room temperature for 20 min. The reaction mixture was separated on a 5% polyacrylamide gel and blotted on Hybond™-N⁺ membrane (Amersham, Piscataway, N.J., USA). UV crosslinker was used to crosslink the DNA to membrane. The membrane was probed and signal was detected according to the manual of kit (Chemiluminescent Nucleic Acid Detection Module Kit, Pierce). Kodak BioMax MS film (Carestream Health, Inc. Rochester, N.Y.) was exposed to record the signal.

F. Quantification of Major Alkaloids

Nicotine levels in dried leaves of the transgenic plants were kindly quantified by gas chromatography. Each sample was prepared by placing 0.2000±0.0010 g of dried ground tobacco leaves into a 50 mL Erlenmeyer flask. Two mL of 2N NaOH solution was added to each flask and swirled to moisten the tobacco. After 15 min of rest, 10 mL of methyl tertiary butyl ether (MTBE) containing 0.1062 g/mL of quinoline was added to the flask. The flasks were placed on a shaker for 2.5 hrs. After shaking the flasks were allowed to sit overnight to separate. Approximately 1 mL of the top MTBE layer was transferred into a vial. GC analysis was conducted using a split injection (40:1) on an Agilent HP 6890 GC-FID (Agilent Technologies, Santa Clara, Calif.) using a 30 meter DB-5 MS column (0.53 mm ID and 1.5 μm film thickness). The carrier gas was helium at a linear velocity of approximately 38 cm/sec. The injector and detector were both set at 250° C. The analysis consists of a temperature program from 110° C. initially held for 0.5 min followed by a ramp to 280° C. at a rate of 25° C./min where the final temperature was held for 20 min. Data were collected and analyzed using Agilent Chemstation software. A multi point internal standard calibration table was constructed for each compound. The curves for each compound are as follows:

$Y = 2.32779e-1*x + 8.05332e-3$     Nicotine:

$Y = 2.26220e-1*x - 3.49890e-3$     Nornicotine:

$Y = 2.23584e-1*x + 2.27888e-4$     Anabasine:

$Y = 1.33963e-1*x - 3.08881e-3$     Anatabine:

Example 2. Identification of the Transcription Factors

The yeast one-hybrid technique was used in this study to identify the transcription factors. This technique includes three important components: bait construct, prey vector, and cDNA. The QPT2 promoter region was inserted upstream the GAL4 minimal promoter in the bait vector, which drives a histidine synthesis gene HIS3. Thus, if the yeast cell contains the bait vector and a prey vector expressing a TF-GAL4 AD (activation domain) fusion protein that binds to the QPT2 promoter, the HIS3 gene will express and the cell will be able to grow on a screening medium which lacks histidine. The bait construct was confirmed by restriction digestion and PCR for the insertion of the QPT2 promoter and its orientation. It was then tested for leaking expression of HIS3 (or basal expression because of endogenous yeast transcription factors), 3-amino-1, 2, 4-triazole (3-AT) is a competitive inhibitor of the reporter gene HIS3 product, a histidine biosynthetic enzyme. A titration experiment of 3-AT was conducted to optimize 3-AT concentration in the yeast culture medium to minimize potential false positives in the screening experiments. No colony grew on the medium (SD/-His/-Trp containing a series of 3-AT from 5 mM to 75 mM) while many colonies grew on the control plate of SD/-Trp. This experiment was repeated and the same result was obtained. Thus, it was not necessary to add 3-AT to the screening medium to suppress the basal expression of HIS3 gene and the background growth.

Total RNA was extracted from the root tissue collected 30 min after topping and used to make a cDNA library for the yeast one-hybrid screening. Many of the nicotine biosynthetic pathway genes are induced several hrs after topping and it was expected that the transcription factor genes would be induced earlier. A time of 30 min after topping was estimated to be appropriate to capture a "snapshot" of the expression of these transcription factors. The quality of the cDNA was examined by PCR.

A total of three screening experiments were performed by transforming yeast competent cells with the bait vector, the prey vector, and the cDNA collection (homologous recombination would take place between the prey vector and the cDNA inside the yeast cell so the cDNA-GAL4 AD fusion gene will express from the prey vector), and approximately 1.6 million yeast colonies were screened. After seven days of incubation, actively-growing yeast colonies were selected for colony PCR to screen for prey plasmid which has the cDNA insert longer than 500) base pair. All yeast colonies which contained more than one prey plasmid (more than one amplified DNA fragment on agarose gels) were subjected to successive re-streaking on SD/-Leu medium until only one prey plasmid was left in the colony. The isolated prey plasmid was used to transform *E. coli* (strain DH5a) for plasmid propagation. Approximately 100 yeast positive colonies were finally isolated and sequenced, among which five were putative transcription factors as identified based on the BLAST analysis with the NCBI GenBank database. These five transcription factors were shown to belong to five TF families: GRAS, AP2/ERF, bHLH, ARF and WRKY.

All the cloned TF cDNAs were partial in length with their 5' sequences missing. To obtain full-length cDNAs for these TFs, the 5' RACE (Rapid Amplification of cDNA Ends, Invitrogen, Carlsbad, Calif.) technique was performed, and high-fidelity Taq DNA polymerase was used in all the PCR reactions. For each TF, at least five randomly picked colonies were subjected to sequence analysis. During the process, another bHLH gene with high homology to the cloned one was identified and cloned. The sequences and expression patterns of these TF genes were characterized. To test whether these transcription factors have effects on nicotine biosynthesis pathway, transgenic over-expression and RNAi lines of all the six transcription factors were produced.

Transformed plants were grown in the greenhouse for about two months. Total RNA was extracted from root tissue and subjected to Northern blot analysis of pathway gene expression and nicotine concentration.

Example 3. Transcription Factor NtMYC2a and NtMYC2b Genes

Two full-length bHLH transcription factor cDNAs were cloned with 2214 and 2391 bp in length and encoding 659 and 658 AA, respectively (see, Appendix). They share 96% identity at the cDNA sequence level. The two TFs were named NtMYC2a and NtMYC2b.

A. NtMYC2 Expression Pattern in Tobacco

Figure 3:
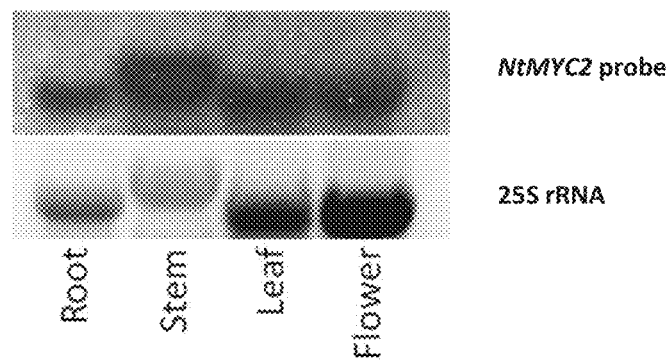
FIG. 3 shows organ expression pattern of NtMYC2.

Northern blot analysis (FIG. 3) shows NtMYC2 genes expressed in tobacco root, stem, leaf and flower. Total RNA isolated from various organs of fully grown plant was probed with NtMYC2b PCR fragment probes. The 25S rRNA stained with EtBr in gel is also shown as a loading reference. Due to the high homology between the two MYC2 genes, the probe for all the Northern blot analysis of MYC2 is a partial coding sequence of 505 bp from MYC2b, and cannot distinguish the two genes and thus they were analyzed together. Northern blot analysis shows that, despite nicotine biosynthesis occurring only in root, and the pathway genes, such as NtPMT, NtQPT2, and NtMPO, expressing only in root, NtMYC2 has expression in all the four organs (root, stem, leaf and flower) examined without any treatment, and the highest expression in stem (FIG. 3). NtMYC2 expression in all major organs indicates the TFs also function in metabolic pathways other than nicotine biosynthesis (Dombrecht et al. (2007) *Plant Cell* 19: 2225-2245).

Figure 4:
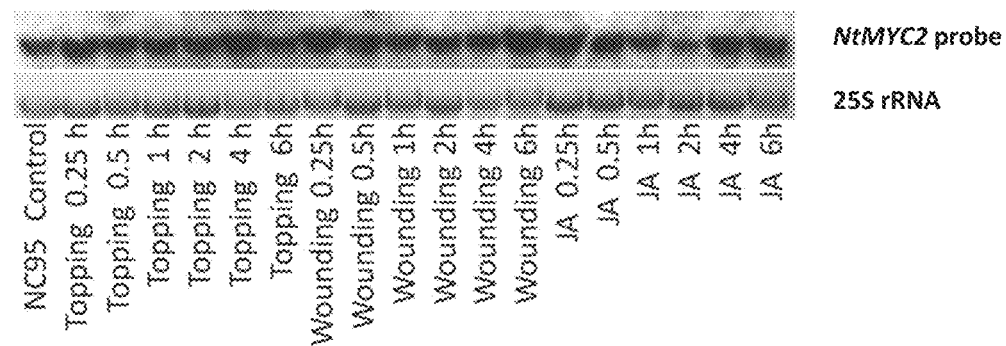
FIG. 4 shows NtMYC2 expression in tobacco root after topping, wounding, or MeJA treatment. Northern hybridization shows a time course induction pattern of NtMYC2 after each treatment. The probe is from NtMYC2b. The 25S rRNA stained in gel with EtBr is shown as a loading reference.

B. NtMYC2 Expression Patterns in Tobacco Root after Topping, Wounding, and MeJA Treatment Since nicotine accumulation was induced by topping, wounding, or MeJA treatment, expression of the NtMYC2 genes in root after these individual treatments was investigated. Two-month-old tobacco plants (just before flowering) were treated with topping, wounding or MeJA, and the root total RNAs were used for northern analysis. Northern hybridization shows a time course induction pattern of NtMYC2 after each treatment. The probe is from NtMYC2b. The 25S rRNA stained in gel with EtBr is shown as a loading reference. As shown in FIG. 4, NtMYC2 expression was induced in root by topping, wounding, or MeJA treatment. Compared to the control, the induced expression of NtMYC2 seems to be biphasic: the expression increased 0.25 h after the treatments, declined slightly afterwards, and increased again at 4 or 6 h time point, with wounding having the strongest induction effect among the three treatments.

C. NtMYC2a Binds to the G2 Box in NtQPT2 Promoter

Three G-boxes (G2, G3 and G4) were identified in the 0.6 kb NtQPT2 promoter (NCBI accession No. AJ748263), among which G2 box has the highest binding strength with NtMYC2b (Shoji and Hashimoto, 2011). To validate that NtMYC2a binds to G2-box. EMSA experiment was performed with probes of 38 bp consisting of a G2 box (CACGTT) and flanking regions from the NtQPT2 promoter and mutated probe with mutation in the G2 box sequence. We cloned the full length of NtMYC2a and expressed the recombinant protein (NtMYC2a fused with GST) in *E. coli*. Due to the very low yield of the full length NtMYC2a protein, we truncated it and only expressed the C-terminal bHLH domain of the NtMYC2a protein (NtMYC2aΔN, from No. 264 to No. 659 AA).

Figure 5:
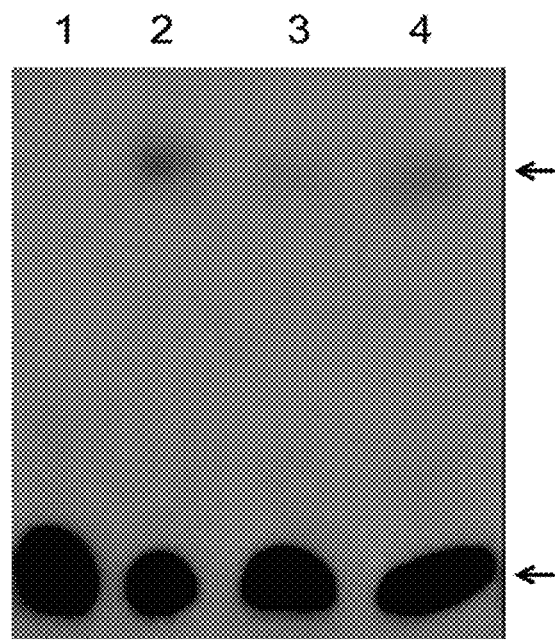
FIG. 5 shows binding of NtMYC2a to the G2-box in zNtQPT2 promoter. Lane 1, no protein: lane 2, NtMYC2aΔN+probe: lane 3, NtMYC2aΔN+probe+500× cold probe: lane 4, NtMYC2aΔN+probe+500×mutated cold probe. Arrows indicate the shifted (migrate slower) and free probes, respectively.

The binding experiment showed that NtMYC2aΔN specifically binds to the G2 box in the NtQPT2 promoter in vitro (FIG. 5). Dilution with cold probe reduced the binding signals whereas dilution with mutated cold probe maintained most of the signals.

D. Analysis of NTMYC2a and NtMYC2b Transgenic Lines

Seven NtMYC2a and nine NtMYC2b over-expression lines and nine NtMYC2 RNAi transgenic lines, in which both genes are expected to be suppressed, were generated to test the effect of these two TF genes on nicotine biosynthesis. The 336 bp fragment used for RNAi construct was from NtMYC2b coding sequence, which shares 946 identity with that region of NtMYC2a gene.

Figure 6:
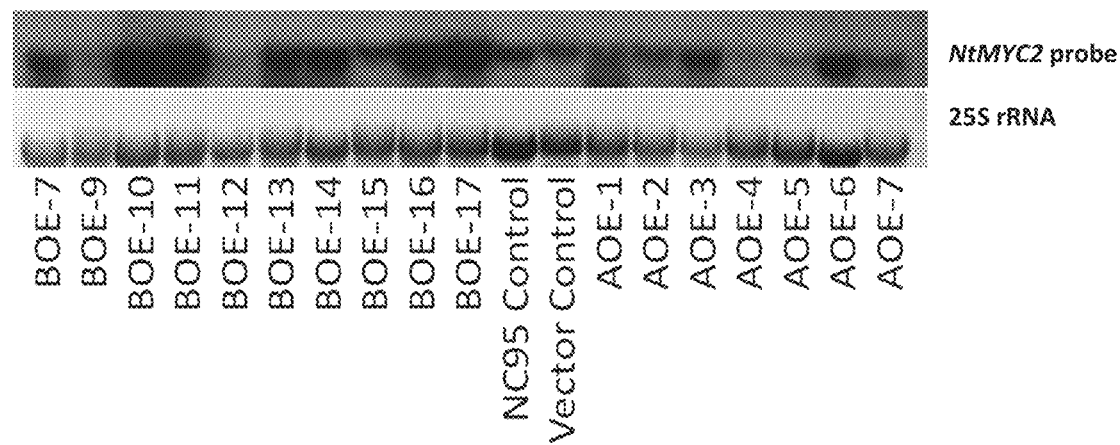
FIG. 6 shows expression of NtMYC2a and NtMYC2b in NtMYC2a or NtMYC2b over-expression lines. Northern hybridization shows NtMYC2 mRNA level in NtMYC2a or NtMYC2b over-expression lines. The bottom panel shows the ribosomal RNA in gel stained with EtBr as an RNA loading reference. The wild-type and vector control are also shown.

FIG. 6 shows the expression levels of NtMYC2a and NtMYC2b in transgenic plants over-expressing NtMYC2a or NtMYC2b gene. Compared to the wild type and vector control, two lines of NtMYC2a (AOE-3, and 6) and seven lines of NtMYC2b (BOE-7, 10, 11,13,14,16, and 17) were clearly over-expression lines.

Figure 7:
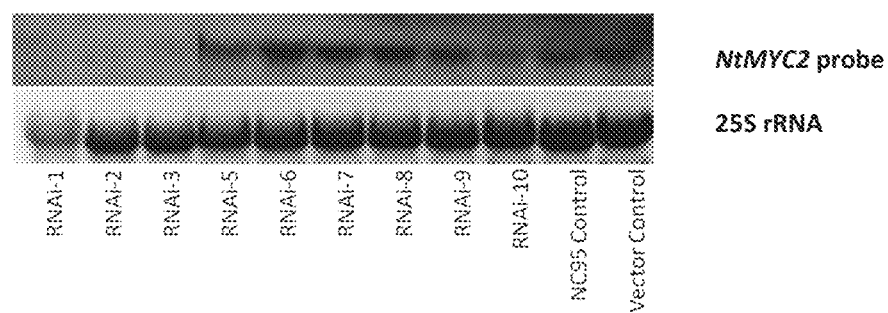
FIG. 7 shows the combined expression of NtMYC2a and NtMYC2b in NtMYC2 RNAi lines. Top panel: Northern hybridization of NtMYC2 mRNA level in NtMYC2 RNAi lines. The bottom panel shows ribosomal RNA in gel stained with EtBr as an RNA loading reference. The wild-type and vector control are also shown.

FIG. 7 shows the effects of the RNAi construct on NtMYC2a/b expression. Expression level of NtMYC2 in three RNAi lines (RNAi-1, 2, 3) was greatly reduced. All other lines did not show substantial changes in NtMYC2 expression.

Figure 8:
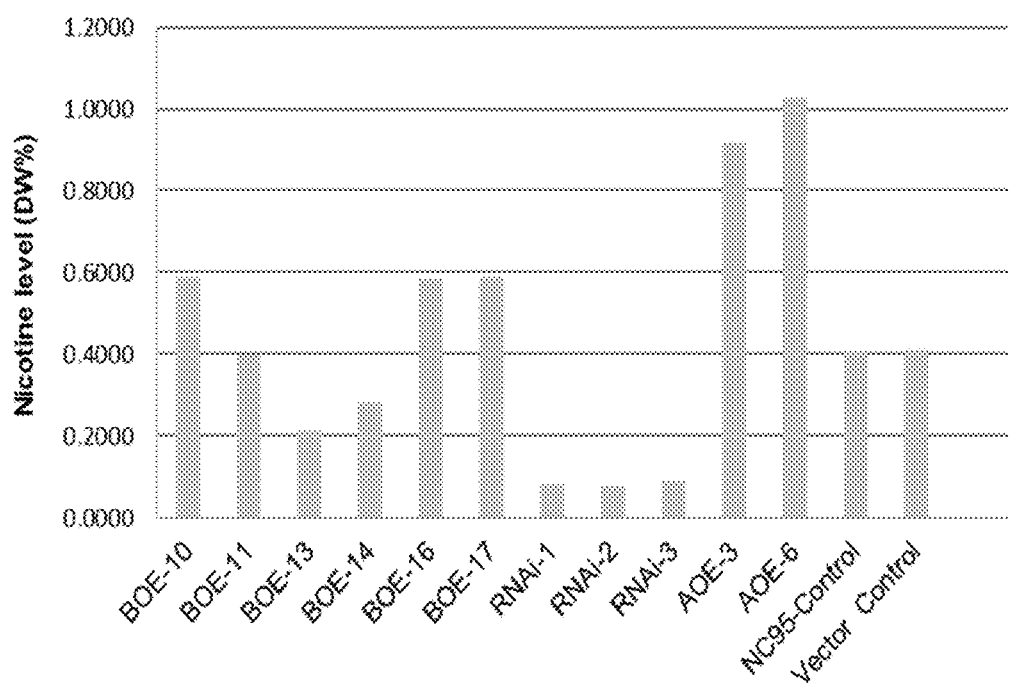
FIG. 8 shows nicotine concentration of over-expression and RNAi lines of NtMYC2a and NtMYC2b. DW: dry weight.

Based on the Northern analysis, nicotine levels of two NtMYC2a over-expression and six NtMYC2b over-expression lines with high transgene expression and three RNAi lines with much lower expression of NtMYC2 were quantified (FIG. 8).

FIG. 8 shows that three NtMYC2b over-expression lines (BOE-10, 16, and 17) and two NtMYC2a over-expression lines (AOE-3 and AOE-6) had higher nicotine level than the controls (41% to 149% higher than vector control). However, other lines with higher expression level of NtMYC2b, such as BOE-11, 13, and 14 didn't have higher nicotine level. The three RNAi lines (RNAi-1, 2 and 3) showed much lower nicotine level (about five-fold less) than the controls.

Figure 9:
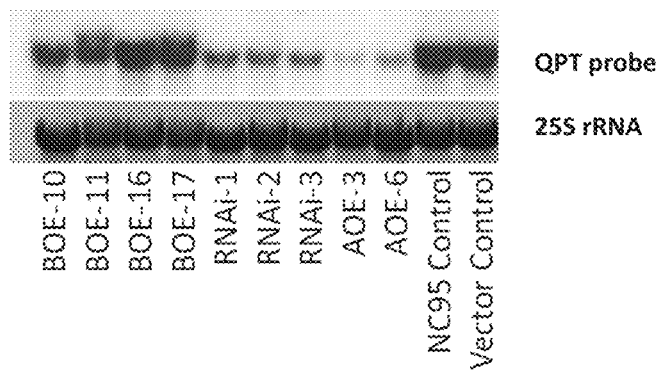
FIG. 9 shows QPT expression level in NtMYC2 a, or b over-expression and RNAi trangenic tobacco lines. Northern blot hybridization uses partial QPT coding sequence as probes. The rRNA stained with EtBr in gel is shown at the lower panel as an RNA loading reference.
Figure 10:
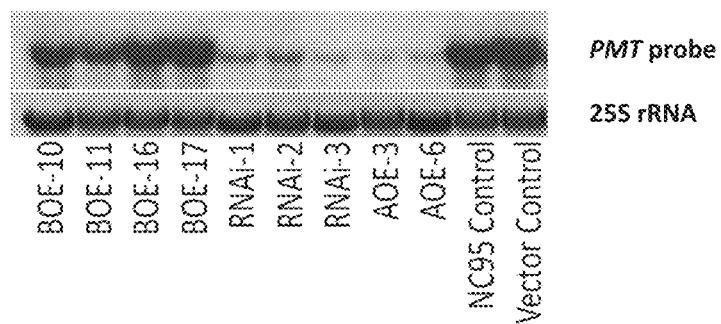
FIG. 10 shows PMT expression in NtMYC2a, or b over-expression and RNAi trangenic lines. Northern blot hybridization using partial PMT coding sequence as probes. The rRNA stained with EtBr in gel is shown in the lower panel as an RNA loading reference.
Figure 11A:
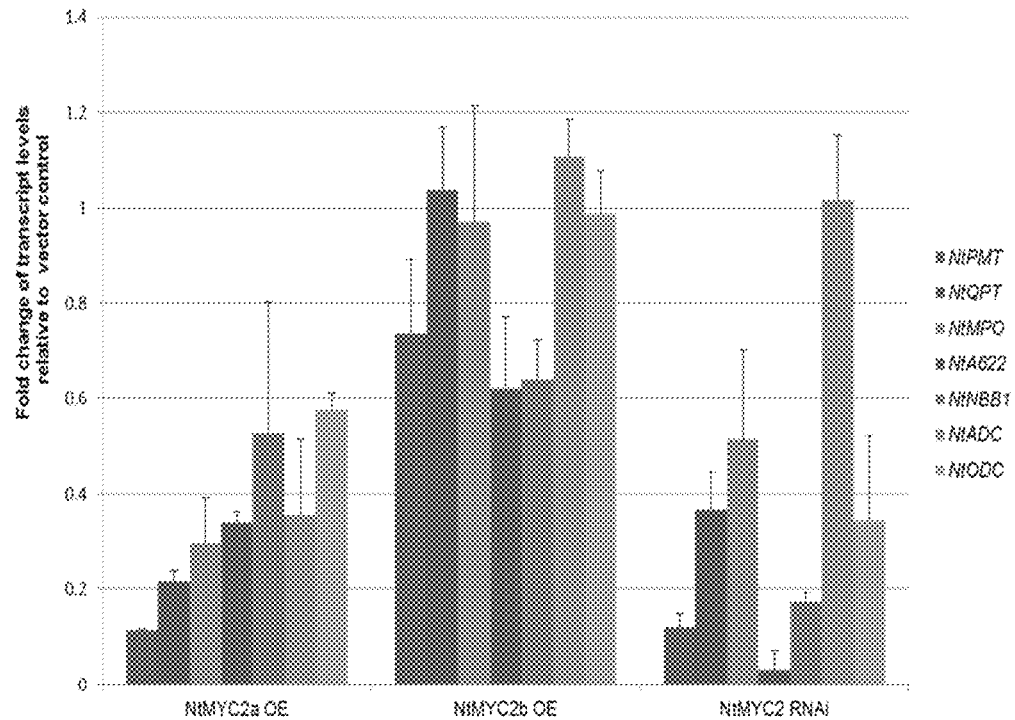
FIGS. 11A-11B show expression of nicotine biosynthesis pathway genes measured by qRT-PCR. The expression level in the vector control was set to 1, and expression of pathway genes in $T_0$ transgenic plants (FIG. 11A) and $T_1$ plants (FIG. 11B) is shown relative to this level. The average expression level of two transformation events from each construct that affects the nicotine level most is shown; the error bars indicate standard errors.
Figure 11B:
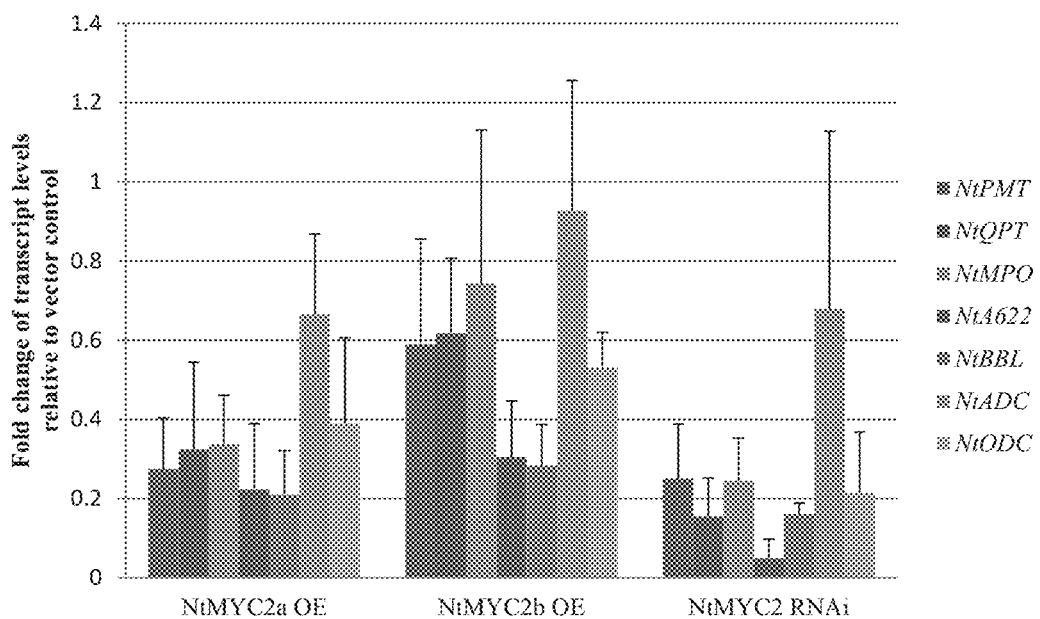

Because over-expression and knock down of the NtMYC2 genes altered both the nicotine and total akaloid levels (data not shown), selected over-expression and RNAi lines were subjected to Northern blot hybridization analysis and qRT-PCR analysis to evaluate the effects on nicotine biosynthesis pathway genes' expression. FIGS. 9, 10 and 11 show the expression of OPT and PMT genes as affected by the two transcription factors.

Over-expression of NtMYC2b did not alter the mRNA levels of the pathway genes with the exception of moderate expression reduction of the NtPMT, NtA622 and NtNBB1 genes. However, the expression of all pathway genes was reduced by over-expression of NtMYC2a. RNAi silencing of both NtMYC2 genes resulted in decrease of the expression levels of all pathway genes except NtADC.

Surprisingly, the steady-state mRNA levels of all seven pathway genes in NtMYC2a over-expression lines (AOE-3 and AOE-6) were lower than control, with NtQPT NtMPO and NtADC even lower than in the RNAi lines. In contrast, changes at mRNA levels of these genes in NtMYC2b over-expression lines were not obvious except for NtA622 and NtNBB1, expressions of which were about 60% of the control's (FIG. 5). Interestingly, among these seven genes investigated, NtADC expression levels were only reduced in AOE lines and virtually not affected in RNAi and BOE lines. Considering it is not a nicotine biosynthesis-dedicated gene, it is sensible that its expression is also regulated by another transcription circuit.

From the data on over-expression and RNAi lines, it is evident that NtMYC2a and/or NtMYC2b genes modulate nicotine biosynthetic pathway gene expression and nicotine level. It is more remarkable that in the three RNAi lines (RNAi-1, -2, and -3) which had NtMYC2 expression substantially decreased, both PMT and QPT mRNA levels were reduced by approximately ten-fold, and the nicotine level decreased about five-fold. More interestingly, although NtMYC2a and NtMYC2b are highly homologous, their functions appear to be diverse: Over-expression of NtMYC2a led to greatly reduced PMT and QPT mRNA levels yet the highest nicotine level (more than two-fold of the controls' and around 1% leaf dry weight) whereas over-expression of NtMYC2b caused little change in PMT and QPT mRNA levels among the four lines analyzed while nicotine concentration had a moderate increase (nearly 50%) in three out of the four lines. Moreover, it is surprising to see that plants having the highest nicotine level (AOE-3 and -6) were the ones with the lowest PMT and QPT mRNA levels, and plants with the lowest level of nicotine (RNAi-1, -2, and -3) had slightly more nicotine (but much reduced in comparison to the controls), and PMT and QPT mRNA. The data suggest that the nicotine level may not necessarily be associated with PMT and QPT mRNA levels.

Figure 12:
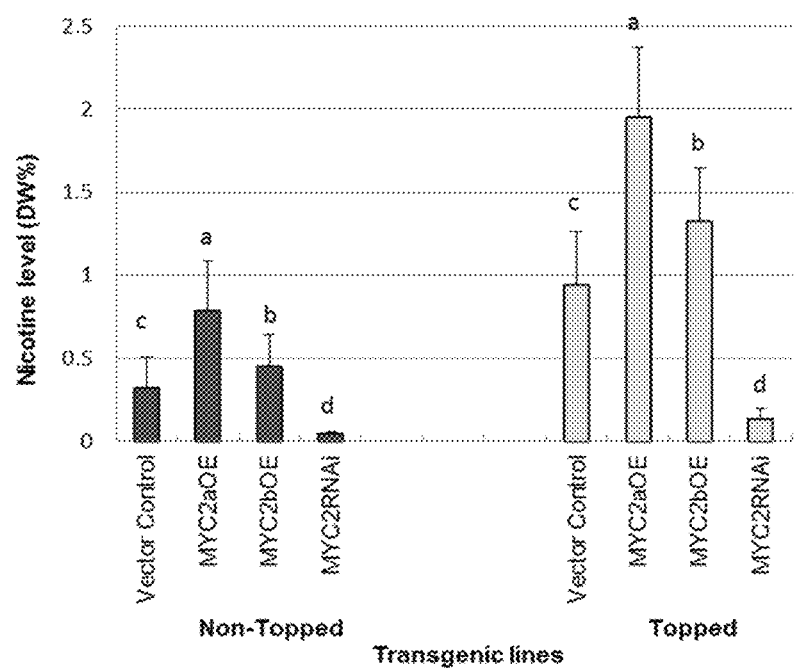
FIG. 12 shows leaf nicotine levels in $T_1$ transgenic plants under non-topping and topping treatments. DW %: dry weight percentage. Values are average of $T_1$ transgenic plants (PCR positive, n=15-30) from each group with standard errors. Different letters indicate significant difference within each category (t-test, p<0.05).

E. Inheritance of Nicotine Content in $T_1$ NtMYC2a and NtMYC2b Transgenic Lines To further evaluate the functions of both NtMYC2 genes and the related trait inheritance, $T_1$ plants from lines of AOE-3, AOE-6, BOE-16, BOE-17, RNAi-1, RNAi-2, and vector control were grown in greenhouse for about two months and PCR was used to screen out the non-transgenic segregates. Leaf nicotine level was measured in non-topped plants and plants 10 days after topping separately. The results showed that non-topped transgenic NtMYC2aOE (AOE-3 and AOE-6) plants, in average, had 2.4 folds of nicotine level of the vector control while NtMYC2bOE lines (BOE-16 and BOE-17) had 1.4 folds of nicotine content. RNAi (RNAi-1 and RNAi-2) plants contained only 14% nicotine content of the vector control plants. Similar increases were observed in the topping treatment. These results (FIG. 12) are highly consistent with those of $T_0$ plants (FIG. 8), indicating that the gained trait was inherited.

In both treatments, nicotine level in NtMYC2aOE plants was shown to be significantly higher than that in NtMYC2bOE plants (p<0.0001), indicating these two closely-related paralogs function differentially in nicotine biosynthesis.

F. Contents of Other Alkaloids in T1 NtMYC2a and NtMYC2b Over-Expression Lines

Figure 13:
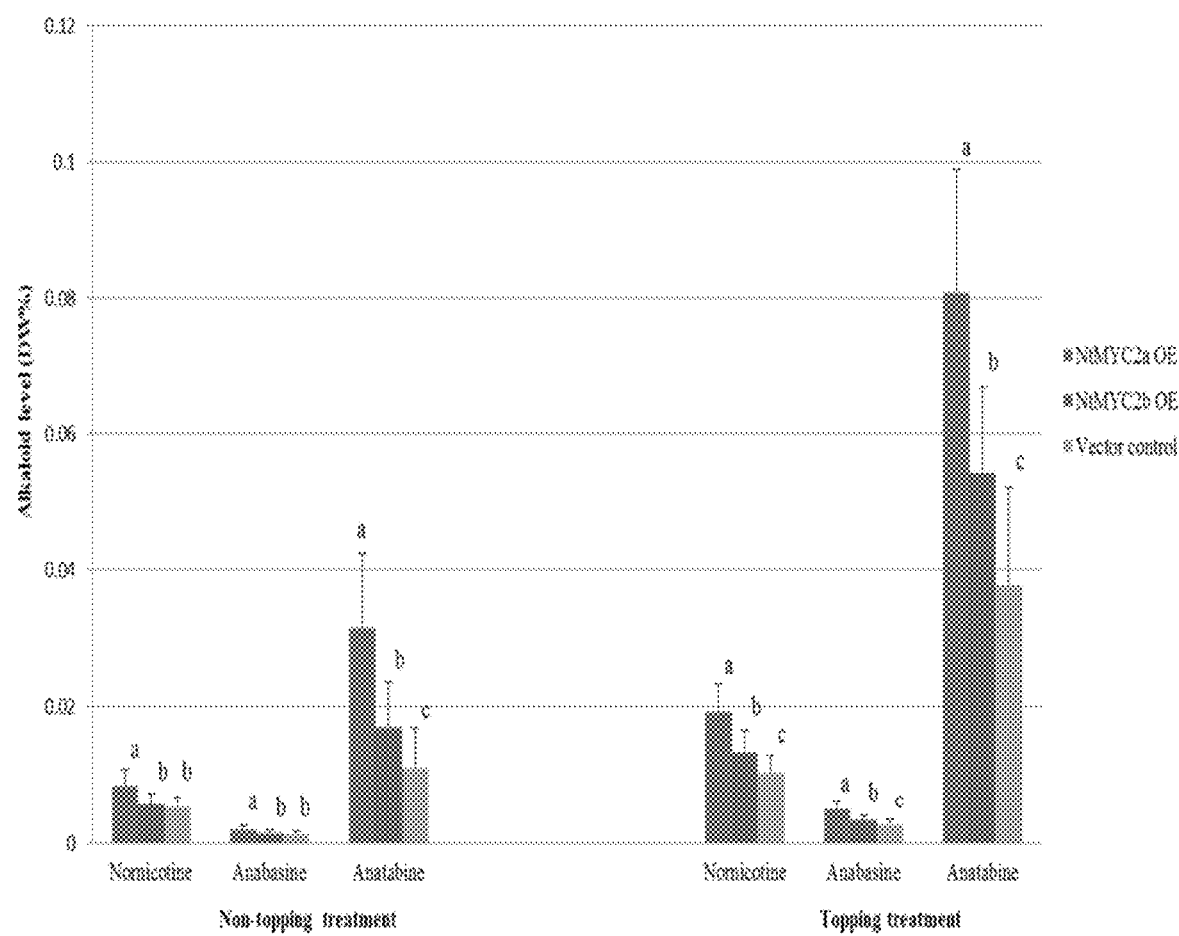
FIG. 13 shows nornicotine, anabasine and anatabine levels in leaf of T1 transgenic plants. DW %: dry weight percentage. Values are average of T1 transgenic plants (PCR positive, n=15-30) from each group with standard deviations. Different letters indicate significant difference within each category (t-test, p<0.05).

The contents of nornicotine, anabasine and anatabine were also tested in T1 plants of AOE-3, AOE-6, BOE-16, BOE-17 and vector control lines (see, FIG. 13).

As shown in FIG. 13, with topping, the levels of each of these alkaloids increased significantly in both NtMYC2a and NtMYC2b over-expression lines compared to vector control. When the plants were not topped, only anatabine had significant increase in NtMYC2a and NtMYC2b over-expression lines. Nornicotine and anabasine were significantly increased only in NtMYC2a but not NtMYC2b over-expression lines. Overall, the contents of all three alkaloids in NtMYC2a OE plants were significantly higher than those in NtMYC2b OE lines with both non-topping and topping treatments.

Example 4. Transcription Factor NtERF98

The full-length ERE transcription factor cDNA was 1019 bp in length and encodes a protein of 257 AA. The role this gene plays in the nicotine biosynthesis has not been reported.

A. Expression Pattern of NtERF98 in Different Organs of the Plant

Figure 14:
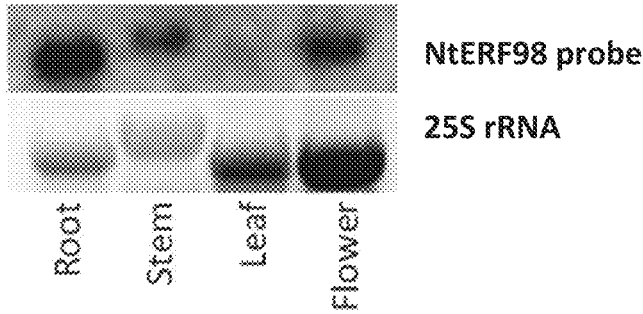
FIG. 14 NtERF98 expression in four organs of tobacco plant. Northern blot hybridization of total RNA isolated from various organs of fully grown plant was probed with a partial NtERF98 coding sequence. The 25S rRNA stained with EtBr in gel was also shown as a loading reference.

The expression pattern of NtERF98 in root, stem, leaf, and flower in wild type NC95 tobacco plants were examined. FIG. 14 shows that NtERF 98 was mainly expressed in the root, stem, and flower, and had little expression, if any, in leaves.

Figure 15:
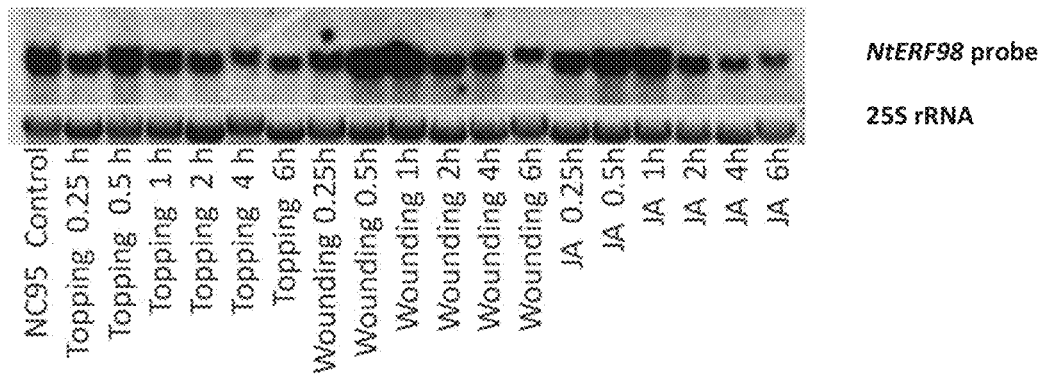
FIG. 15 shows a time course of NtERF98 expression in tobacco roots after topping, wounding, or MeJA treatment. Northern blot was hybridized with NtERF98 coding sequence as a probe, and 25S rRNA with EtBr staining as a loading reference.

B. Expression Pattern of NtERF98 Under Treatments of Topping, Wounding, and MeJA Since nicotine accumulation is induced by topping, wounding, and JA treatment, these three treatments were applied individually in this study to test whether NtERF98 expression was also affected by these treatments. Root tissues were collected 0.25 h, 0.5 h, 1 h, 2 h, 4 h and 6 h after treatments. FIG. 15 shows the gene expression pattern in roots of the treated tobacco plants.

NtERF98 expression under these three treatments had a similar biphasic decline pattern. The steady-state NtERF98 mRNA level was reduced within 15 min after initiation of each of these treatments. From 0.25 h to 0.5 h, the expression level increased up to the basal level of the wild type control in all three treatments. After 0.5 h, the mRNA levels were in decline again in the topping and wounding treatments. In MeJA treatment, the expression level reached its peak at 1 h, and declined thereafter.

C. Analysis of Transgenic Overexpression Lines

Figure 16:
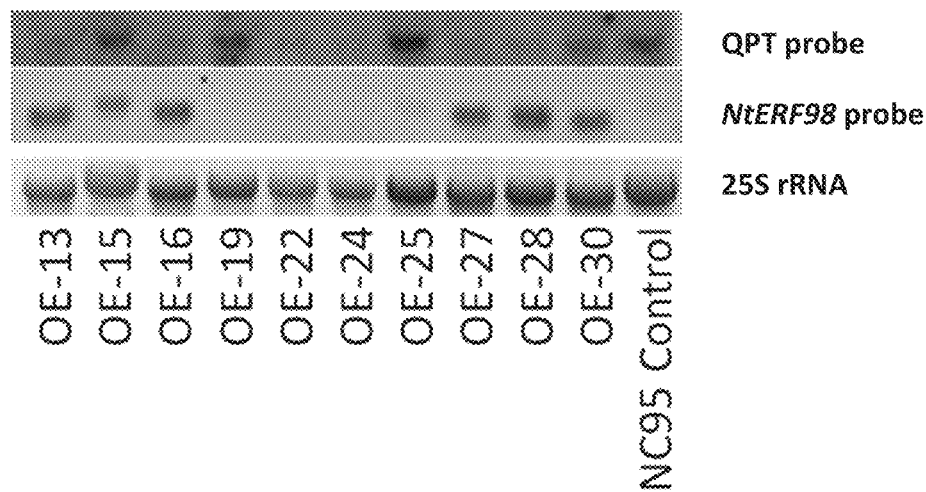
FIG. 16 shows NtERF98 and QPT expression in ten putative NtERF98 over-expression transgenic plants. Northern hybridization of QPT (top) and NtERR98 mRNA (middle) is shown, 25S rRNA stained with EtBr is also shown as a loading reference (bottom).

FIG. 16 shows the Northern analysis of NtERF98 and QPT in NtERF98 putative over-expression lines. Six out of 10 lines showed much higher expression level of NtERF98. Among the six NtERF98 over-expression lines, five had reduced QPT expression. OE-19 and OE-25 showed similar pattern of expression of these two genes as the control plant, which had very low expression of NtERF98 and high expression of QPT. A negative correlation seems to exist between the expression pattern of NtERF98 and QPT in most of the transgenic plants that over-expressed NtERF98.

Figure 17:
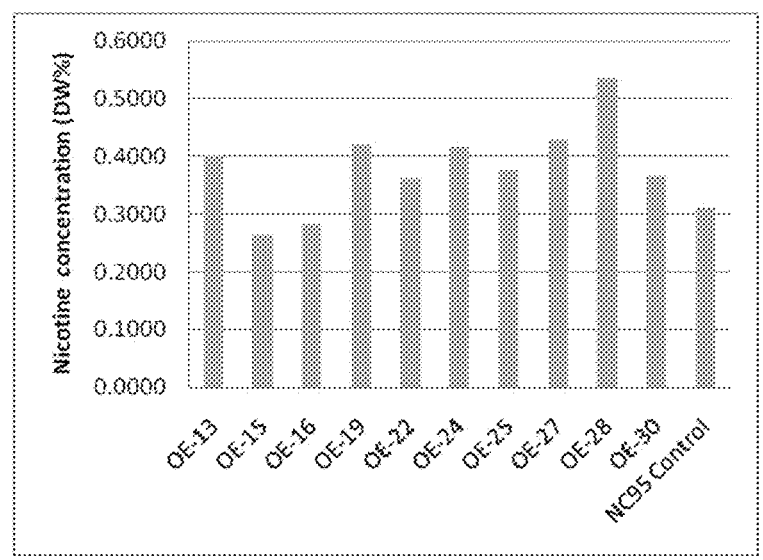
FIG. 17 shows nicotine concentration in ten NtERF98 over-expression transformed tobacco lines and wild type control. DW: dry weight.

Leaf nicotine concentration of all the transformed lines were determined. FIG. 17 shows that the nicotine levels in the transformed over-expression lines of NtERF98 increased except for the OE-15 and OE-16 lines, which exhibited slight reductions. No apparent correlation was found between the nicotine concentration and the NtERb98 or QPT expression level.

D. Analysis of NtERF98 Transgenic RNAi Lines

Figure 18:
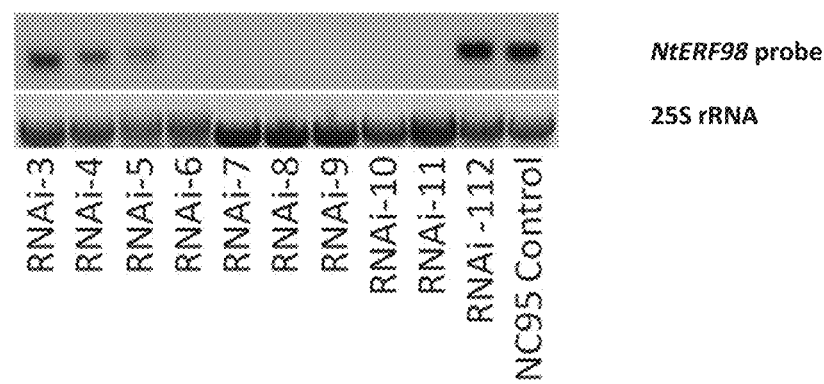
FIG. 18 shows Northern analysis of NtERF98 expression in its RNAi transgenic lines. The 25S rRNA stained with EtBr is shown as a loading reference.

A PCR fragment of 309 bp from NtERF98 coding sequence was used to make the RNAi construct. Northern analysis was performed to evaluate whether the knockdown of NtERF98 has an effect on the QPT expression. FIG. 18 shows that, out of 10 transformed lines, six had the NtERF98 expression completely repressed (RNAi-6 through -12), and the other four had slightly or moderately reduced expression.

Figure 19:
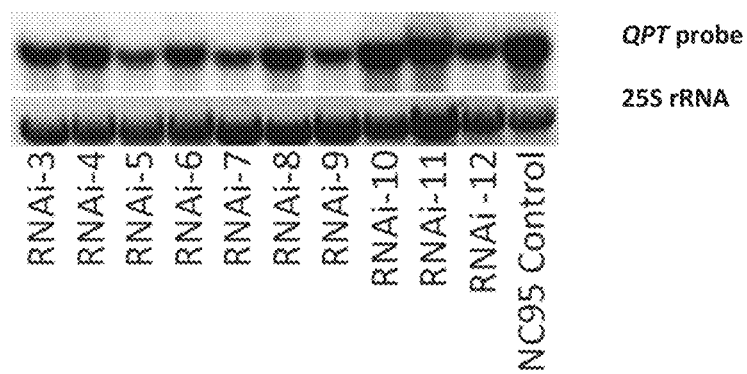
FIG. 19 shows Northern hybridization of QPT expression in the NtERF98 RNAi transformed tobacco lines. The 25S rRNA stained with EtBr is shown in the lower panel as a loading reference.
Figure 20:
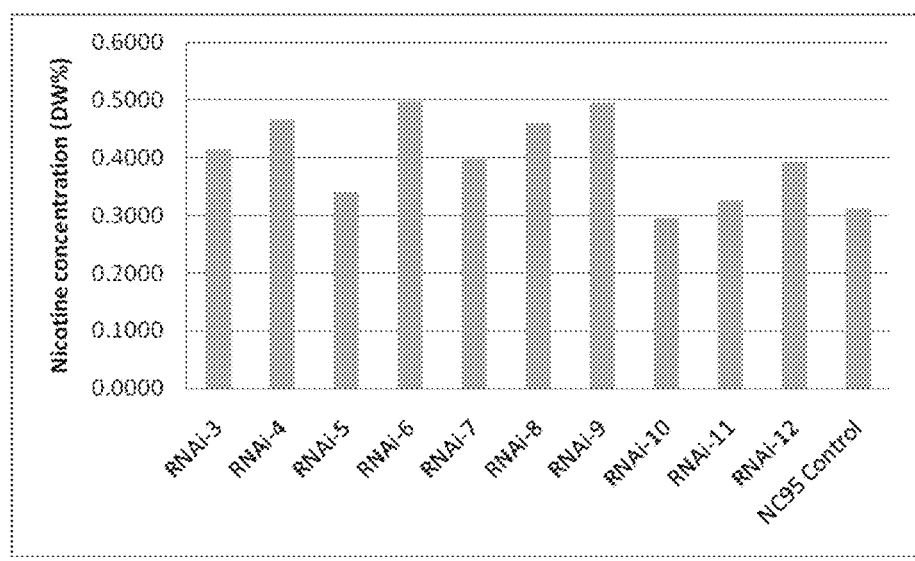
FIG. 20 shows nicotine concentration in NtERF98 RNAi transgenic tobacco lines and wild type control. DW: dry weight.

Northern analysis of QPT gene expression of the NtERF98 RNAi lines was performed. FIG. 19 shows the QPT expression in the RNAi plants when compared to a control plant. Various degree of reduction in QPT expression was observed among the transgenic plants. However, when nicotine concentration was examined, seven out of ten RNAi plants had moderate increase in nicotine level (30-60% higher) with the other three having levels similar to that of the non-transgenic control (FIG. 20).

Overall, NtERF98 appears to play a role in modulating QPT expression. It is intriguing that both over-expression and suppression of its expression generally led to a reduction of the QPT mRNA level and to a slight to moderate increase of nicotine concentration. The observation underscores the complex nature of the regulation of the nicotine biosynthesis pathway. Investigation of the relevant gene expression and nicotine level of the transgenic plants after topping or wounding treatment may provide more insight into the role of NtERF98 in nicotine biosynthesis.

Example 5. Transcription Factor NtETTa

The full length cDNA sequence of the transcription factor NtETTa gene was 2429 bp in length and encodes a protein of 739 AA. The cloned TF factor gene was named NtETTa.

A. Expression Pattern of NtETTa in Tobacco Plant

Figure 21:
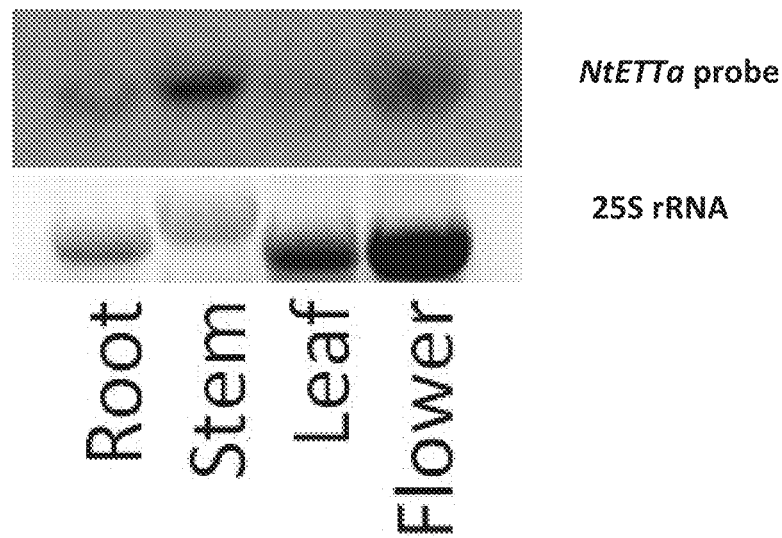
FIG. 21 shows a Northern blot analysis of NtETTa expressions in tobacco root, stem, leaf, and flower. The 25S rRNA stained with EtBr on the gel is shown as a loading reference.

The expression of the NtETTa gene in mature tobacco plant was examined by Northern analysis. FIG. 21 shows that it has higher expression in stem and low expression in root, leaf, and flower.

B. NtETTa Expression in Tobacco Root after Topping, Wounding, or MeJA Treatment

Figure 22:
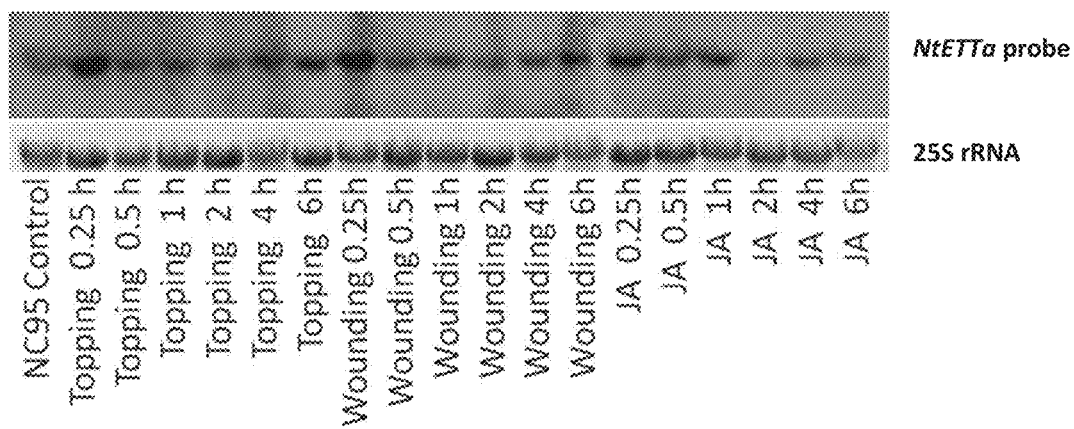
FIG. 22 shows a time course of NtETTa expression response in tobacco root after topping, wounding, or MeJA treatment. Shown are the Northern blot hybridization of NtETTa (top panel) and the 25S rRNA stained with EtBr as a loading reference (bottom panel).

The three treatments were also applied to test the responses of the NtETTa gene expression in tobacco root. FIG. 22 shows a clear up-regulation of NtETTa gene expression 0.25 h after any of these treatments with mRNA level increased more by topping and wounding. However, unlike the MYC2 genes, no clear biphasic increase pattern was observed for NtETTa gene expression. MeJA seems to be the least effective treatment with respect to NtETTa induction.

C. Analysis of Transgenic Plants that Over- or Under-Express NtETTa Gene

Figure 23:
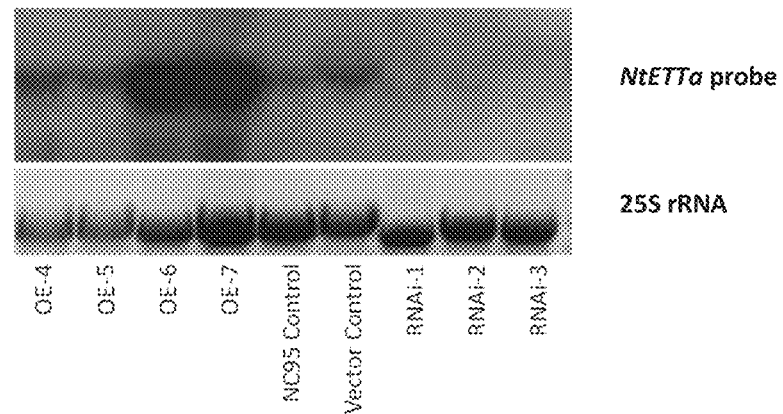
FIG. 23 shows expression levels of NtETTa in over-expression lines and RNAi lines. Shown are Northern hybridization of NtETTa (top panel) and the 25S rRNA stained with EtBr as a loading reference (bottom panel).

Four NtETTa over-expression and three RNAi transgenic tobacco lines were obtained. Northern blot analysis was undertaken to characterize these lines. FIG. 23 shows that all the four over-expression lines had higher NtETTa expression levels with OE-6 and OE-7 being much higher than the controls, and three RNAi lines showed almost no detectable expression.

Figure 24:
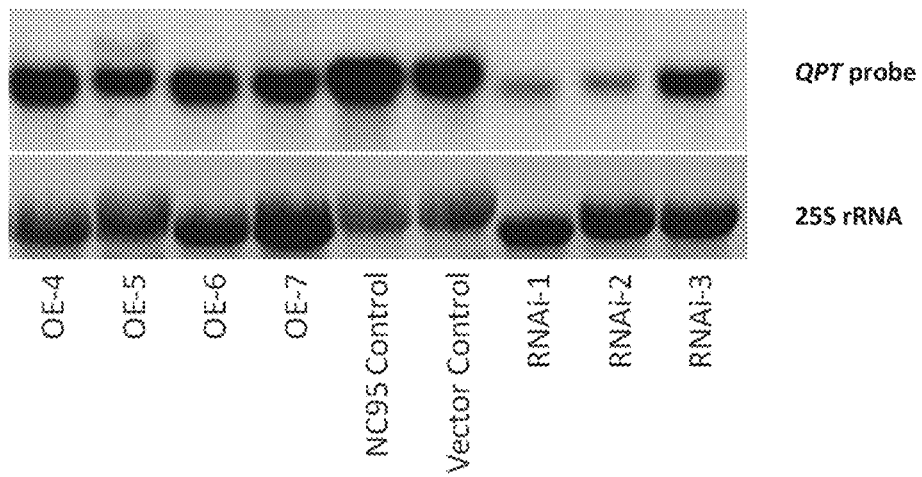
FIG. 24 shows QPT expressions in NtETTa over-expression and RNAi lines. Shown are Northern blot hybridization of QPT (top panel) and the 25S rRNA stained with EtBr as a loading reference (bottom panel).

To test the effect of NtETTa on QPT gene expression, Northern analysis of these over-expression and RNAi lines was performed. FIG. 24 shows that both NtETTa over-expression lines and RNAi lines had lower QPT expression levels when compared to the controls. Two RNAi lines (RNAi-1 and RNAi-2) exhibited the lowest QPT expression level.

Figure 25:
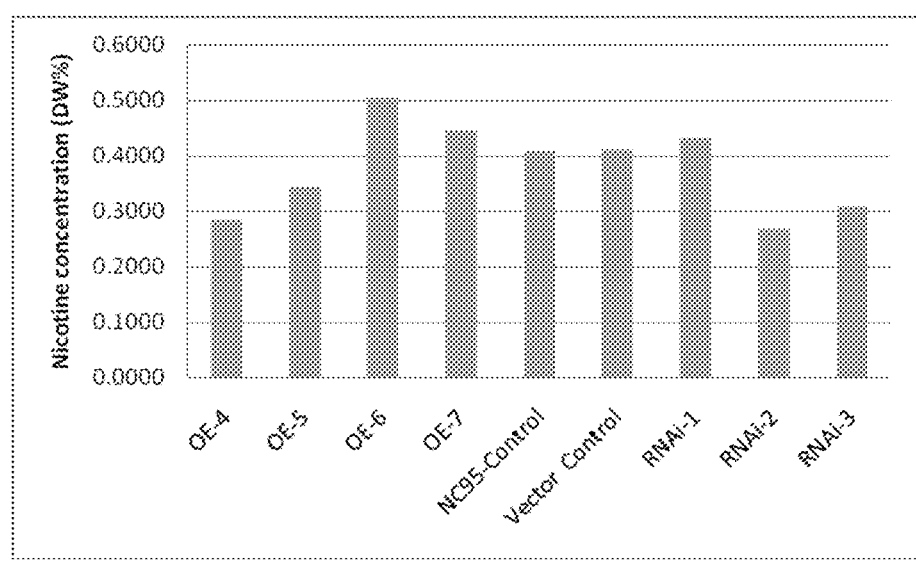
FIG. 25 shows nicotine concentrations of NtETTa over-expression and RNAi lines. The line numbers are the same as in the previous figures. DW: dry weight.

For all those lines, nicotine concentration in the leaf was determined. FIG. 25 shows that OE-4, -5 and RNAi-2, -3 had approximately 25% lower nicotine level than the controls while the nicotine concentration in OE-6 was slightly higher (25%).

The expression of the ARE transcription factor gene isolated in this experiment, NtETTa, was quickly induced by topping, wounding, and MeJA treatment. It affects QPT expression as revealed in either over-expression or RNAi transgenic lines. It was shown in RNAi-1 and -2 lines that suppression of NtETTa expression could lead to severe reduction of QPT mRNA level but only limited change in nicotine level. This again points to the complicated control of nicotine biosynthesis, and to our previous observation that nicotine level may not be correlated to QPT (and possible PMT) mRNA level. Additional experiments to determine the effect of stimulations like topping, wounding, or MeJA treatment on the transgenic plants (in terms of PMT and QPT mRNA levels and the nicotine accumulation), should elucidate the role of NtETTa in nicotine biosynthesis pathway further.

Example 6. Characterization of T3 Transgenic Plants

A Greenhouse Grown T3 Plants (NC-GH-2013)

T3 plants of AOE and BOE events were grown in a greenhouse from seed of T2 plants of events AOE3, AOE6, BOE16 and BOE17. The seeds were planted in 288 cell trays in an improvised float system in greenhouses. Individual T3 plants of each subfamily were tested for the presence of a T-DNA insert gene by PCR analysis for the marker gene to determine the segregation pattern. Non-segregating subfamilies were identified for events AOE3 (AOE3-46-68), AOE6 (AOE6-30-77), and BOE16 (BOE6-37-93, BOE16-37-94) and plants from these subfamilies comprised 4 of the sets in the trial. Three additional sets included in the trial, AOE3-46(S), AOE6-30(S), and BOE17-12(S), consisted of PCR-positive plants from segregating seed lots. Two sets of control plants were included, a line transformed with a vector containing no MYC2 coding sequence (VC), and plants from seed from a cross of the vector control with untransformed tobacco (VC×NT)

Each set consisted of three plants. Seedlings were transplanted to 4 gal plastic bags with drainage holes punched in them containing approximately 14 liters of potting mix/bag.

Pre-topping leaf samples were taken 13 weeks after transplanting, and then the plants were topped. Additional leaf samples were taken 17 and 31 days after topping. Leaf samples were allowed to dry at RT for 10 days and then the leaf lamina were dried at 60° C. Dried leaf lamina was analyzed for total nicotinic alkaloids.

Figure 26A:
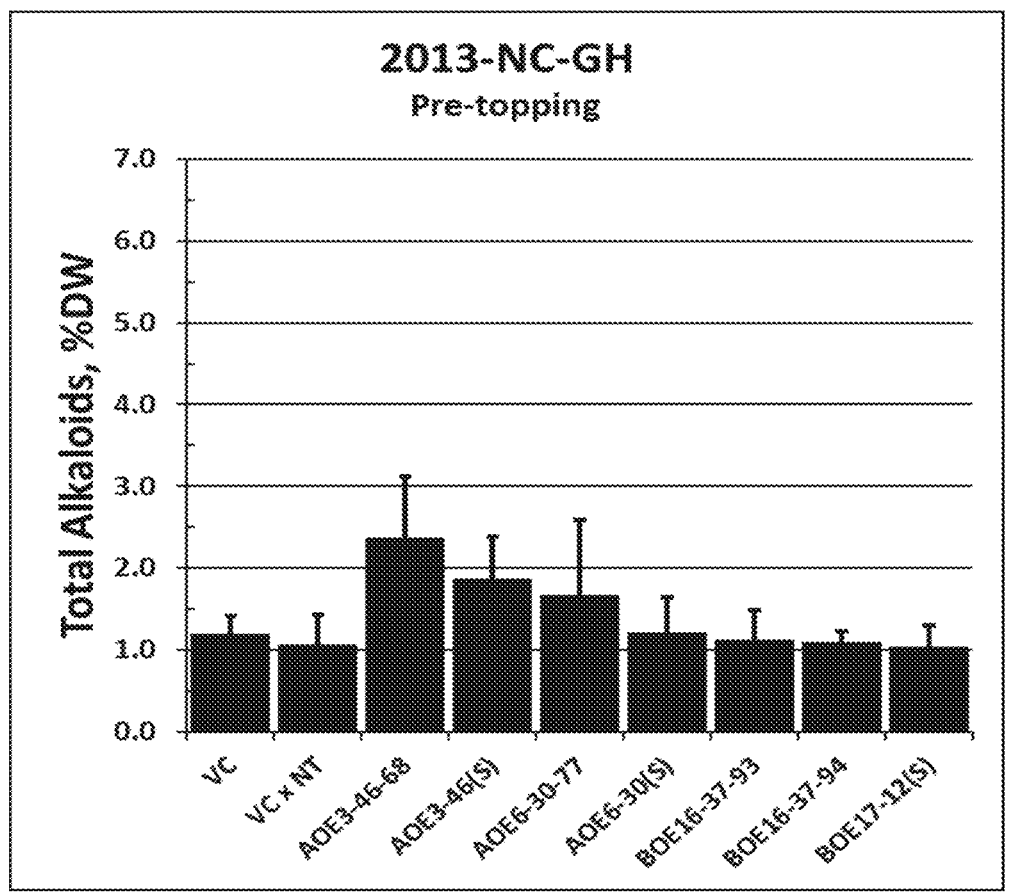
FIGS. 26A-26C show total alkaloid levels (% dry weight (DW)) in greenhouse grown T3 plants. Leaf samples were taken 13 weeks after transplanting and prior to topping, and at 17 and 31 days after topping. Two sets of control plants were included, a line transformed with a (VC=vector containing no MYC2 coding sequence), and VC×NT=plants from seed from a cross of the vector control with untransformed tobacco.
Figure 26B:
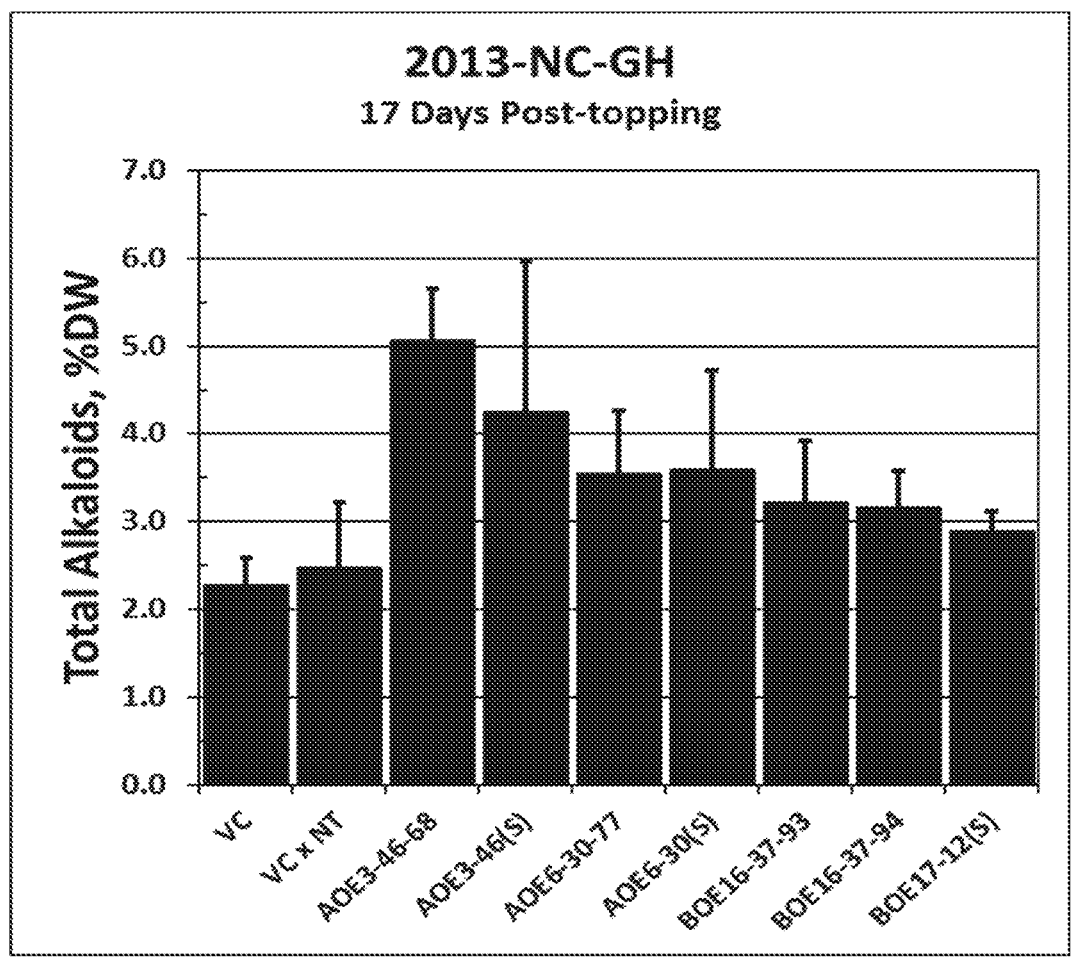
Figure 26C:
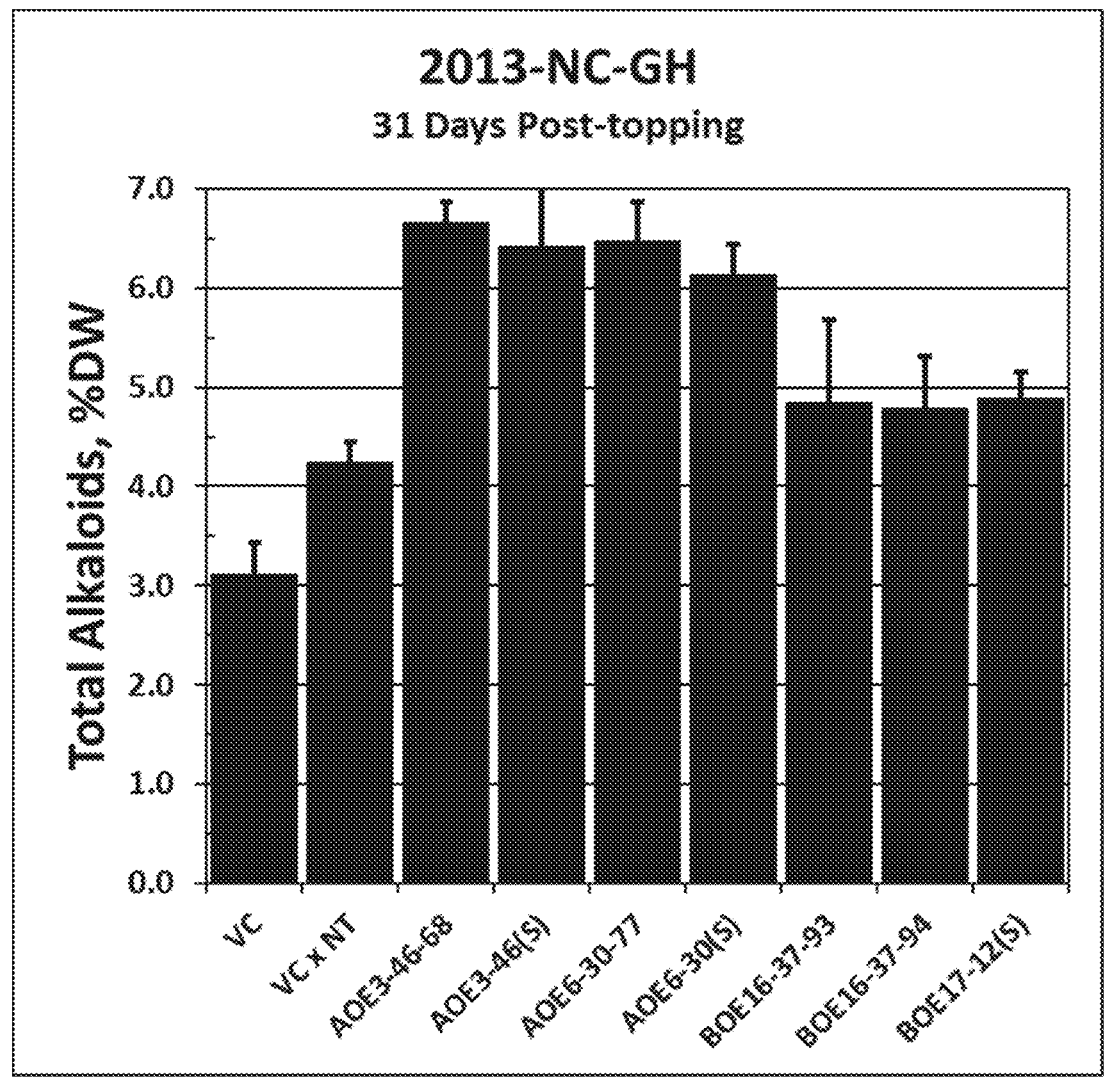

As shown in FIGS. 26A-26C, total alkaloid levels were higher in AOE plants both before and after topping. Total alkaloids in the BOE plants were similar to control levels prior to topping, but increased after topping.

B. Field Grown T3 Plants (2013-A4-1)

T3 plants of AOE and BOE events described above, were grown in the field. The trial included 10 sets of plants from the seedlings used in Example 6, part A, above, the two controls, VC and VC×NT, and 2 entries from each of the four transgenic events AOE3, AOE6, BOE16 and BOE17. Four entries, AOE3-46-68, AOE6-30-77, BOE16-37-93, and BOE16-37-94, were composed of plants from non-segregating seed lots. Four entries, AOE3-46(S), AOE6-30(S), BOE17-12(S1), and BOE17-12(S2), were composed of PCR-positive plants selected from segregating T3 seed lots. Each set was planted in 5 replicates of 3 plants each.

Leaf samples were taken prior to topping and 17 and 31 days after topping. Leaf samples were dried and total alkaloids in leaf lamina measured as in A.

Figure 27A:
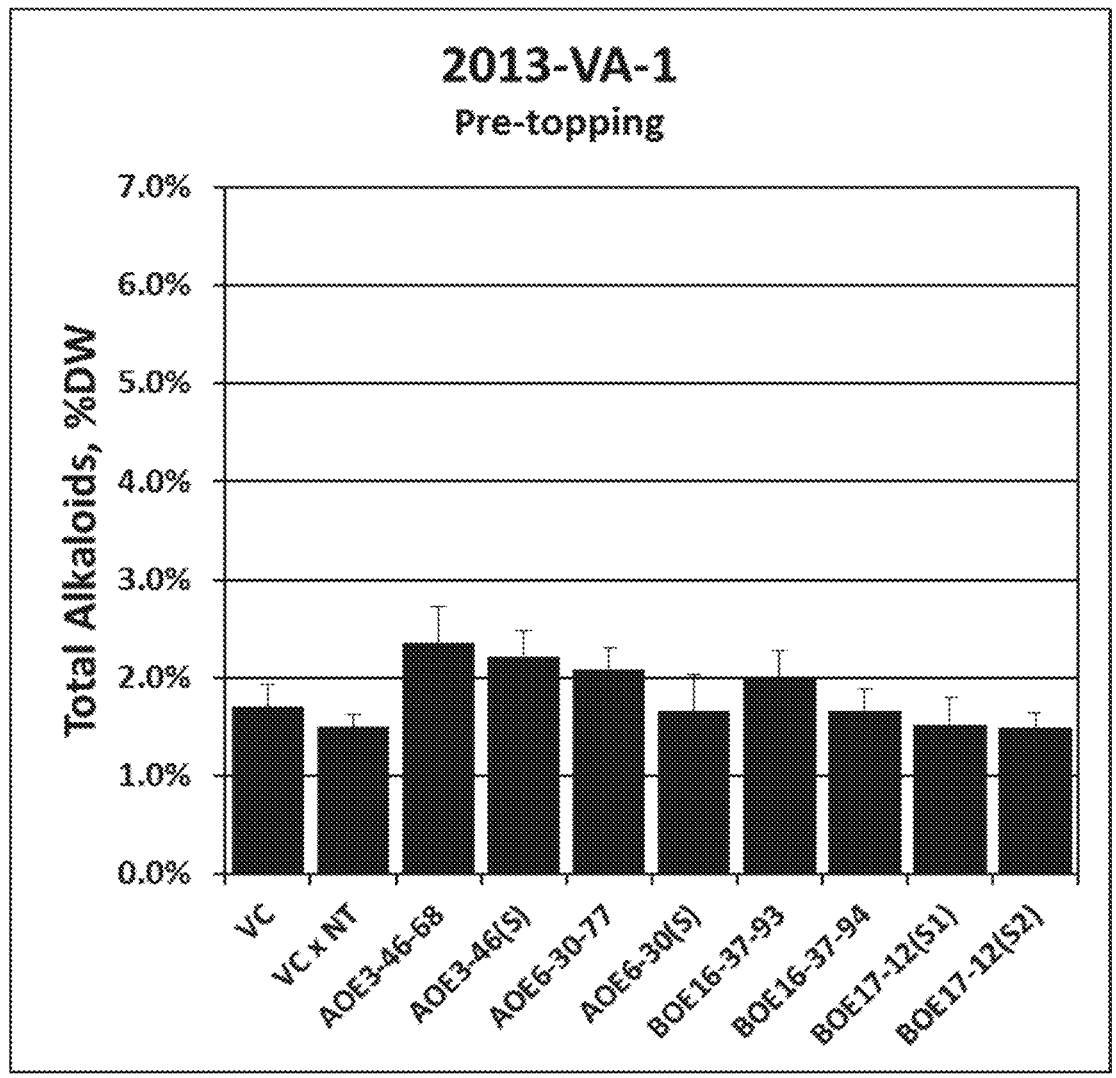
FIGS. 27A-27C show total alkaloid levels (% dry weight (DW)) in field grown T3 plants. Leaf samples were taken 13 weeks after transplanting and prior to topping, and at 17 and 31 days after topping. Two sets of control plants were included, a line transformed with a (VC=vector containing no MYC2 coding sequence), and VC×NT=plants from seed from a cross of the vector control with untransformed tobacco.
Figure 27B:
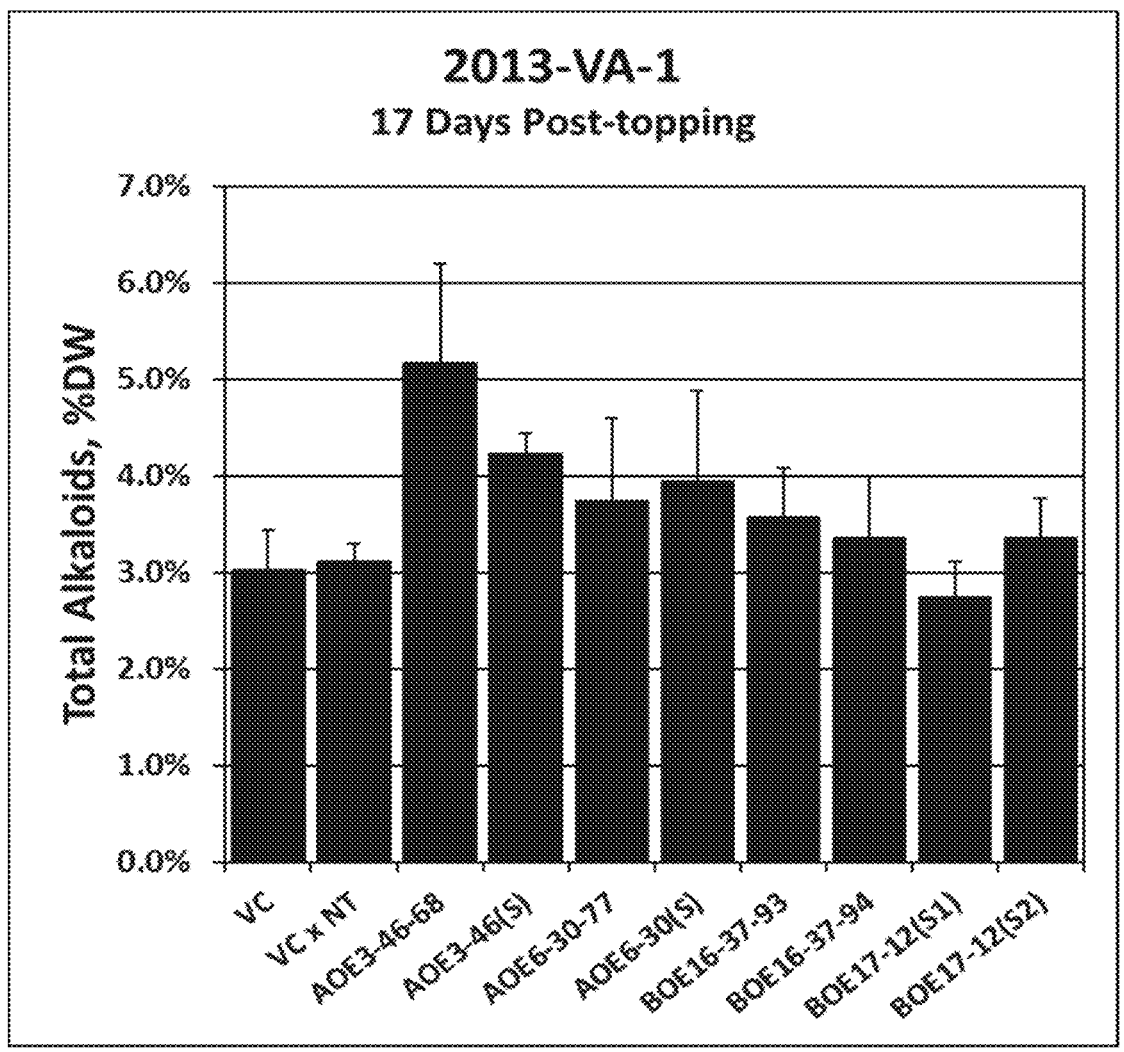
Figure 27C:
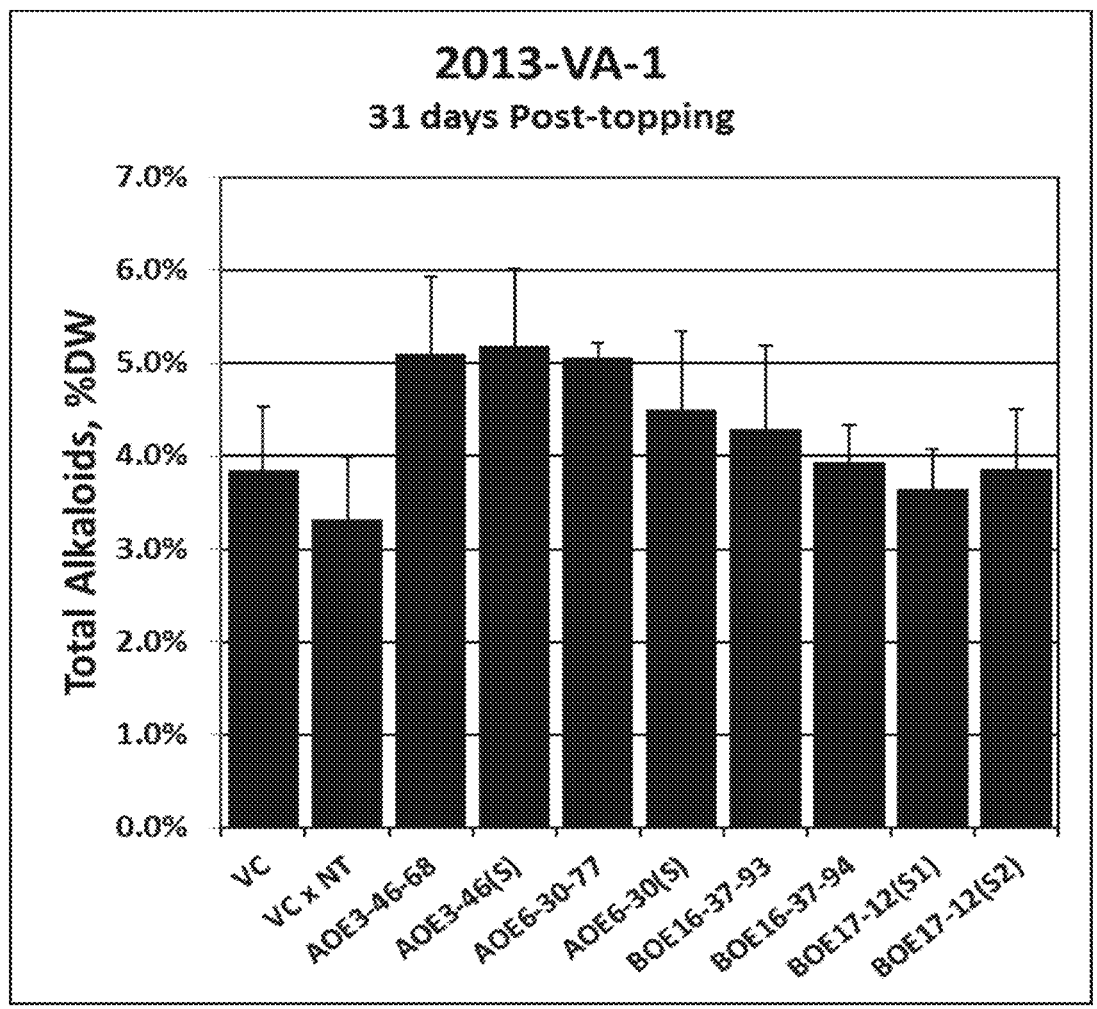

As shown in the FIGS. 27A-27C, total alkaloid levels were higher in AOE plants both before and after topping.

Example 7. Discussion

QPT2 Promoter and Yeast One-Hybrid Screening

Among the major nicotine synthesis-related genes, only the promoter sequence of NtPMT1a was analyzed in detail, and three basic transcription regulatory motifs were identified. They are a G-box (GCACGTTG, −103 to −96 bp from transcription initiation site), a GCC-like box (TGCGCCC, −62 to −56 bp) and an AT rich region in between (−80 to −69 bp, 92.8% A and T bases). These elements were demonstrated to be important in regulation of nicotine accumulation under JA treatment, and were named GAG motif (Timko et al. (2010). *Recent Advances in Tobacco Science* 36: 25-39). Although the GAG motif was found in all NtPMT gene promoters, a BLAST search could not identify such a motif in other gene promoters in public available database (Id), suggesting that the motif is a critical element required to coordinate expression of the NtPMT family members. It also implies that the expression of other nicotine synthesis pathway genes may not be regulated in the same way although their expression has to be somewhat coordinated to produce nicotine efficiently. The tobacco QPT2 gene promoter was used in this study as a bait to isolate transcription factors that bind to the QPT2 promoter and regulate its gene expression. The disadvantage is that the QPT2 gene promoter has not previously been analyzed and characterized in detail. A sequence scanning analysis of the promoter found that a "G-box" sequence (AACGTG) lies at −205 bp upstream of the translational start site ATG as predicted by the web-based software (plantCARE, bioinformatics.psb.ugent.be/webtools/plantcare/html/).

In the yeast one-hybrid system, a library of proteins fused with the activation domain of GAL4 are screened by their binding to the bait promoter sequence and activates the reporter gene expression (His3 in this case). As recommended in the user manual, at least three tandem copies of the target sequence (bait) should be included in the bait vector upstream of the reporter gene to increase the chance for binding. Usually, cis-elements less than 20 bp are used to make the tandem copies and the total bait is around 100 bp long. In this study, because the QPT promoter region was not well characterized, the 1 kb QPT2 gene promoter was used as a bait. A total of around 100 positive colonies were isolated and their sequences were determined and analyzed. Three out of five TF genes isolated from the system have roles in regulating genes in the nicotine biosynthesis pathway.

Isolation of Four Transcription Factors Involved in Nicotine Biosynthesis

A total of four TFs were isolated, which are involved in the nicotine biosynthesis pathway. They modulate the QPT mRNA level and affect nicotine concentration. Their expression in roots is responsive to topping, wounding, and MeJA treatments in a similar manner: their expression levels change as quickly as within 15 min upon the treatments. NtMYC2a and 2b are positively induced by these treatments and showed two induction peaks within the first six hours after treatments. In contrast, whereas NtERF98 mRNA level was negatively regulated and exhibited biphasic decreases within six hours, NtETTa expression was also induced by the treatments within 15 min but did not show a clear biphasic pattern. The long-distance movement signal that causes such rapid changes (within 15 min) in gene expression level in roots is still unknown. Neither JA nor auxin seems to move that fast within plants (Hertel and Flory (1968) *Planta* 82: 123-144; Baldwin et al. (1997) *Planta* 201: 397-404; Shi et al. (2006) *J Exp Bot* 57: 2899-2907). From another perspective, wounding can induce production of smRNA. Recent research shows that silenced RdR1 (RNA directed RNA polymerase) in *Nicotiana attenuate* made the plants susceptible to herbivores (Pandey et al. (2008) *Proc Natl Acad Sci USA* 105:4559-4564). This result suggests that the smRNA is involved in the wounding-induced response of tobacco plant and may be a fast-moving signal candidate.

The fact that these TF genes are expressed in all the tissues tested is not surprising. Each of these TFs are likely involved in the JA signaling pathway, which regulates not only nicotine (or other alkaloids) biosynthesis, but also many other physiological and developmental processes, such as root growth, fertility, resistance to diseases and even responses to abiotic stress like drought (Kazan and Manners (2008) *Plant Physiol* 146: 1459-1468). Interestingly, despite their potential multiple roles in plant growth, transgenic plants with constitutive over-expression or down-regulation of each of these four TF genes all appeared normal when growing in greenhouse.

Transcription Factors NtMYC2a, NtMYC2b are Positive Regulators of Nicotine Biosynthesis MYC2 has been considered the core TF in JA signaling pathway by regulating a cascade of transcription factors in plant responses to JA. It is known that MYC2 binds to the G-box motif of a promoter (Dombrecht et al. (2007) *Plant Cell* 19: 2225-2245). Because all the PMT gene promoters contain the G-box (Timko et al. (2010) *Recent Advances in Tobacco Science* 36: 25-39) and the QPT promoter has a "G-box" sequence, it is likely that MYC2 directly regulates expression of these two key genes. In two over-expression lines of NtMYC2a, the constitutive nicotine level (untreated) was more than doubled attaining about 1% of leaf dry weight, which is very high. NtMYC2b also facilitated an approximately 50% increase in nicotine level in three over-expression lines. In contrast, three RNAi lines, in which it is likely that both NtMYC2a and b were down-regulated (the probe used in Northern blot analysis cannot distinguish the two), had approximately a five-fold decrease in nicotine level accompanied by approximate 10-fold decrease in mRNA levels of PMT and QPT genes. All indicate a positive regulator role of NtMYC2a and b in nicotine biosynthesis.

Notably, a dramatic decrease of both PMT and OPT mRNA levels in the NtMYC2a was observed in the over-expression lines. This may indicate a negative feedback loop when the nicotine level reaches a certain threshold level to prevent an uncontrolled accumulation (Kazan and Manners (2008) *Plant Physiol* 146: 1459-1468). Alternatively, although the mRNAs of PMT and OPT were down-regulated by an unknown mechanism related to NtMYC2a over-expression, their protein levels were increased or their enzymes were more active to enhance nicotine production. In addition, because PMT and OPT mRNA levels were not affected as much in the NtMYC2b over-expression lines, these results also reveal a possible diverse function between the 2a and 2b isoforms. The phenomenon may be explained by a negative regulatory loop found in *Arabidopsis*. Here, AtMYC2 was demonstrated to up-regulate repressor JAZ protein, which in turn binds, and represses the activity of, AtMYC2 (Staswick (2007) *Trends in Plant Sci* 13: 66-71). Similarly, high levels of NtMYC2b wouldn't be able to activate the PMT and QPT expression if it up-regulates NtJAZ expression.

Overall, NtMYC2b seems to be the "weaker" isoform between the two because in its over-expression lines its mRNA levels increased approximately 10-fold and the nicotine level was only enhanced by about 50%.

The TF genes, NbbHLH1 and NbbHLH2, from the same subgroup of the bHLH family were recently isolated and characterized in *N. benthamiana* (Todd et al. (2010) *Plant J* 62: 589-600). NbbHLH1 shares 70% AA homology with the NtMYC2b while NbbHLH2 has 96% AA identity with NtMYC2a gene. NbbHLH1 and 2 bind at the G-box sequence of the NbPMT gene promoter, and positively regulate nicotine biosynthesis in transgenic tobacco plants. However, Todd et al. (Id.) were also puzzled by the observation of little change or even reduction of mRNA levels of most nicotine biosynthesis genes, including QPT, in NbbHLH1 and NbbHLH2 over-expression transgenic tobacco plants. This report verifies that our observation was not an exception or experimental error, and points to a more complicated regulatory network in nicotine biosynthesis pathway.

Zhang et al. (2012) also reported isolation and characterization of three related NtMYC2 genes: NtMYC2a, 2b and 2c, among which 2b and 2c have identical amino acid sequences but are diverse in nucleotide sequence. However, after AA sequence examination, the NtMYC2a and 2b they reported (GenBank No. HM466974 and HM466975) have been shown to be the same transcription factors as NtMYC1b (ADH04268) and NtMYC1a (ADH04267), respectively, and not NtMYC2a and NtMYC2b.

Possible Roles of Transcription Factors NtERF98 and NtETTa in Nicotine Biosynthesis The ethylene and JA signaling interaction is rather complex and could be both synergistic and antagonistic (Kazan and Manners (2008) *Plant Physiol* 146: 1459-1468). Both repressor- and activator-type ethylene reaction factors (ERFs) have been reported (McGrath et al. (2005) *Plant Physiol* 139: 949-959). In tobacco, ethylene is shown to have negative effects on nicotine biosynthesis (Wang et al. 1994; Shoji et al. (2000) *Plant Cell Physiol* 41: 1072-1076; Winz and Baldwin (2001) *Plant Physiol* 125: 2189-2202). Our research revealed that NtERF98 has a rather complicated role in nicotine biosynthesis. NtERF98 is a negative regulator of nicotine synthesis in that its expression is down-regulated by all three treatments that stimulate nicotine synthesis and that the nicotine levels increased by up to 50% in a majority of its RNAi lines. In addition, there was a good negative correlation between NtERF98 and QPT mRNA levels in most of the over-expression lines. However, in those lines, while QPT was down-regulated, nicotine level was unchanged or increased only moderately. Moreover, in the RNAi lines where nicotine levels were generally increased, the QPT mRNA levels were reduced slightly. Overall NtERF98 may have a modifying function on nicotine level but may be more responsible for modulating QPT mRNA level. This TF may be involved in the tight control of QPT mRNA level The auxin and JA signaling pathways are closely interlinked. It has been shown that one phytohormone activates biosynthesis genes of the other and vice versa. Moreover, at least two ARFs are required for JA biosynthesis and plant fertility (for review, see Kazan and Manners (2008) *Plant Physiol* 146: 1459-1468). Recently it was reported that the JAZ1 repressor gene is activated by both JA and auxin (Grunewald et al. (2009) *EMBO Rep.* 10: 923-928). In the present invention, the cloned ARF TF gene, NtETTa, appears to positively regulate QPT expression as shown in the RNAi lines where OPT mRNA was reduced approximately 15 fold, indicating that NtETTa is required for QPT expression. However, over-expression of NtETTa did not increase QPT expression and often moderately reduced its mRNA level, implicating a role of NtETTa in the complicated tight control of QPT mRNA level.

Recently, an auxin responsive transcription factor, NbARF1, was reported as a negative regulator in nicotine synthesis. Suppression of NbARF1 by VIGS significantly enhanced nicotine level in untreated plants (Todd et al. (2010) *Plant J* 62: 589-600). NtETTa is an auxin responsive transcription factor but it acts as a positive regulator on QPT expression, although it appears to have minor effects on nicotine level.

In conclusion, four TF genes were cloned in this study. They are NtMYC2a and NtMYC2b from the bHLH family, NtERF98 from the AP2/ERF family, and NtETTa from the ARF family. They are all involved in regulation of root QPT mRNA level and/or leaf nicotine level, with NtMYC2a and NtMYC2b having a more positive effects, and NtERF98 and NtETTa being rather more complicated modulators. NtMYC2a appears to play a more important role in regulating nicotine synthesis: Over-expression increases constitutive nicotine level by up to 2.5-fold whereas down-regulation of the gene (together with NtMYC2b) reduces it by five fold. Our research also revealed that higher nicotine synthesis is not always associated with higher mRNA levels of a key pathway gene, QP7, pointing to a negative feedback loop and/or possible translational and/or posttranslational control in the pathway.

The foregoing is illustrative of the invention, and is not to be construed as limiting thereof. The invention is defined by the following claims, with equivalents of the claims to be included therein.

APPENDIX

Nucleotide and amino acid sequences of the transcription factors isolated in this research NtMYC2a cDNA (full-length, 2214 bp)
```
CACACACTCTCTCCATTTTCACTCACTCCTTATCACCAAACAATTCTTG
GGTGTTTGAATATATACCCGAAATAATTTCCTCTCTGTATCAAGAATCA
AACAGATCTGAATTGATTTGTCTGTTTTTTTTTCTTGATTTTGTTATAT
GGAATGACGGATTATAGAATACCAACGATGACTAATATATGGAGCAATA
CTACATCCGATGATAATATGATGGAAGCTTTTTTATCTTCTGATCCGTC
GTCGTTTTGGCCCGGAACAACTACTACACCAACTCCCCGGAGTTCAGTT
TCTCCAGCGCCGGCGCCGGTGACGGGGATTGCCGGAGACCCATTAAAGT
CTATGCCATATTTCAACCAAGAGTCACTGCAACAGCGACTCCAGACTTT
AATCGATGGGGCTCGCAAAGGGTGGACGTATGCCATATTTTGGCAATCG
TCTGTTGTGGATTTCGCGAGCCCCTCGGTTTTGGGGTGGGGAGATGGGT
ATTATAAAGGTGAAGAAGATAAAAATAAGCGTAAAACGGCGTCGTTTTC
GCCTGACTTATCACGGAACAAGCACACCGGAAAAAGGTTCTCCGGGAG
CTGAATTCTTTAATTTCCGGCACACAAACCGGTGGTGAAAATGATGCTG
TAGATGAAGAAGTAACTGATACTGAATGGTTTTTTCTGATTTCCATGAC
ACAATCGTTTGTTAACGGAAGCGGGCTTCCGGGCCTGGCGATGTATAGT
TCAAGCCCGATTTGGGTTACTGGAACAGAGAGATTAGCTGTTTCTCACT
GTGAACGGGCCCGACAGGCCCAAGGTTTCGGGCTTCAGACTATTGTTTG
TATTCCTTCAGCTAATGGTGTTGTTGAGCTCGGGTCAACTGAGTTGATA
TTCCAGACTGCTGATTTAATGAACAAGGTTAAAGTTTTGTTTAATTTTA
ATATTGATATGGGTGCGACTACGGGCTCAGGATCGGGCTCATGTGCTAT
TCAGGCCGAGCCCGATCCTTCAGCCCTTTGGCTGACTGATCCGGCTTCT
TCAGTTGTGGAAGTCAAGGATTCGTCGAATACAGTTTCCTTCAAGCAATA
CCAGTAAGCAACTTGTGTTTGGAAATGAGAATTCTGAAAATGGTAATCA
AAATTCTCAGCAAACACAAGGATTTTTCACTAGGGAGTTGAATTTTTCC
GAATATGGATTTGATGGAAGTAATACTCGGTATGGAAATGGGAAGTCC
ATTCTTCGCGTTCTTGCAAGCCTGAGTCTGGTGAAATCTTGAATTTTGG
TGATAGTACTAAGAGGAGTGCTTGCAGTGCAAATGGGAGCTTGTTTTCG
GGCCAATACAGTTCGGGCCCGGGCCTGCGGAGGAGAACAAGAACAAGA
ACAAGAAAAGGTCACCTGCATCAAGAGGAAGCAACGATGAAGGAATCCT
TTCATTTGTTTCGGGTGTGATTTTGCCAAGTTCAAACACGGGGAAGTCC
GGTGGAGGTGGCGATTCGGATCAATCAGATCTCGAGGCTTCGGTGGTGA
AGGAGGCGGATAGTAGTAGAGTTGTAGACCCCGAGAAGAAGCCGAGGAA
ACGAGGGAGGAAACCGGCTAACGGGAGAGAGGAGCCATTGAATCATGTG
GAGGCAGAGAGACAAAGGAGGGAGAAATTGAATCAAGATTCTATGCAC
TTAGAGCTGTTGTACCAAATGTGTCAAAAATGGATAAAGCATCACTTCT
TGGTGATGCAATTGCATTTATCAATGAGTTGAAATCAAAGGTTCAGAAT
TCTGACTCAGATAAAGAGGACTTGAGGAACCAAATCGAATCTTTAAGGA
ATGAATTAGCCAACAAGGGATCAAACTATACCGGTCCTCCCCCGTCAAA
TCAAGAACTCAAGATTGTAGATATGGACATCGACGTTAAGGTGATCGGA
TGGGATGCTATGATTCGTATACAATCTAATAAAAAGAACCATCCAGCCG
CGAGGTTAATGACCGCTCTCATGGAATTGGACTTAGATGTGCACCATGC
TAGTGTTTCAGTTGTCAACGGTTGATGATCCAACAAGCGACTTGAACAA
ATGGGAAGCCGGCTTTACACGCAAGAACAACTTCGGATATCATTGACAT
CCAGAATTGCTGAATCGCGATGAAGAGAAATACAGTAAATGGAAATTAT
CATAGTGAGCTCTGAATAATGTTATCTTTCATTGAGCTATTTTAAGAGA
ATTTCTCCT AAAAAAAAAAAAAAAAAAAAAAAAAAA
```
SEQ ID NO: 1

NtMYC2a amino acid sequence (659 AA)
```
M T D Y R I P T M T N I W S N T T S D D N M M E
A L S S D P S S F W P G T T T T
P T P R S S V S P A P A P V T G I A G D P L K S
M P Y F N Q E S L Q Q R L Q T L I D
G A R K G W T Y A I F W Q S S V V D F A S P S V
L G W G S G Y Y K G E E D K N K
R K T A S F S P D F I T E Q A H R K K V L R E L
N S L I S G T Q T G G E N D A V D E
E V T D T E W F F L I S M T Q S F V N G S G L P
G L A M Y S S S P I W V T G T E R L
A V S H C E R A R Q A Q G F G L Q T I V C I P S
A N G V V E L G S T E L I F Q T A D
L M N K V K V L F N F N I D M G A T T G S G S G
S C A I Q A E P D P S A L T L T D
P A S S V V E V K D S S N T V P S R N T S K Q L
V F G N E N S E N G N Q N S Q Q T
Q G F F T R E L N F S E Y G F D G S N T R Y G N
G N A N S S R S C K P E S G E I L N
F G D S T K R S A C S A N G S L F S G Q S Q F G
P G P A E E N K N K N K K R S P A
S R G S N D E G I L S F V S G V I L P S S N T G
K S G G G G D S D Q S D L E A S V V
K E A D S S R V V D P E K K P R K R G R K P A N
G R E E P L N H V E A E R Q R R E
K L N Q R F Y A L R A V V P N V S K M D K A S L
L G D A I A F I N E L K S K V Q N
S D S D K E D L R N Q I E S L R N E L A N K G S
N Y T G P P P S N Q E L K I V D M D
I D V K V I G W D A M I R I Q S N K K N H P A A
R L M T A L M E L D L D V H H A S
V S V V N E L M I Q Q A T V K M G S R L Y T Q E
Q L R I S L T S R I A E S R
```
SEQ ID NO: 2

NtMYC2b cDNA (full-length, 2391 bp)
```
GTAACAAACCCTCTCCATTTTCACTCACTCCAAAAAACTTTCCTCTCTA
TTTTTTCGTTTTTGTTATATGGAATGACGGACTATAGAATACCAACGAT
GACTAATATATGGAGCAATACAACATCCGACGATAACATGATGGAAGCT
TTTTTATCTTCTGATCCGTCGTCGTTTTGGGCCGGAACAAATACACCAA
CTCCACGGAGTTCAGTTTCTCCGGCGCCGGCGCCGGTGACGGGGATTGC
CGGAGACCCATTAAAGTCGATGCCGTATTTCAACCAAGAGTCGCTGCAA
CAGCGACTCCAGACTTTAATCGACGGGGCTCGCGAAGCGTGGACTTACG
CCATATTCTGGCAATCGTCTGTTGTGGATTTCGTGAGCCCCTCGGTGTT
GGGGTGGGGAGATGCATATTTATAAAGGAGAAGAAGACAAGAATAAGCGT
AAAACGGCGGCGTTTTCGCCTGACTGATTTTATTACGGAGCAAGAACACCGGA
AAAAAGTTCTCCGGGAGCTGAATTCTTTAATTTCCGGCACACAAACTGG
TGGTGAAAATGATGCTGTAGATGAAGAAGTAACGGATACTGAATGGTTT
TTTCTGATTTCAATGACTCAATCGTTTGTTAACGGAAGCGGGCTTCCGG
GCCTGGCTATGTACAGCTCAAGCCCGATTTGGGTTACTGGAAGAGAAAG
ATTAGCTGCTTCTCACTGTGAACGGGCCCGACAGGCCCAAGGTTTCGGG
CTTCAGACTATGGTTTGTATTCCTTCAGCTAATGGTGTTGTTGAGCTCG
GGTCAACTGAGTTGATATTCCAGAGCGCTGATTTAATGAACAAGGTTAA
AATCTTGTTTGATTTTAATATTGATATGGGCGCGACTACGGGCTCAGGT
TCGGGTCATGTGCTATTCAGGCTGAGCCCGATCCTTCAACCCTTTGGC
TTACGGATCCACCTTCCTCAGTTGTGGAAGTCAAGGATTCGTCGAATAC
AGTTCCTTCAAGTAATAGTAGTAAGCAACTTGTGTTTGGAAATGAGAAT
TCTGAAAATGTTAATCAAAATTCTCAGCAAACACAAGGATTTTTCACTA
GGGAGTTGAATTTTTCCGAATATGGATTTGATGGAAGTAATACTAGGAG
TGGAAATGGGAATGTGAATTCTTCGCGTTCTTGCAAGCCTGAGTCTGGC
GAAATCTTGAATTTTGGTGATAGTACTAAGAGAAATGCTTCAAGTGCAA
ATGGGAGCTTGTTTTCGGGGCAATCAGTTCGGTCCCGGCCTGGT
GGAGAACAAGAACAAGAACAAGAAAAGGTCACCTGCATCAAGAGGAAGC
AATGAAGAAGGAATGCTTTCATTTGTTTCGGGTGTGATCTTGCCAAGTT
CAAACACGGGAAGTCCGGTGGAGGTGGCGATTCGGATCATTCAGATCT
CGAGGCTTCGGTGGTGAAGGAGGCGGATAGTAGTAGAGTTGTAGACCCC
GAGAAGAGGCCGAGGAAACGAGGGAAAACCGGCTAACGGGAGAGGAGAAC
AGCCATTGAATCATGTGGAGGCAGAGAGGCAAACGGAGGGAGAAATTGA
ATCAAAGATTCTATGCACTTAGAGCTGTTGTACCAAATGTGTCAAAAAT
GGATAAAGCATCACTTCTTGGTGATGCAATTGCATTTATCAATGAGTTG
AAATCAAAGGTTCAGAATTCTGACTCAGATAAAGATGAGTTGAGGAACC
AAATTGAATCTTTAAGGAATGAATTAGCCAACAAGGATCAAACTATAC
CGGTCCTCCACCGCCAAATCAAGATCTCAAGATTGTAGATATGGATATC
GACGTTAAACTCATCGGATGGGATGCTATGATTCGTATACAATCTAATA
AAAAGAACCATCCAGCCGCGAGGTTAATGGCCGCTCTCATGGAATTGGA
CTTAGATGTGCACCATGCTAGTGTTTCAGTTGTCAACGAGTTGATGATC
CAACAAGCGACAGTGAAAATGGGGAGCCGGCTTTACACGCAAGAGCAGC
TTCGGATATCATTGACATCCAGAATTGCTGAATCGCGATGAAGAGAAAT
ACAGTAAATGAAATTATTAGTGAGCTCTGAATAATGTTATCTTTCATT
GAGCTATTTTAAGAGAATTTCTCCTATAGTTAGATCTTGAGATTAAGGC
TACTTAAAAGTGGAAAGTTGATTGAGCTTTCCTCTTAGTTTTTGGGTA
TTTTTCAACTTTTATATCTAGTTTGTTTTCCACATTTTCTGTACATATA
ATGTGAAACCAATACTAGATCTCAAGATCTGGTTTTTAGTTCTGTAATT
AGAAATAAATATGCAGCTTCATCTTTTTCTGTTAAAAAAAAAAAAAAAA
```

APPENDIX-continued

Nucleotide and amino acid sequences of the transcription factors isolated in this research NtMYC2b amino acid sequence (658 AA)
M T D Y R I P T M T N I W S N T T S D D N M M E
A F L S S D P S S F W A G T N T P
T P R S S V S P A P A P V T G I A G D P L K S M
P Y F N Q E S L Q Q R L Q T L I D G
A R E A W T Y A I F W Q S S V V D F V S P S V L
G W G D G Y Y K G E E D K N K R
K T A A F S P D F I T E Q E H R K K V L R E L N
S L I S G T Q T G G E N D A V D E E
V T D T E W F F L I S M T Q S F V N G S G L P G
L A M Y S S S P I V T G R E R L A
A S H C E R A R Q A Q G F G L Q T M V C I S A N
G V V E L G S T E L I F Q S D L
M N K V K I L F D F N I D M G A T T G G S G S C
A I Q A E P D P S T L W L T D P P
S S V V E V K D S S N T V P S S N S S K Q L V F
G N E N S E N V N Q N S Q Q T Q G
F F T R E L N F S E Y G F D G S N T R S G N G N
V N S S R S C K P E S G E I L N F G
D S T K R N A S S A N G S L F S G Q S Q F G P G
P A E E N K N K N K K R S P A S R
G S N E E G M L S F V S G V I L P S S N T G K S
G G G G D S D H S D L E A S V V K
E A D S R V V T D P E K R P R K R G R K P A N G
R E E P L N H V E A E R Q R R E K
L N Q R F Y A L R A V V P N V S K M D K A S L L
G D A I A F I N E L K S K V Q N S
D S D K D E L R N Q I E S L R N E L A N K G S N
Y T G P P P P N Q D L K I V D M D I
D V K V I G W D A M I R I Q S N K K N H P A A R
L M A A L M E L D L D V H H A S
V S V V N E L M I Q Q A T V K M G S R L Y T Q E
Q L R I S L T S R I A E S R SEQ ID NO: 4

NtERF98 cDNA (full-length, 1019 bp)
CACCGTCTCTTTCCATTTCTTTCTCTTAAAAGAAAAAACATCTCAATAA
CAAAAAGAAAAATGTGTGGAGGTGCCATAATCCCCGACTATGAACCCGT
CGGAAACCGCTGCCGGAAAATCACTGCTAGTGACCTCTGGGCTGAGCTT
GACCCTATCTCCGACTTCTGGTCTTCCTCTTCCTCTTCCTCCTCCATTG
CCGGCAAATCTGATTCCGTTCAGTCGCTAACCCACTCCTACAATAAGCC
TCAGAAATCAGATTCCGGCAAACTTAATCAACTCGAAAAAGGTACAATA
AGTGTGAAGGTTGAGAAGGAGAGCAGTGGCCCAAGGGCGAGGAAGAACA
AATACAGAGGAATAAGGCAGAGACCGTGGGGAAAATGGGCTGCTGAGAT
ACGTGATCCTCAGAAAGGCGTCCGCGTGTGGTTAGGTACATTCAACACG
GCTGAGGAAGCTGCCAGGGCATATGACGAGGCTGCAAAGCGAATCCGCG
GTGACAAGGCTAAGCTCAACTTTCCAGAGCCACCTTCGCCACCAGCCAA
GCGACACTGCACTAGCACCATCCCTGATCAGCCCACACGTTCTGACTTA
ATGTCTCAGAAACCGGCCTCAATAATGTTGAACTATGGATATGAAAACC
AAACACCCTACTACCCCATGGAAATGCCCGCTGCTGAGGATCCTGAAGA
TCATGATTATGAGCTCAAGGAGCAGATTTCCAACTTGGAGTCATTCCTG
GATTTAGAGCCAGACTCAGGGATCGTCGATTCTGACCCCCTCAATATTT
TTCTGATGGATGACTTTGCTGCAACTCAGCAGCAGCAGCTGTTTTACTG
AACACTGTAAAAATTATCATACTACTAGTTAATTTCATCCTAAGTTG
TTTGGTGTGCGTTTTCTGATGAGTGACTAGTTAGCTTTTGGTAGTACGT
AGTACAATGCAGAAAGTACATACAATAATAAGTTGCGTGCCTTTGCATG
CAATTTGTAATATTAATGTCATGTTGTTTTGTGCTGTTTAAAAAAAAAA
AAAAAAAA SEQ ID NO: 5

NtERF98 amino acid sequence (257 AA)
M C G G A I I P D Y E P V G N R C R K I T A S D
L W A E L D P I S D P W S S S S S
S S I A G K S D S V Q S L T H S Y N K P Q K S D
S G K L N Q L E K G T I S V K V E K
E S S G P R A R K N K Y R G I R Q R P W G K W A
A E I R D P Q K G V R V W L G T
F N T A E E A A R A Y D E A A K R I R G D K A K
L N F P E P P S P P A K R H C T S T
I P D Q P T R S D L M S Q K P A S I M L N Y G Y
E N Q T P Y Y P M E M P A A E D P
Q H H D Y E L K E Q I S N L E S F L D L E P D S
G I V D S D P L N I F L M D D F A A
T Q Q Q Q L F Y SEQ ID NO: 6

NtETTa cDNA (full-length, 2429 bp)
AGCAAAAGGGTTTGAAGATGATGTGTGGACTTATTGATCTAAATACTGT
GGATAACGATGACGTCGGAGAAGAAACGACGGCGCCGGTGTCACCAGCG
TCATCGTCGACGGCGTCTGGATGTTCGGATTTGACGTCGTCATCTCTGC
CGGCGATGGCATCGTTTGTCTGGAGCTGTGGCATCCGTGTGCTGGACC
GTTGATTTCTCTGCCGAAGAAAGGAAGTGCTGTTGTGTACCTACCTCAA
GGTCACTTGGAACATCTCTCTGACTACCCGCCATAGCCTATAACCTCC
CTCCTCACGTTTTTTTGTCGCGTCGTAGACGTGAAGCTACAAGCGGATG
CGGCGAGTGATGAGGTCTATGCACAAGTCTCACTGGTTCCAGACAATCA
GATTGAGCAGAAATGGAGGGATGGAGACATTGATGCAGATACTGAAGAG
GAGGAAATAGAAGGTGCTGGAAAATCAACAACACCACACATGTTCTGCA
AGACTCTCACTGCTTCGGATACCAGCACTCATGGCGGTTTTCTGTCCC
TCGCCGGGCTGCAGAAGATTGCTTTCCTCCATTGGATTACAGACAACAG
CGGCCCTCACAGGAGCTGGTAGCCAAAGATCTACATGGTATCGAGTGGA
AATTTCGGCATATCTATCGTGGTCAGCCACGAAGGCATCTGCTCACTAC
AGGATGGAGTGCGTTTGTAAACAGGAAGACTTGTTTCTGGTGACGCT
GTGCTTTCTTAAGGACTGCTGATGGAGAACTTAGGCTAGGGGTGAGAC
GAGCTGCCAAGCTAAAACATGTTCAAATTATCTAGCTGCCTATAGCCA
ACTGTTGAATGTCAGTGGTATTGTGGATGTGGTTAAGGCCATATCTAGC
ACAAATGCCTTCAGTATCTGTTATAACCCGAGGGCTAGCTCATCAGGT
TCATTTTACCTTACCACAAATTCTCAAAGACTCTTGCACATCCCTTTTC
AGCTGGAATGAGATTTAAGATGCGTGTCGAAACAGAAGATGCAGCTGAA
CAAAGGTTCACTGGACTTGTTGTAGGAGTCAGCGATGTAGATCCAGTTC
GCTGGCCTTCTAAATGGAAGGTGCCTATTGGTCAGGTGGGATGATCT
TGATGTTTCTCGGCATAATAGGGTTTCACCGTGGGAAATTCAGCCATCT
GGTTCAGCTCCTGTATCCAGCAGCTTGGTGATGCCTTCTGCGAAGAGGA
CCAGGGTTGGCTTTCCAATTACAAAGGCCGATTTTCCAATTCCTAGAGA
TGGGATTGCAGTATCAGACTTTGGGGAATCTTCTAGGTTCCAGAAGGTC
TTGCAAGGTCAAGAAATTTTGGGGATTAGTTCTCCTTTTGTCGGTTTTG
ATGCTCACAGTCCTCGTACAGCGGGGATAAGATGCTTTCCTGGTTTTCC
TAGTTCTGGGGCATCTAGATTGGGAAACAGCATCAGAACCCTGCTTGGT
GACACAGACAAGTCCCCTGAAAGCATTGGCTTTAGTGATTCTTCTGAT
ACAATAAGGTCTTGCAAGGTCAAGAAACTTTTTCAACCCCTCCTTATGG
GAGAGGTCATGCAGGTAGCCTAATGCAGGAAAAAAGTAGAACTGGTATT
ATCGTCGGTATTCAGGTTCCAAGCCACGTAAACAGGTGGTCTGCTCCAA
ATCAGGGTAATCGCAGTCATTGCAATCCAAGTACTTGTCCCGGCATC
ATCACCTCCTTCTGTGCTCAGCTTTCAGCCTCCCAGGTCTCCAGACATCA
AAATTCCAGGCTATGTTCAATCATAAACATGGGAAGCTTGAGACTGCTA
CCCAGGCTTTGGATATGTCTGAGAGCTGTAGTAGGCATCTCGCATCTGG
CTCACATGCCGAGGACATCAGTAGGAAGGGAGACACAAAAGGAATCAGT
TCTTTTAGTTTCTTAAAGGAGCAAAAGCAAACAGGAATTTCATATCTTT
CTCTTGGGACCCAGTCGTCTCAAAACTTAGTTTCCATGTGTAAAACCAG
TTGCAGGATCTTTGGATTCCCCTTGACCGAGAGTAAAATAAATGCAGCT
AGAGCGGAGAATCCTGCCGAGGCTGTATATTCACATGGTCTAGAAACAA
CATTTCTGCCTTCCCAGTTGCAGCCAGGGCCACCATTGAT
GACTAATGTTGTGGGAACAAACTTTACTAAAGTAAATGACCTCTATGAT
GCAAGAGATGTGATTCTTGATATTGCTTTGTAGCAAGTATTTGTTGTGA
AGTCATGAGCATATGTAAACTGAAGGATGTGTGAGCAGTATTATTGATT
CTTAGATTTTAGTTGCTGATTAGTTTTGGCCAATGAACGCAAGCATGT
AGTTGCCAGTACAATGCTTATCCTGAGATGAGTATTGAGACTTTTTTAT
TGTAAGGAACACAGTGAAGATTAGTATTGTAAAAAAAAAAAAAAAAAAA
AAAAAAAA SEQ ID NO: 7

NtETTa amino acid sequence (739 AA)
M M C G L I D L N T V D N D D V G E E T T A P V S
P A S S S T A S G C S D L T S S S
L P A M A S V C L E L W H A C A G P L I S L P K
K G S A V V Y L P Q G H L E H L S
E Y P P I A Y N L P P H V F C R V V D V K L Q A
D A A S D E V Y A Q V S L V P D N
Q I E Q K W R D G D I D A D T E E E E I E G A G
K S T T P H M F C K T L T A S D T S
T H G G F S V P R R A A E D C F P P L D Y R Q Q
R P S Q E L V A K D L H G I E W K
F R H I Y R G Q P R R H L L T T G W S A F V N R
K K L V S G D A V L F L R T A D G
E L R L G V R R A A Q A K T C S N Y L A A Y S Q
L L N V S G I V D V V K A I S S T
N A F S I C Y N P R A S S S G F I L P Y H K F S
K T L A H P F K A G M R F K M R V E
T E D A A E Q R F T G L V V G V S D V D P V R W
P G S K W R C L L V R W D D L D
V S R H N R V S P W E I E P S G S A P V S S S L
V M P S A K R T R V G F P I T K A D
F P I P R D G I A V S D F G E S S R F Q K V L Q
G Q E I L G I S S P F V G F D A H S P
R T A G I R C F P G F P S S G A S R L G N S I R
T L L G D T D K S P E S I G F S D S S
R Y N K V L Q G G Q E T F S T P P Y G R G H A G S

APPENDIX-continued

Nucleotide and amino acid sequences of the transcription factors isolated in this research L M Q E K S R T G I I V G I Q V P S
H V N R W S A P N Q G N R S H C N P S T L V P A
S S P P S V L S F Q P P R S P A S K
F Q A M F N H K H G K L E T A T Q A L D M S E S
C S R H L A S G S H A E D I S R K
G D T K G I S S F S F L K E Q K Q T G I S Y L S

APPENDIX-continued

Nucleotide and amino acid sequences of the transcription factors isolated in this research 5
L G T Q S S Q N L V S M C K T S C R I
F G F P L T E S K I N A A R A E N P A E A V Y S
H G L E T T F L P S S D G K L Q P G
P P L M T N V V G T N F T K V N D L Y A A R D V
I L D I A L SEQ ID NO: 8

---

That which is claimed is:

1. A tobacco plant regenerated from a tobacco plant cell comprising a mutant allele of a gene encoding a transcription factor that modulates nicotine biosynthesis, wherein the tobacco plant cell is produced by a method comprising:
   (a) introducing into a population of tobacco plant cells a reagent for site-directed mutagenesis comprising an oligonucleotide having a targeting sequence with at least 96% sequence identity to SEQ ID NO: 1, SEQ ID NO: 3, or a complement thereof, thereby producing the tobacco plant cell comprising the mutant allele of the gene encoding the transcription factor that modulates nicotine biosynthesis; and
   (b) regenerating a tobacco plant from the tobacco plant cell of step (a),
   thereby resulting in a tobacco plant comprising tobacco plant cells comprising the mutant allele of the gene encoding the transcription factor that modulates nicotine biosynthesis.

2. Seeds from or a progeny plant of the tobacco plant of claim 1, wherein the seeds or progeny plant comprise in their genomes the mutant allele.

3. A crop comprising a plurality of the tobacco plants of claim 1 or a progeny thereof, wherein the plurality of tobacco plants or progeny thereof comprise in their genomes the mutant allele.

4. A tobacco product produced from the plant of claim 1, wherein the product comprises the mutant allele.

5. The tobacco product of claim 4, wherein the tobacco product is selected from the group consisting of a smoking cessation product, a cigarette, cigarette tobacco, cigar tobacco, a cigar, pipe tobacco, chewing tobacco, snuff, snus, lozenges, leaf tobacco, shredded tobacco, cut tobacco, and any combination thereof.

6. The tobacco product of claim 4, which is a smoking cessation product.

7. The tobacco product of claim 4, which is a cigarette.

8. The tobacco plant of claim 1, wherein the oligonucleotide has a targeting sequence with a sequence identity of at least about 97%, about 98% or about 99% to SEQ ID NO: 1, SEQ ID NO: 3, or a complement thereof.

* * * * *

UNITED STATES PATENT AND TRADEMARK OFFICE
CERTIFICATE OF CORRECTION

PATENT NO. : 10,724,045 B2
APPLICATION NO. : 16/059696
DATED : July 28, 2020
INVENTOR(S) : Qu et al.

It is certified that error appears in the above-identified patent and that said Letters Patent is hereby corrected as shown below:

In the Specification

Column 3, Line 60: Please correct "zNtQPT2" to read -- NtQPT2 --

Column 6, Line 34: Please correct "±0.1%6 of" to read -- ±0.1% of --

Column 8, Line 62: Please correct "(1)" to read -- (f) --

Column 9, Line 18: Please correct "SEQ ID NO:7:" to read -- SEQ ID NO:7; --

Column 9, Line 23: Please correct "SEQ ID NO:8:" to read -- SEQ ID NO:8; --

Column 10, Line 60: Please correct "500)," to read -- 500, --

Column 36, Line 11: Please correct "(SD/-Leu/-Trp-His)" to read -- (SD/-Leu/-Trp/-His) --

Column 36, Line 31: Please correct "DH5a" to read -- DH5α --

Column 37, Line 4: Please correct "CGCTGGAGTTGGTGTAGTAG" to read -- CGGGGAGTTGGTGTAGTAG --

Column 38, Line 23: Please correct "pBI21" to read -- pBI121 --

Column 39, Line 21: Please correct "plg" to read -- µg --

Column 39, Line 28: Please insert a paragraph break between "Expression" and "Root"

Column 39, Line 46: Please insert a paragraph break between "(EMSA)" and "Since"

Column 41, Line 43: Please correct "500)" to read -- 500 --

Signed and Sealed this
Twenty-second Day of December, 2020

Andrei Iancu
*Director of the United States Patent and Trademark Office*

CERTIFICATE OF CORRECTION (continued)
U.S. Pat. No. 10,724,045 B2

Column 41, Line 48: Please correct "DH5a" to read -- DH5α --

Column 43, Line 12: Please correct "946" to read -- 94% --

Column 43, Line 44: Please correct "OPT" to read -- QPT --

Column 47, Line 35: Please correct "(2013-A4-1)" to read -- (2013-VA-1) --

Column 49, Line 29: Please correct "OPT" to read -- QPT --

Column 49, Line 36: Please correct "OPT" to read -- QPT --

Column 49, Line 40: Please correct "OPT" to read -- QPT --

Column 50, Line 50: Please correct "OPT" to read -- QPT --

Column 51, Line 10: Please correct "QP7" to read -- QPT --